(12) United States Patent
Winter et al.

(10) Patent No.: US 9,670,482 B2
(45) Date of Patent: *Jun. 6, 2017

(54) MULTISPECIFIC PEPTIDES

(71) Applicant: BICYCLE THERAPEUTICS LIMITED, Cambridge (GB)

(72) Inventors: Gregory Paul Winter, Cambridge (GB); Christian Heinis, Bern (CH); Elise Bernard, Cambridge (GB); David Loakes, Cambridge (GB); John Tite, Herts (GB); Marina Vaysburd, Cambridge (GB); Daniel Paul Teufel, Cambridge (GB); Lutz Riechmann, Cambridge (GB)

(73) Assignee: BICYCLE THERAPEUTICS LIMITED, Cambridge (GB)

( * ) Notice: Subject to any disclaimer, the term of this patent is extended or adjusted under 35 U.S.C. 154(b) by 643 days.
This patent is subject to a terminal disclaimer.

(21) Appl. No.: 14/091,321

(22) Filed: Nov. 26, 2013

(65) Prior Publication Data
US 2014/0163201 A1   Jun. 12, 2014

Related U.S. Application Data

(62) Division of application No. 13/147,289, filed as application No. PCT/EP2010/000689 on Feb. 4, 2010, now Pat. No. 8,685,890.

(30) Foreign Application Priority Data

Feb. 4, 2009  (WO) ................ PCT/GB2009/000301
Aug. 6, 2009  (GB) .................................... 0913775.3

(51) Int. Cl.
C40B 40/10   (2006.01)
C12N 15/10   (2006.01)
(Continued)

(52) U.S. Cl.
CPC ........ *C12N 15/1037* (2013.01); *A61K 47/481* (2013.01); *A61K 47/48246* (2013.01);
(Continued)

(58) Field of Classification Search
None
See application file for complete search history.

(56) References Cited

PUBLICATIONS

Timmerman et al. (Apr. 5, 2005) ChemBioChem vol. 6 pp. 821 to 824.*
Canadian Office Action dated Feb. 29, 2016, pp. 1-6.

* cited by examiner

*Primary Examiner* — Christian Boesen
(74) *Attorney, Agent, or Firm* — Convergent Law Group LLP

(57) ABSTRACT

The invention relates to a method for providing a multispecific peptide ligand comprising a polypeptide covalently linked to a molecular scaffold at three or more amino acid residues and capable of binding to two or more separate targets, comprising the steps of: (a) providing a first repertoire of polypeptides, each polypeptide comprising two or more reactive groups capable of covalent linkage to a molecular scaffold, and at least one loop which comprises a sequence of two or more amino acids subtended between two of said reactive groups; (b) providing a second repertoire of polypeptides as described in (a); (c) joining at least one loop of one or more members of the first repertoire to at least one loop of one or more members of the second repertoire to form at least one polypeptide comprising two loops, and (d) conjugating the composite polypeptide(s) to a molecular scaffold at at least three amino acid positions.

1 Claim, 10 Drawing Sheets

(51) Int. Cl.
  *A61K 47/48* (2006.01)
  *C40B 40/08* (2006.01)
  *C40B 50/06* (2006.01)
  *G01N 33/531* (2006.01)
  *C07K 14/00* (2006.01)

(52) U.S. Cl.
  CPC ...... *A61K 47/48284* (2013.01); *C07K 14/001* (2013.01); *C12N 15/1044* (2013.01); *C12N 15/1058* (2013.01); *C40B 40/08* (2013.01); *C40B 50/06* (2013.01); *G01N 33/531* (2013.01); *C40B 40/10* (2013.01)

SEQUENCE LISTING

<160> NUMBER OF SEQ ID NOS: 26

<210> SEQ ID NO 1
<211> LENGTH: 17
<212> TYPE: PRT
<213> ORGANISM: Artificial Sequence
<220> FEATURE:
<223> OTHER INFORMATION: Engineered peptide
<220> FEATURE:
<221> NAME/KEY: X
<222> LOCATION: (3)..(8)
<223> OTHER INFORMATION: X is any amino acid
<220> FEATURE:
<221> NAME/KEY: X

```
<222> LOCATION: (10)..(15)
<223> OTHER INFORMATION: X is any amino acid

<400> SEQUENCE: 1

Ala Cys Xaa Xaa Xaa Xaa Xaa Cys Xaa Xaa Xaa Xaa Xaa Xaa Cys
1               5                   10                  15

Gly

<210> SEQ ID NO 2
<211> LENGTH: 15
<212> TYPE: PRT
<213> ORGANISM: Artificial Sequence
<220> FEATURE:
<223> OTHER INFORMATION: Engineered peptide

<400> SEQUENCE: 2

Cys Phe Asn Ser Glu Trp Ser Cys Leu Gln Ser Cys Ser Asn Cys
1               5                   10                  15

<210> SEQ ID NO 3
<211> LENGTH: 220
<212> TYPE: PRT
<213> ORGANISM: Artificial Sequence
<220> FEATURE:
<223> OTHER INFORMATION: Engineered peptide

<400> SEQUENCE: 3

Ala Glu Thr Val Glu Ser Cys Leu Ala Lys Pro His Thr Glu Asn Ser
1               5                   10                  15

Phe Thr Asn Val Trp Lys Asp Asp Lys Thr Leu Asp Arg Tyr Ala Asn
                20                  25                  30

Tyr Glu Gly Cys Leu Trp Asn Ala Thr Gly Val Val Cys Thr Gly
            35                  40                  45

Asp Glu Thr Gln Cys Tyr Gly Thr Trp Val Pro Ile Gly Leu Ala Ile
50                  55                  60

Pro Glu Asn Glu Gly Gly Ser Glu Gly Gly Ser Glu Gly Gly
65                  70                  75                  80

Gly Ser Glu Gly Gly Thr Lys Pro Pro Glu Tyr Gly Asp Thr Pro
            85                  90                  95

Ile Pro Gly Tyr Thr Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
            115                 120                 125

Gln Pro Leu Asn Thr Phe Met Phe Gln Asn Asn Arg Phe Arg Asn Arg
    130                 135                 140

Gln Gly Ala Leu Thr Val Tyr Thr Gly Thr Val Thr Gln Gly Thr Asp
145                 150                 155                 160

Pro Val Lys Thr Tyr Tyr Gln Tyr Thr Pro Val Ser Ser Lys Ala Met
                165                 170                 175

Tyr Asp Ala Tyr Trp Asn Gly Lys Phe Arg Asp Cys Ala Phe His Ser
            180                 185                 190

Gly Phe Asn Glu Asp Pro Phe Val Cys Glu Tyr Gln Gly Gln Ser Ser
        195                 200                 205

Asp Leu Pro Gln Pro Pro Val Asn Ala Pro Ser Gly
    210                 215                 220

<210> SEQ ID NO 4
<211> LENGTH: 220
<212> TYPE: PRT
```

<213> ORGANISM: Artificial Sequence
<220> FEATURE:
<223> OTHER INFORMATION: Engineered peptide

<400> SEQUENCE: 4

```
Ala Glu Thr Val Glu Ser Ser Leu Ala Lys Ser His Ile Glu Gly Ser
1               5                   10                  15

Phe Thr Asn Val Trp Lys Asp Lys Thr Leu Asp Trp Tyr Ala Asn
            20                  25                  30

Tyr Glu Gly Ile Leu Trp Lys Ala Thr Gly Val Val Ile Thr Gly
            35                  40                  45

Asp Glu Thr Gln Val Tyr Ala Thr Trp Val Pro Ile Gly Leu Ala Ile
    50                  55                  60

Pro Glu Asn Glu Gly Gly Ser Glu Gly Gly Ser Glu Gly Gly
65                  70                  75                  80

Gly Ser Glu Gly Gly Gly Thr Lys Pro Pro Glu Tyr Gly Asp Thr Pro
                85                  90                  95

Ile Pro Gly Tyr Ile Tyr Ile Asn Pro Leu Asp Gly Thr Tyr Pro Pro
            100                 105                 110

Gly Thr Glu Gln Asn Pro Ala Asn Pro Asn Pro Ser Leu Glu Glu Ser
            115                 120                 125

His Pro Leu Asn Thr Phe Met Phe Gln Asn Asn Arg Phe Arg Asn Arg
    130                 135                 140

Gln Gly Ala Leu Thr Val Tyr Thr Gly Thr Val Thr Gln Gly Thr Asp
145                 150                 155                 160

Pro Val Lys Thr Tyr Tyr Gln Tyr Thr Pro Val Ser Ser Lys Ala Met
                165                 170                 175

Tyr Asp Ala Tyr Trp Asn Gly Lys Phe Arg Asp Val Ala Phe His Ser
            180                 185                 190

Gly Phe Asn Glu Asp Leu Leu Val Ala Glu Tyr Gln Gly Gln Ser Ser
            195                 200                 205

Tyr Leu Pro Gln Pro Pro Val Asn Ala Pro Ser Gly
    210                 215                 220
```

<210> SEQ ID NO 5
<211> LENGTH: 18
<212> TYPE: PRT
<213> ORGANISM: Artificial Sequence
<220> FEATURE:
<223> OTHER INFORMATION: Engineered peptide

<400> SEQUENCE: 5

```
Ser Cys Glu Leu Trp Asn Pro Lys Cys Arg Leu Ser Pro Phe Glu Cys
1               5                   10                  15

Lys Gly
```

<210> SEQ ID NO 6
<211> LENGTH: 18
<212> TYPE: PRT
<213> ORGANISM: Artificial Sequence
<220> FEATURE:
<223> OTHER INFORMATION: Engineered peptide

<400> SEQUENCE: 6

```
Ser Cys Val Arg Phe Gly Trp Thr Cys Asp Asn Ser Trp His Gly Cys
1               5                   10                  15

Lys Gly
```

```
<210> SEQ ID NO 7
<211> LENGTH: 12
<212> TYPE: PRT
<213> ORGANISM: Artificial Sequence
<220> FEATURE:
<223> OTHER INFORMATION: Engineered peptide

<400> SEQUENCE: 7

Thr Ser Phe Ala Glu Tyr Trp Asn Leu Leu Ser Pro
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Engineered peptide

<400> SEQUENCE: 8

Ala Cys Ser Asp Arg Phe Arg Asn Cys Pro Ala Asp Glu Ala Leu Cys
1               5                   10                  15

Gly

<210> SEQ ID NO 9
<211> LENGTH: 21
<212> TYPE: PRT
<213> ORGANISM: Artificial Sequence
<220> FEATURE:
<223> OTHER INFORMATION: Engineered peptide

<400> SEQUENCE: 9

Ala Leu Cys Ile Phe Asp Leu Gly Phe Cys Ser Asp Arg Phe Arg Asn
1               5                   10                  15

Cys Pro Ala Asp Glu
            20

<210> SEQ ID NO 10
<211> LENGTH: 17
<212> TYPE: PRT
<213> ORGANISM: Artificial Sequence
<220> FEATURE:
<223> OTHER INFORMATION: Engineered peptide

<400> SEQUENCE: 10

Ala Cys Ser Asp Arg Phe Arg Asn Cys Ile Phe Asp Leu Gly Phe Cys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: Engineered peptide

<400> SEQUENCE: 11

Ala Cys Ser Asp Arg Phe Arg Asn Cys Val Arg Phe Gly Trp Thr Cys
1               5                   10                  15

Gly

<210> SEQ ID NO 12
<211> LENGTH: 20
<212> TYPE: PRT
<213> ORGANISM: Artificial Sequence
<220> FEATURE:
```

```
<223> OTHER INFORMATION: Engineered peptide

<400> SEQUENCE: 12

Trp Gly Gly Gly Cys Val Arg Phe Gly Trp Thr Cys Ser Asp Arg Phe
1               5                   10                  15

Arg Asn Cys Gly
            20

<210> SEQ ID NO 13
<211> LENGTH: 5
<212> TYPE: PRT
<213> ORGANISM: Artificial Sequence
<220> FEATURE:
<223> OTHER INFORMATION: Engineered peptide

<400> SEQUENCE: 13

Gly Gly Ser Gly Asp
1               5

<210> SEQ ID NO 14
<211> LENGTH: 5
<212> TYPE: PRT
<213> ORGANISM: Artificial Sequence
<220> FEATURE:
<223> OTHER INFORMATION: Engineered peptide

<400> SEQUENCE: 14

Phe Gly Gly Gly Asp
1               5

<210> SEQ ID NO 15
<211> LENGTH: 5
<212> TYPE: PRT
<213> ORGANISM: Artificial Sequence
<220> FEATURE:
<223> OTHER INFORMATION: Engineered peptide

<400> SEQUENCE: 15

Phe Gly Ser Gly Asp
1               5

<210> SEQ ID NO 16
<211> LENGTH: 5
<212> TYPE: PRT
<213> ORGANISM: Artificial Sequence
<220> FEATURE:
<223> OTHER INFORMATION: Engineered peptide

<400> SEQUENCE: 16

Trp Gly Ser Gly Asp
1               5

<210> SEQ ID NO 17
<211> LENGTH: 21
<212> TYPE: PRT
<213> ORGANISM: Artificial Sequence
<220> FEATURE:
<223> OTHER INFORMATION: Engineered peptide

<400> SEQUENCE: 17

Trp Gly Gly Gly Ala Cys Val Arg Phe Gly Trp Thr Cys Ser Asp Arg
1               5                   10                  15

Phe Arg Asn Cys Gly
            20
```

```
<210> SEQ ID NO 18
<211> LENGTH: 5
<212> TYPE: PRT
<213> ORGANISM: Artificial Sequence
<220> FEATURE:
<223> OTHER INFORMATION: Engineered peptide

<400> SEQUENCE: 18

Trp Gly Gly Gly Ala
1               5

<210> SEQ ID NO 19
<211> LENGTH: 17
<212> TYPE: PRT
<213> ORGANISM: Artificial Sequence
<220> FEATURE:
<223> OTHER INFORMATION: Engineered peptide

<400> SEQUENCE: 19

Ala Cys Ser Asp Arg Phe Arg Asn Cys Pro Ala Asp Glu Ala Leu Cys
1               5                   10                  15

Gly

<210> SEQ ID NO 20
<211> LENGTH: 21
<212> TYPE: PRT
<213> ORGANISM: Artificial Sequence
<220> FEATURE:
<223> OTHER INFORMATION: Engineered peptide

<400> SEQUENCE: 20

Ser Cys Val Arg Phe Gly Trp Thr Cys Asp Asn Ser Trp His Gly Cys
1               5                   10                  15

Lys Gly Arg Arg Arg
            20

<210> SEQ ID NO 21
<211> LENGTH: 21
<212> TYPE: PRT
<213> ORGANISM: Artificial Sequence
<220> FEATURE:
<223> OTHER INFORMATION: Engineered peptide

<400> SEQUENCE: 21

Ser Cys Val Arg Phe Gly Trp Thr Cys Asp Asn Ser Trp His Gly Cys
1               5                   10                  15

Lys Gly Asp Asp Asp
            20

<210> SEQ ID NO 22
<211> LENGTH: 22
<212> TYPE: PRT
<213> ORGANISM: Artificial Sequence
<220> FEATURE:
<223> OTHER INFORMATION: Engineered peptide

<400> SEQUENCE: 22

Ser Gly Cys Val Arg Phe Gly Trp Thr Cys Pro Thr Val Met Cys Gly
1               5                   10                  15

Gly Arg Arg Arg Arg Arg
            20

<210> SEQ ID NO 23
<211> LENGTH: 24
<212> TYPE: PRT
```

```
<213> ORGANISM: Artificial Sequence
<220> FEATURE:
<223> OTHER INFORMATION: Engineered peptide

<400> SEQUENCE: 23

Ser Gly Cys Val Arg Phe Gly Trp Thr Cys Pro Thr Val Met Cys Gly
1               5                   10                  15

Gly Arg Arg Arg Arg Gly Leu
            20

<210> SEQ ID NO 24
<211> LENGTH: 28
<212> TYPE: PRT
<213> ORGANISM: Artificial Sequence
<220> FEATURE:
<223> OTHER INFORMATION: Engineered peptide

<400> SEQUENCE: 24

Ser Gly Cys Val Arg Phe Gly Trp Thr Cys Pro Thr Val Met Cys Gly
1               5                   10                  15

Gly Tyr Gly Arg Lys Lys Arg Arg Gln Arg Arg Arg
            20                  25

<210> SEQ ID NO 25
<211> LENGTH: 33
<212> TYPE: PRT
<213> ORGANISM: Artificial Sequence
<220> FEATURE:
<223> OTHER INFORMATION: Engineered peptide

<400> SEQUENCE: 25

Ser Gly Cys Val Arg Phe Gly Trp Thr Cys Pro Thr Val Met Cys Gly
1               5                   10                  15

Gly Arg Gln Ile Lys Ile Trp Phe Gln Asn Arg Arg Met Lys Trp Lys
            20                  25                  30

Lys

<210> SEQ ID NO 26
<211> LENGTH: 85
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: XAA
<222> LOCATION: (1)..(20)
<223> OTHER INFORMATION: XAA = 20 OF ANY AMINO ACID OR LESS THAN TWENTY,
      INCLUDING 0-20
<220> FEATURE:
<221> NAME/KEY: XAA
<222> LOCATION: (22)..(41)
<223> OTHER INFORMATION: XAA = 20 OF ANY AMINO ACID OR LESS THAN TWENTY,
      INCLUDING 1-20
<220> FEATURE:
<221> NAME/KEY: XAA
<222> LOCATION: (43)..(62)
<223> OTHER INFORMATION: XAA = 20 OF ANY AMINO ACID OR LESS THAN TWENTY,
      INCLUDING 1-20
<220> FEATURE:
<221> NAME/KEY: XAA
<222> LOCATION: (64)..(85)
<223> OTHER INFORMATION: XAA = 20 OF ANY AMINO ACID OR LESS THAN TWENTY,
      INCLUDING 0-20

<400> SEQUENCE: 26

Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Cys Xaa Xaa Xaa Xaa Xaa Xaa Xaa Xaa Xaa Xaa
            20              25              30

Xaa Xaa Xaa Xaa Xaa Xaa Xaa Xaa Xaa Cys Xaa Xaa Xaa Xaa Xaa
            35              40              45

Xaa Xaa Xaa Xaa Xaa Xaa Xaa Xaa Xaa Xaa Xaa Xaa Xaa Cys Xaa
    50              55              60

Xaa Xaa Xaa Xaa Xaa Xaa Xaa Xaa Xaa Xaa Xaa Xaa Xaa Xaa Xaa
65          70              75              80

Xaa Xaa Xaa Xaa Xaa
            85
```

MULTISPECIFIC PEPTIDES

CROSS REFERENCE TO RELATED APPLICATIONS

This application is a divisional application of Ser. No. 13/147,289, filed Dec. 28, 2011, which was a §371 filing of PCT/EP2010/000689, filed Feb. 4, 2010, which claims priority to PCT/GB2009/000301, filed Feb. 4, 2009 and GB0913775.3, filed Aug. 6, 2009.

FIELD OF THE INVENTION

The present invention relates to peptides whose structure is constrained by binding to a compound which provides a structural backbone, imparting a conformation to the peptide. In particular, the invention relates to such peptides which possess binding affinity for two or more molecular targets, which can be the same or different.

BACKGROUND OF THE INVENTION

Polypeptides having dual specificity are known in the art. In particular, antibody molecules have been designed which are capable of binding to two different antigens, or to two epitopes on the same antigen molecule, simultaneously.

Bispecific antibodies comprising complementary pairs of $V_H$ and $V_L$ regions are known in the art. These bispecific antibodies comprise two pairs of $V_H$ and $V_L$s, each $V_H V_L$ pair binding to a single antigen or epitope. Such bispecific antibodies include hybrid hybridomas (Milstein & Cuello A C, Nature 305: 537-40), minibodies (Hu et al., (1996) Cancer Res 56: 3055-3061), diabodies (Holliger et al., (1993) Proc. Natl. Acad. Sci. USA 90, 6444-6448; WO 94/13804), chelating recombinant antibodies (CRAbs; (Neri et al., (1995) J. Mol. Biol. 246, 367-373), biscFv (e.g. Atwell et al., (1996) Mol. Immunol. 33, 1301-1312), "knobs in holes" stabilised antibodies (Carter et al., (1997) Protein Sci. 6, 781-788). In each case each antibody species comprises two antigen-binding sites, each fashioned by a complementary pair of $V_H$ and $V_L$ domains. Each antibody is thereby able to bind to two different antigens or epitopes at the same time, with the binding to each antigen or epitope mediated by a $V_H$ and its complementary $V_L$ domain.

Two different antibody binding specificities can moreover be incorporated into the same binding site. In most cases, two or more specificities that correspond to structurally related antigens or epitopes or to antibodies that are broadly cross-reactive can be targeted. For example, cross-reactive antibodies have been described, usually where the two antigens are related in sequence and structure, such as hen egg white lysozyme and turkey lysozyme (McCafferty et al., WO 92/01047) or to free hapten and to hapten conjugated to carrier (Griffiths A D et al. EMBO J. 1994 13: 14 3245-60). In a further example, WO 02/02773 (Abbott Laboratories), describes antibody molecules with "dual specificity". The antibody molecules referred to are antibodies raised or selected against multiple antigens, such that their specificity spans more than a single antigen. Each complementary $V_H/V_L$ pair in the antibodies of WO 02/02773 specifies a single binding specificity for two or more structurally related antigens; the $V_H$ and $V_L$ domains in such complementary pairs do not each possess a separate specificity. The antibodies thus have a broad single specificity which encompasses two antigens, which are structurally related. Furthermore natural autoantibodies have been described that are polyreactive (Casali & Notkins, Ann. Rev. Immunol. 7, 515-531), reacting with at least two (usually more) different antigens or epitopes that are not structurally related. It has also been shown that selections of random peptide repertoires using phage display technology on a monoclonal antibody will identify a range of peptide sequences that fit the antigen binding site. Some of the sequences are highly related, fitting a consensus sequence, whereas others are very different and have been termed mimotopes (Lane & Stephen, Current Opinion in Immunology, 1993, 5, 268-271). It is therefore clear that the binding site of an antibody, comprising associated and complementary $V_H$ and $V_L$ domains, has the potential to bind to many different antigens from a large universe of known antigens.

WO03/002609 (Domantis) describes the production of dual specific antibodies in which each $V_H/V_L$ pair possesses a dual specificity, i.e. is able to bind two epitopes on the same or different antigens. The conformation can be open or closed; in an open conformation, the two epitopes may be bound simultaneously, but in the closed conformation binding to the first epitope prevents or discourages binding to the second.

Non-immunoglobulin proteins with multiple binding specificities are known in nature; for example, a number of transcription factors bind both DNA and other protein molecules. However, methods for selecting binding peptides in the prior art only select peptides with single, not dual or multiple specificities.

Different research teams have previously tethered polypeptides with cysteine residues to a synthetic molecular structure (Kemp, D. S. and McNamara, P. E., J. Org. Chem., 1985; Timmerman, P. et al., ChemBioChem, 2005). Meloen and co-workers had used tris(bromomethyl)benzene and related molecules for rapid and quantitative cyclisation of multiple peptide loops onto synthetic scaffolds for structural mimicry of protein surfaces (Timmerman, P. et al., ChemBioChem, 2005). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

WO2004/077062 discloses a method of selecting a candidate drug compound. In particular, this document discloses various scaffold molecules comprising first and second reactive groups, and contacting said scaffold with a further molecule to form at least two linkages between the scaffold and the further molecule in a coupling reaction.

WO2006/078161 discloses binding compounds, immunogenic compounds and peptidomimetics. This document discloses the artificial synthesis of various collections of peptides taken from existing proteins. These peptides are then combined with a constant synthetic peptide having some amino acid changes introduced in order to produce combinatorial libraries. By introducing this diversity via the chemical linkage to separate peptides featuring various amino acid changes, an increased opportunity to find the desired binding activity is provided. FIG. 7 of this document shows a schematic representation of the synthesis of various loop peptide constructs. However, the peptides produced have single specificities. Where multiple peptide loops are provided, the loops cooperate to bind to a single target.

In our copending unpublished international patent application PCT/GB2009/000301 we disclose the use of biological selection technology, such as phage display, to select peptides tethered to synthetic molecular structures.

SUMMARY OF THE INVENTION

We have developed multispecific binding polypeptides based on a polypeptide tethered to a molecular scaffold to form at least two peptide loops. Multiple specificity can be achieved in one of three ways.

In a first configuration of the invention, the polypeptide loops formed by the interaction of the polypeptide with the molecular scaffold are capable of binding to more than one target. Within this configuration, in one embodiment loops may be selected individually for binding to the desired targets, and then combined. In another embodiment, the loops are selected together, as part of a single structure, for binding to different desired targets.

In a second configuration, a functional group may be attached to the N or C terminus, or both, of the polypeptide. The functional group may take the form of a binding group, such as a polypeptide, including an antibody domain, an Fc domain or a further structured peptide as described above, capable of binding to a target. It may moreover take the form of a reactive group, capable of chemical bonding with a target. Moreover, it can be an effector group, including large plasma proteins, such as serum albumin, and a cell penetrating peptide.

In a third configuration, a functional group may be attached to the molecular scaffold itself. Examples of functional groups are as for the preceding configuration.

First Configuration

According to a first aspect of the first configuration of the invention, therefore, there is provided a method for providing a multispecific peptide ligand comprising a polypeptide covalently linked to a molecular scaffold at three or more amino acid residues and capable of binding to two or more separate targets, comprising the steps of:

(a) providing a first repertoire of polypeptides, each polypeptide comprising two or more reactive groups capable of covalent linkage to a molecular scaffold, and at least one loop which comprises a sequence of two or more amino acids subtended between two of said reactive groups;
(b) providing a second repertoire of polypeptides as described in (a);
(c) joining at least one loop of one or more members of the first repertoire to at least one loop of one or more members of the second repertoire to form at least one polypeptide comprising two loops, and
(d) conjugating the composite polypeptide(s) to a molecular scaffold at at least three amino acid positions.

The invention therefore provides for the preparation of a multispecific molecule by joining together parts of different molecules which are responsible for binding to different targets. These are the loops subtended between the attachment points to the molecular scaffold, which are defined by the reactive groups. Preferably, said first and second repertoires are screened for binding to said first and second targets before being combined to form the third repertoire.

Screening against first and second targets may be done in several formats. For example, the first or second repertoires may be conjugated to molecular scaffolds for the screening. Alternatively, particularly in the case of single-loop repertoires, the members may be internally cross-linked by allowing the reactive groups to pair, for instance through disulphide bonding.

As will be apparent, several permutations are possible. The first and second repertoires may comprise one, two or more peptide loops. Where more than one loop is present, selection for binding against the first or second target will not distinguish between cooperative binding involving more than one loop and individual binding by a single loop. Therefore, isolation of a loop from a molecule in the first or second repertoires does not guarantee that the isolated loop was sufficient for target binding, or that any such binding ability will be transferred to a target molecule. If the first and second repertoires comprise a single loop, it is more likely that this loop is sufficient for target binding and that this ability will be transferred to a hybrid molecule.

In one embodiment, therefore, the members of said first and/or second repertoires are conjugated to a molecular scaffold to form a single polypeptide loop. The use of single loops increases the probability that binding activity will be transferred when joining loops to those from another repertoire to create a multispecific polypeptide.

However, where the first and/or second repertoires are polypeptides comprising two or more loops, such loops may be isolated from the polypeptide and combined with single loops from polypeptides of another repertoire. In such an instance, a part of the polypeptide members corresponding to a single one of said polypeptide loops is joined to at least one loop of a polypeptide of the second repertoire. In certain instances, the entire polypeptide may be joined to another polypeptide from another repertoire, as described further below.

In one embodiment, the first and second repertoires are combined to form a third repertoire, which is screened for binding to the first and second targets. The first and second repertoires may be pre-screened against said targets individually, or may be naïve. Preferably, one of the repertoires is pre-screened; the other may be naïve.

In one embodiment, there is provided a method for providing a multispecific peptide ligand comprising a polypeptide covalently linked to a molecular scaffold at three or more amino acid residues and capable of binding to two or more separate targets, comprising the steps of:

(a) providing a first repertoire of polypeptides;
(b) conjugating said polypeptides to a molecular scaffold which binds to the polypeptides at two or more amino acid residues, to form a first repertoire of polypeptide conjugates;
(c) screening said first repertoire for binding against a first target, and selecting members of the first repertoire which bind to the first target;
(d) repeating steps (a) to (c) with a second repertoire of polypeptides, yielding a second repertoire of polypeptide conjugates which bind to a second target;
(e) isolating loops from members of said first and said second repertoires, and combining them to form a third repertoire of polypeptide conjugates, wherein the polypeptides are bound to the molecular scaffold at at least three amino acids, and selecting molecules capable of binding both to the first and the second target.

The transfer of binding ability from molecules containing two loops to a hybrid molecule containing only one of those loops can be inefficient. As with other embodiments, therefore, an efficient screening capability is highly desirable. Screening may be carried out by analysis of individual molecules. Such methods are provided in WO 2004/077062 and WO 2006/078161. Screening of individual compounds or small sets of compounds is tedious and can be expensive if large numbers of compounds are analyzed. The number of compounds that can be assayed with screening assays generally does not exceed several thousands.

In a preferred embodiment, the repertoires of polypeptides are provided in the form of a nucleic acid library, and incorporated as part of a genetic display system. Applicable systems include phage display, bacterial display, yeast display, ribosome or polysome display, mRNA display and in vitro expression in artificial microcapsules. The preferred technique is phage display using a filamentous bacteriophage.

Preferably, the polypeptide conjugate of the invention is dual specific, and comprises only two loops. Several such polypeptide conjugates may be incorporated together into the same protein. For example two such polypeptide conjugates of the same specificity can be linked together, for instance N-terminal to C-terminal, increasing the avidity of the ligand for its targets. Alternatively, in another embodiment a plurality of dual specific polypeptide conjugates are combined to form a multimer. For example, two different dual specific polypeptide conjugates are combined to create a tetra-specific molecule. Alternatively, three or more polypeptide conjugates, which may be the same or different, can be combined to form multispecific ligands.

In one embodiment multivalent complexes may be constructed by linking together the molecular scaffolds. This is discussed further below.

The first and the second targets are different. They may be, or be part of, polypeptides, proteins or nucleic acids, which may be naturally occurring or synthetic. The target may be an epitope, and such epitopes may be on the same or different molecules.

One skilled in the art will appreciate that the choice of target molecule is large and varied. They may be for instance human or animal proteins, cytokines, cytokine receptors, enzymes co-factors for enzymes or DNA binding proteins. Suitable cytokines and growth factors include but are not limited to: ApoE, Apo-SAA, BDNF, Cardiotrophin-1, EGF, EGF receptor, ENA78, Eotaxin, Eotaxin-2, Exodus-2, FGF-acidic, FGF-basic, fibroblast growth factor-10, FLT3 ligand, Fractalkine (CX3C), GDNF, G-CSF, GM-CSF, GF-I, insulin, IFNy, IGF-I, IGF-II, IL-Ia, IL-1 (3, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-17a, IL-17c, IL-17d, IL-17e, IL-17f, IL-18 (IGIF), IL-21, IL-22, IL-23, IL-31, IL-32, IL-33, IL-34, Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a. a.), MDC (69 a. a.), MCP-1 (MCAF), MCP-2, MCP-3, MCP-4, MDC (67 a. a.), MDC (69 a. a.), MIG, MIP-Ia, MIP-1p, MIP-3a, MIP3, MIP-4, myeloid progenitor inhibitor factor-1 (MPIF-1), NAP-2, Neurturin, Nerve growth factor, P-NGF, NT-3, NT-4, Oncostatin M, PDGF-AA, PDGF-AB, PDGF-BB, PF-4, RANTES, SDFIa, SDFIp, SCF, SCGF, stem cell factor (SCF), TARC, TGF-α, TGF-β, TGF-2, TGF-3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3 and HER 4; Cytokine receptors include receptors for the foregoing cytokines. Chemokine targets include CC chemokine ligands CCL21/6Ckine, CCL12/MCP-5, CCL6/C10, CCL22/MDC, CCL14/HCC-1/HCC-3, CCL3L1/MIP-1 alpha Isoform LD78 beta, CCL23/Ck beta 8-1, CCL3/MIP-1 alpha, CCL28, CCL4L1/LAG-1, CCL27/CTACK, CCL4/MIP-1 beta, CCL24/Eotaxin-2/MPIF-2, CCL15/MIP-1 delta, CCL26-like/Eotaxin-3-like, CCL9/10/MIP-1 gamma, CCL26/Eotaxin-3, CCL19/MIP-3 beta, CCL11/Eotaxin, CCL20/MIP-3 alpha, CCL14a/HCC-1, CCL23/MPIF-1, CCL14b/HCC-3, CCL18/PARC, CCL16/HCC-4, CCL5/RANTES, CCL1/1-309/TCA-3, TAFA1/FAM19A1, MCK-2, TAFA5/FAM19A5, CCL2/JE/MCP-1, TAFA3/FAM19A3, CCL8/MCP-2, TAFA4/FAM19A4, CCL7/MCP-3/MARC, CCL17/TARC, CCL13/MCP-4 and CCL25/TECK; chemokine receptors include CCR1, CCR7, CCR2, CCR8, CCR3, CCR9, CCR4, CCR10, CCR5, CCRL2/LCCR/CRAM-A/B and CCR6; CXC chemokine ligands include CXCL13/BLC/BCA-1, CXCL10/IP-10/CRG-2, CXCL14/BRAK, LIX, CXCL16, CXCL15/Lungkine, CXCL5/ENA-78, CXCL9/MIG, CXCL6/GCP-2, CXCL7/NAP-2, CXCL1/2/3/GRO, CXCL4/PF4, CXCL1/GRO alpha/KC/CINC-1, CXCL12/SDF-1 alpha, CXCL2/GRO beta/MIP-2/CINC-3, CXCL12/SDF-1 beta, CXCL3/GRO gamma/CINC-2/DCIP-1, CXCL12/SDF-1, CXCL11/1-TAC, CXCL7/Thymus Chemokine-1 and CXCL8/IL-8; CXC chemokine receptors include CXCR3, CXCR7/RDC-1, CXCR4, CXCR1/IL-8 RA, CXCR5, CXCR2/IL-8 RB and CXCR6; TNF Superfamily ligands include 4-1BB Ligand/TNFSF9, LIGHT/TNFSF14, APRIL/TNFSF13, Lymphotoxin, BAFF/BLyS/TNFSF13B, Lymphotoxin beta/TNFSF3, CD27 Ligand/TNFSF7, OX40 Ligand/TNFSF4, CD30 Ligand/TNFSF8, TL1A/TNFSF15, CD40 Ligand/TNFSF5, TNF-alpha/TNFSF1A, EDA (pan), TNF-beta/TNFSF1B, EDA-A1/Ectodysplasin A1, TRAIL/TNFSF10, EDA-A2, TRANCE/TNFSF11, Fas Ligand/TNFSF6, TWEAK/TNFSF12 and GITR Ligand/TNFSF18; TNF Superfamily receptors include 4-1BB/TNFRSF9/CD137, NGF R/TNFRSF16, BAFF R/TNFRSF13C, Osteoprotegerin/TNFRSF11B, BCMA/TNFRSF17, OX40/TNFRSF4, CD27/TNFRSF7, RANK/TNFRSF11A, CD30/TNFRSF8, RELT/TNFRSF19L, CD40/TNFRSF5, TACI/TNFRSF13B, DcR3/TNFRSF6B, TNFRH3/TNFRSF26, DcTRAIL R1/TNFRSF23, TNF RI/TNFRSF1A, DcTRAIL R2/TNFRSF22, TNF RII/TNFRSF1B, DR3/TNFRSF25, TRAIL R1/TNFRSF10A, DR6/TNFRSF21, TRAIL R2/TNFRSF10B, EDAR, TRAIL R3/TNFRSF10C, Fas/TNFRSF6/CD95, TRAIL R4/TNFRSF10D, GITR/TNFRSF18, TROY/TNFRSF19, HVEM/TNFRSF14, TWEAK R/TNFRSF12, Lymphotoxin beta R/TNFRSF3 and XEDAR; Toll-Like Receptors including TLR-1, TLR-2, TLR-3, TLR-4, TLR-5, TLR-6, TLR-7, TLR-8 and TLR-9; enzymes, including Cathepsin A, Cathepsin B, Cathepsin C, Cathepsin D, Cathepsin E, Cathepsin F, MMP 1, MMP2, MMP 3, MMP 7, MMP 8, MMP 9, MMP 10, MMP 11, MMP 12, MMP 13, MMP 14, MMP 15, MMP 16, MMP 17, MMP 19, MMP 20, MMP 21, MMP 23A, MMP 23B, MMP 26, MMP 27, MMP 28, urokinase, kallikreins, including KLK1, KLK2, KLK3, KLK4, KLK5, KLK6, KLK7, KLK8, KLK9, KLK10, KLK11, KLK12, KLK13, KLK14 and KLK15; components of the complement system; Intracellular signalling molecules and transcription factors; p53; and MDM2.

Targets may also be large plasma proteins, such as serum albumins, as set forth below.

It will be appreciated that this list is by no means exhaustive.

Targets may also be large plasma proteins, such as serum albumins, as set forth below.

It will be appreciated that this list is by no means exhaustive. Where the polypeptide conjugate binds to two epitopes (on the same or different targets), the target molecules may be selected from this list.

The targets may compete for binding to the polypeptide conjugate, such that they cannot both bind simultaneously. Alternatively, they may both bind simultaneously, such that the polypeptide conjugate bridges the targets. In such an embodiment, the third repertoire may be screened against both first and second targets simultaneously.

In a second aspect, the present invention provides a multispecific polypeptide conjugate comprising a peptide ligand covalently linked to a molecular scaffold. The conjugate according to the invention binds to at least two targets. Advantageously, the conjugate is obtainable by a method set forth above.

Advantageously, the dual specific polypeptide conjugate may comprise a first binding function capable of binding a target molecule, and a second binding function capable of binding a molecule or group which extends the half-life of the conjugate in vivo. For example, the molecule or group may be a bulky agent, such as HSA or a cell matrix protein. In one embodiment, the dual specific conjugate may be capable of binding the target molecule only on displacement of the half-life enhancing molecule or group. Thus, for example, a dual specific conjugate is maintained in circulation in the bloodstream of a subject by a bulky molecule such as HSA. When a target molecule is encountered, competition between the binding functions of the dual specific conjugate results in displacement of the HSA and binding of the target.

In a third aspect, the first configuration of the present invention provides one or more nucleic acid molecules encoding at least a dual-specific conjugate as herein defined.

The nucleic acid may further encode a signal sequence for export of the polypeptides from a host cell upon expression and may be fused with a surface component of a filamentous bacteriophage particle (or other component of a genetic display system) upon expression.

In a further aspect the present invention provides a vector comprising nucleic acid according to the present invention.

In a yet further aspect, the present invention provides a host cell transfected with a vector according to the present invention. The DNA vectors can be phage genomes; although, as set forth below, the present inventors have solved the problems inherent in phage display of peptides conjugated to molecular scaffolds, the chemical processing involved can affect infectivity of phage. Thus, where infectivity has been compromised, it may be preferable to transfect phage DNA into cells.

Expression from such a vector may be configured to produce, for example on the surface of a bacteriophage particle, variable domains for selection. This allows selection of displayed variable regions and thus selection of dual-specific conjugates using the method of the present invention.

Second Configuration

In accordance with the second configuration of the present invention, additional binding or functional activities may be attached to the N or C terminus of the peptide of a peptide covalently linked to a molecular scaffold. Therefore, the invention provides a peptide ligand comprising a polypeptide covalently linked to a molecular scaffold, conjugated to one or more functional groups.

The functional group is, for example, selected from the group consisting of: a group capable of binding to a molecule which extends the half-life of the peptide ligand in vivo, and a molecule which extends the half-life of the peptide ligand in vivo. Such a molecule can be, for instance, HSA or a cell matrix protein, and the group capable of binding to a molecule which extends the half-life of the peptide ligand in vivo is an antibody or antibody fragment specific for HSA or a cell matrix protein.

In one embodiment, the functional group is a binding molecule, selected from the group consisting of a second peptide ligand comprising a polypeptide covalently linked to a molecular scaffold, and an antibody or antibody fragment. Joining peptide ligands comprising a polypeptide covalently linked to a molecular scaffold provides an alternative means to create dual specific molecules, in which peptide ligands having desired specificity are joined together—preferably N terminus to C terminus—to form a multispecific molecule. 2, 3, 4, 5 or more peptide ligands may be joined together in this way. The specificities of any two or more of these ligands may be the same or different; if they are the same, a multivalent binding structure will be formed, which has increased avidity for the target compared to univalent binding molecules. The molecular scaffolds, moreover, may be the same or different, and may subtend the same or different numbers of loops.

The functional group can moreover be an effector group, for example an antibody Fc region.

Attachments to the N or C terminus may be made prior to binding of the peptide to a molecular scaffold, or afterwards. Thus, the peptide may be produced (synthetically, or by expression of nucleic acid) with an N or C terminal polypeptide group already in place. Preferably, however, the addition to the N or C terminus takes place after the peptide has been combined with the molecular backbone to form a conjugate. Advantageously, therefore, a group capable of binding to the desired functional group is attached to the peptide, to permit later attachment of the functional group itself. For example, Fluorenylmethyloxycarbonyl chloride can be used to introduce the Fmoc protective group at the N-terminus of the polypeptide. Fmoc binds to serum albumins including HSA with high affinity, and Fmoc-Trp or FMOC-Lys bind with an increased affinity. As shown for instance in Example 3, the peptide can be synthesised with the Fmoc protecting group left on, and then coupled with the scaffold through the cysteines. The Fmoc group confers human serum albumin binding function to the bicyclic peptide. Alternatively, as described in Example 6, a conjugate of the peptide with the scaffold can be made, and then modified at the N-terminus, for example with the amine- and sulfhydryl-reactive linker N-e-maleimidocaproyloxy)succinimide ester (EMCS). Via this linker the peptide conjugate can be linked to other polypeptides, for example an antibody Fc fragment.

The binding function may be another peptide bound to a molecular scaffold, creating a multimer; another binding protein, including an antibody or antibody fragment; or any other desired entity, including serum albumin or an effector group, such as an antibody Fc region.

Third Configuration

In the third configuration, additional binding or functional activities are bound directly to the molecular scaffold.

Advantageously, the molecular scaffold comprises a reactive group to which the additional activities can be bound. Preferably, this group is orthogonal with respect to the other reactive groups on the molecular scaffold, to avoid interaction with the peptide. In one embodiment, the reactive group may be protected, and deprotected when necessary to conjugate the additional activities.

Accordingly, the invention provides a method for preparing a peptide ligand comprising a polypeptide covalently linked to a molecular scaffold, conjugated to one or more binding or functional groups, comprising the steps of
(a) producing the polypeptide;
(b) conjugating it with the molecular scaffold; and
(c) attaching said one or more functional groups to the molecular scaffold.

Common Aspects

Certain aspects of the present invention are applicable to every configuration thereof. For example, the invention further provides a kit comprising at least a dual-specific peptide ligand according to the present invention.

In a further aspect, the present invention provides a composition comprising a dual specific peptide ligand, obtainable by a method of the present invention, and a pharmaceutically acceptable carrier, diluent or excipient.

Moreover, the present invention provides a method for the treatment of disease using a dual-specific peptide ligand or a composition according to the present invention.

In one embodiment of the invention the disease is cancer. For instance a bridging dual specific peptide ligand may be used to recruit cytotoxic T-cells to a cancer marker, or to bind to two different targets on the surface of a cancer cell, thereby increasing the affinity or specificity of binding to the cell surface. Alternatively if the binding of one target displaces the other, such antibodies might be used to release a drug on binding of a cancer cell surface marker.

In a further aspect, the present invention provides a method for the diagnosis, including diagnosis of disease using a dual-specific peptide ligand, or a composition according to the present invention. Thus in general the binding of an analyte to a dual specific peptide ligand may be exploited to displace an agent, which leads to the generation of a signal on displacement. For example, binding of analyte (second target) can displace an enzyme (first target) bound to the peptide ligand providing the basis for a binding assay, especially if the enzyme is held to the peptide ligand through its active site.

A particular advantage of the polypeptide conjugates of the invention are smaller than multispecific binding agents of the prior art. Typically, such a ligand has a molecular weight of less than 5000 Dalton; preferably less than 4000 Dalton; and preferably less than 3000 Dalton. It will be understood that a multispecific ligand constructed by "daisy-chaining" peptide ligands as described in the second configuration of the invention will possess a higher molecular weight. Moreover, peptide ligands bound to molecules such as HSA will have a much higher molecular weight.

The small size of the ligands results from the use of small molecular scaffolds, typically 500 Dalton in mass. The peptide itself is preferably less than 27 amino acids in length, as measured between the N-terminal and C-terminal attachment points which attach it to the molecular scaffold. Further peptides may, of course, be present or be attached outside of the attachment points, lengthening the peptide structure. Each loop of the polypeptide is preferably between 0 and 9 amino acids in length, measured between adjacent attachment points. Advantageously, the loops in any peptide ligand are independently 3, 4, 5, 6, 7, 8 or 9 amino acids in length.

DETAILED DESCRIPTION OF THE INVENTION

Figure 1:
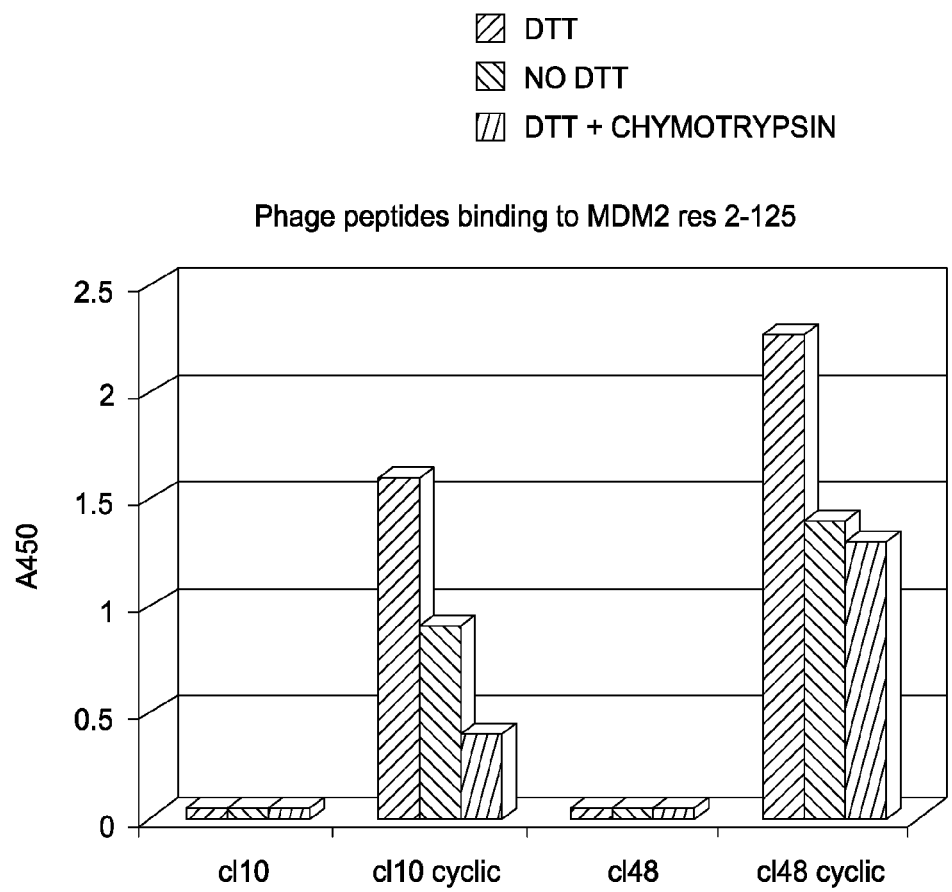
FIG. 1 shows binding of phage clones 10 and 48 (Example 1) to MDM2 as cyclic conjugates or unconjugated peptides, without pre-treatment with DTT, and with pre-treatment with DTT, and with pre-treatment with DTT followed by chymotrypsin.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

A peptide ligand, as referred to herein, refers to a peptide covalently bound to a molecular scaffold. Typically, such peptides comprise two or more reactive groups which are capable of forming covalent bonds to the scaffold, and a sequence subtended between said reactive groups which is referred to as the loop sequence, since it forms a loop when the peptide is bound to the scaffold.

The reactive groups are groups capable of forming a covalent bond with the molecular scaffold. Typically, the reactive groups are present on amino acid side chains on the peptide. Preferred are amino-containing groups such as cysteine, lysine and selenocysteine.

Multispecificity is the ability to bind to two or more targets. Typically, binding peptides are capable of binding to a single target, such as an epitope in the case of an antibody, due to their conformational properties. However, peptides can be developed which can bind to two or more targets; dual specific antibodies, for example, as known in the art as referred to above. In the present invention, the peptide ligands are capable of binding to two or more targets and are therefore multispecific. Preferably, they bind to two targets, and are dual specific. The binding may be independent, which would mean that the binding sites for the targets on the peptide are not structurally hindered by the binding of one or other of the targets. In this case both targets can be bound independently. More generally it is expected that the binding of one target will at least partially impede the binding of the other.

Multispecific peptides can be formed by joining together individual loops of peptide ligands which bind to individual targets. The loops which are joined together may be adjacent lops, or may be separated by a third loop, or even further loops. Where the loops are placed directly adjacent in the multispecific peptide, it is preferred that one of the reactive groups defining one of the loops is omitted, to avoid effective duplication of reactive groups at one position.

A target is a molecule or part thereof to which the peptide ligands bind. Typically, the target will be analogous to an epitope, and thus may take the form of different epitopes on the same molecule, or different epitopes on different molecules. Where the targets are on the same molecule, the use of a dual specific ligand will increase the avidity of the ligand for the molecule, and may impart other properties due to cross-linking the molecule or the occupation of defined functional parts of the molecule.

The molecular scaffold is any molecule which is able to connect the peptide at multiple points to impart one or more structural features to the peptide. It is not a cross-linker, in that it does not merely replace a disulphide bond; instead, it provides two or more attachment points for the peptide. Preferably, the molecular scaffold comprises at least three attachment points for the peptide, referred to as scaffold reactive groups. These groups are capable of reacting to the reactive groups on the peptide to form a covalent bond. Preferred structures for molecular scaffolds are described below.

A repertoire is a collection of variants, in this case polypeptide variants, which differ in their sequence. Typically, the location and nature of the reactive groups will not vary, but the sequences forming the loops between them can be randomised.

Screening for binding activity (or any other desired activity) is conducted according to methods well known in the art, for instance from phage display technology. For example, targets immobilised to a solid phase can be used to identify and isolate binding members of a repertoire. Screening allows selection of members of a repertoire according to desired characteristics.

The term library refers to a mixture of heterogeneous polypeptides or nucleic acids. The library is composed of members, each of which has a single polypeptide or nucleic acid sequence. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members.

Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

Preferably, a library of nucleic acids encodes a repertoire of polypeptides. Each nucleic acid member of the library preferably has a sequence related to one or more other members of the library. By related sequence is meant an amino acid sequence having at least 50% identity, suitably at least 60% identity, suitably at least 70% identity, suitably at least 80% identity, suitably at least 90% identity, suitably at least 95% identity, suitably at least 98% identity, suitably at least 99% identity to at least one other member of the library. Identity is suitably judged across a contiguous segment of at least 3 amino acids, suitably at least 4, 5, 6, 7, 8, 9 or 10 amino acids, suitably least 12 amino acids, suitably least 14 amino acids, suitably least 16 amino acids, suitably least 17 amino acids or the full length of the reference sequence.

A functional group, attached to a peptide ligand, is a group which, for example, mediates a further binding activity or permits the binding of an effector group. Thus, functional groups include antibodies and binding fragments thereof, further peptide ligands as described herein, chemical reactive groups, and the like.

An effector group is a group attached to the peptide ligand which has a specific activity. For instance, it may be a protein which increases the half life of the peptide ligand, such as human serum albumin (HSA). Effector groups also include drugs, such as cytotoxic drugs, immunoeffectors, such as antibody Fc regions, and compounds which conform to the following parameters: not more than 5 hydrogen bond donors (nitrogen or oxygen atoms with one or more hydrogen atoms); not more than 10 hydrogen bond acceptors (nitrogen or oxygen atoms); a molecular weight under 500 daltons; and an octanol-water partition coefficient log P of less than 5.

Multispecific Peptide Ligands

The peptide ligands according to the invention may be prepared by techniques known in the prior art, or described herein. The components of the ligands, especially the molecular scaffold and the polypeptide components, are known from Timmerman et al., 2005 ChemBioChem 6:821-824, as well as WO2004/077062, WO2006/078161 and WO2008/013454. The use of phage display to select polypeptides complexed with molecular scaffolds is described in Heinis et al., 2009, Nature Chemical Biology 5, 502-507, as well as our copending unpublished international patent application PCT/GB09/000,301. Each of these documents is incorporated herein by reference. Preferred methods for constructing multispecific molecules according to the invention, and the use of phage display, are described in more detail below.

In general, multispecific molecules according to the invention can be constructed by (a) fusing two loops originating from two individual monospecific peptide ligands; (b) fusing two entire monospecific peptide ligands; (c) attaching a binding group to a peptide ligand, at the N or C termini, or to the molecular scaffold; or (d) chemically attaching a functional group or an effector group directly to the peptide ligand, preferably on the molecular scaffold.

(A) Construction of Peptide Ligands
(i) Molecular Scaffold

The molecular scaffold is sometimes referred to as the 'molecular core' or 'connector compound'. Suitably, the molecular scaffold possesses molecular symmetry. Suitably, the molecular scaffold possesses three scaffold reactive groups and possesses threefold symmetry. This has the advantage of producing only a single reaction product. If the molecular scaffold is not a symmetric molecule, then multiple reaction products can be produced. This can lead to complications, or require that the desired isomer be separated from the other reaction products.

The preferred reactive group for conjugating the peptide to the molecular scaffold is cysteine. However, when there are three or more reactive groups for at least three discrete covalent bonds to the molecular scaffold, said reactive groups need not each be cysteines. For example, the three reactive groups may comprise one cysteine and two further suitable reactive groups, which might for example comprise lysine, selenocysteine or other(s). Most suitably all three reactive groups are cysteines.

In known techniques, at best a cross linking agent has been introduced or joined to the polypeptide such as a genetically encoded polypeptide. By contrast, the present invention provides a molecular scaffold for the multiple coordination of different parts of the same polypeptide.

Suitably the molecular scaffold may be a small molecule. Suitably the molecular scaffold is a small organic molecule.

Suitably the molecular scaffold may be, or may be based on, natural monomers such as nucleosides, sugars, or steroids. Suitably the molecular scaffold may comprise a short polymer of such entities, such as a dimer or a trimer.

Suitably the molecular scaffold is a compound of known toxicity, suitably of low toxicity. Examples of suitable compounds include cholesterols, nucleotides, steroids, or existing drugs such as tamazepam.

Suitably the molecular scaffold may be a macromolecule. Suitably the molecular scaffold is a macromolecule composed of amino acids, nucleotides or carbohydrates.

Suitably the molecular scaffold comprises reactive groups that are capable of reacting with functional group(s) of the polypeptide to form covalent bonds.

The molecular scaffold may comprise chemical groups as amines, thiols, alcohols, ketones, aldehydes, nitriles, carboxylic acids, esters, alkenes, alkynes, azides, anhydrides, succinimides, maleimides, alkyl halides and acyl halides.

Suitably the molecular scaffold may comprise or may consist of tris(bromomethyl)benzene, especially 1,3,5-Tris(bromomethyl)benzene ('TBMB'), or a derivative thereof.

Suitably the molecular scaffold has a 3-fold rotational symmetry such that reaction of three functional groups of the polypeptide with the molecular scaffold generates a single product isomer.

In some embodiments the molecular scaffold may have a tetrahedral geometry such that reaction of four functional groups of the encoded polypeptide with the molecular scaffold generates not more than two product isomers.

A suitable molecular scaffold is 2,4,6-Tris(bromomethyl) mesitylene. It is similar to 1,3,5-Tris(bromomethyl)benzene but contains additionally three methyl groups attached to the benzene ring. This has the advantage that the additional methyl groups may form further contacts with the polypeptide and hence add additional structural constraint.

The molecular scaffold of the present invention is selected from either a small molecule or a macromolecular structure. The said molecular scaffold is composed of organic, inorganic or organic and inorganic components.

In a preferred embodiment, the molecular scaffold is a small organic molecule as for example a linear alkane. More suitably the molecular scaffold is a branched alkane, a cyclic alkane, a polycyclic alkane, an aromate, a heterocyclic alkane or a heterocyclic aromate, which offer the advantage of being less flexible (i.e. more rigid). Most suitably the molecular scaffold comprises a benzylic group.

In another embodiment, the molecular scaffold is selected from a macromolecular structure as for example a polypeptide, a polynucleotide or a polysaccharide.

The molecular scaffold of the invention contains chemical groups that allow functional groups of the polypeptide of the encoded library of the invention to form covalent links with the molecular scaffold. Said chemical groups are selected from a wide range of functionalities including amines, thiols, alcohols, ketones, aldehydes, nitriles, carboxylic acids, esters, alkenes, alkynes, anhydrides, succinimides, maleimides, azides, alkyl halides and acyl halides.

(ii) Polypeptide

The reactive groups of the encoded polypeptides are suitably provided by side chains of natural or non-natural amino acids. The reactive groups of the encoded polypeptides are suitably selected from thiol groups, amino groups, carboxyl groups, guanidinium groups, phenolic groups or hydroxyl groups. The reactive groups of the encoded polypeptides may suitably be selected from azide, keto-carbonyl, alkyne, vinyl, or aryl halide groups. The reactive groups of the encoded polypeptides for linking to a molecular scaffold may suitably be the amino or carboxy termini of the polypeptide.

In some embodiments each of the reactive groups of the polypeptide for linking to a molecular scaffold are of the same type. For example, each reactive group may be a cysteine residue.

In some embodiments the reactive groups for linking to a molecular scaffold may comprise two or more different types, or may comprise three or more different types. For example, the reactive groups may comprise two cysteine residues and one lysine residue, or may comprise one cysteine residue, one lysine residue and one N-terminal amine.

Cysteine is the most suitable amino acid because it has the advantage that its reactivity is most different from all other amino acids. Scaffold reactive groups that could be used on the molecular scaffold to react with thiol groups of cysteines are alkyl halides (or also named halogenoalkanes or haloalkanes). Examples are bromomethylbenzene (the scaffold reactive group exemplified by TBMB) or iodoacetamide. Other scaffold reactive groups that are used to couple selectively compounds to cysteines in proteins are maleimides. Examples of maleimides which may be used as molecular scaffolds in the invention include: tris-(2-maleimidoethyl)amine, tris-(2-maleimidoethyl)benzene, tris-(maleimido)benzene. Selenocysteine is also a natural amino acid which has a similar reactivity to cysteine and can be used for the same reactions. Thus, wherever cysteine is mentioned, it is typically acceptable to substitute selenocysteine unless the context suggests otherwise. Most suitably cysteine is used.

Lysines (and primary amines of the N-terminus of peptides) are also suited as reactive groups to modify peptides on phage by linking to a molecular scaffold. However, they are more abundant in phage proteins than cysteines and there is a higher risk that phage particles might become cross-linked or that they might lose their infectivity. Nevertheless, it has been found that lysines are especially useful in intramolecular reactions (e.g. when a molecular scaffold is already linked to the phage peptide) to form a second or consecutive linkage with the molecular scaffold. In this case the molecular scaffold reacts preferentially with lysines of the displayed peptide (in particular lysines that are in close proximity). Scaffold reactive groups that react selectively with primary amines are succinimides, aldehydes or alkyl halides. In the bromomethyl group that is used in a number of the accompanying examples, the electrons of the benzene ring can stabilize the cationic transition state. This particular aryl halide is therefore 100-1000 times more reactive than alkyl halides. Examples of succinimides for use as molecular scaffold include tris-(succinimidyl aminotriacetate), 1,3,5-Benzenetriacetic acid. Examples of aldehydes for use as molecular scaffold include Triformylmethane. Examples of alkyl halides for use as molecular scaffold include 1,3,5-Tris(bromomethyl)-2,4,6-trimethylbenzene, 1,3,5-Tris(bromomethyl)benzene, 1,3,5-Tris(bromomethyl)-2,4,6-triethylbenzene.

In some embodiments, molecular linkers or modifications may be added to (or to create) reactive groups of the encoded polypeptides before attachment of the molecular scaffold wherein said linkers or modifications are capable to react with the molecular scaffold.

The amino acids with reactive groups for linking to a molecular scaffold may be located at any suitable positions within the encoded polypeptide. In order to influence the particular structures or loops created, the positions of the amino acids having the reactive groups may be varied by the skilled operator, e.g. by manipulation of the nucleic acid encoding the polypeptide in order to mutate the polypeptide produced.

Each of the amino acids of the encoded polypeptide may be a target for mutagenesis (e.g. restricted variance mutagenesis) according to the needs of the skilled worker or the purpose to which the invention is being applied. Clearly at least three reactive groups for bonding to the molecular scaffold are required on the polypeptide of interest. Amino acids other than those required for bonding to the molecular scaffold may be freely varied according to operator needs and are termed 'variable amino acids'. Said variable amino acids of the encoded polypeptide (e.g. polypeptide library member(s)) may be randomised, partially randomised, or constant.

The polypeptide comprises a molecular scaffold binding segment. This is the region to which the molecular scaffold is attached. Suitably the commentary regarding reactive groups on the polypeptide is applied to this binding segment. Suitably the molecular scaffold binding segment of the polypeptide comprises 1 to 27 amino acid residues, suitably 5 to 20 amino acid residues. Suitably the molecular scaffold binding segment of the polypeptide comprises fewer than 10 amino acids. This has the advantage of imposing further conformational constraint onto the polypeptide segment when it is attached to the molecular scaffold.

The polypeptide suitably comprises the sequence $AC(X)_6C(X)_6CG$ (SEQ ID NO. 1), wherein X stands for a random natural amino acid, A for alanine, C for cysteine and G for glycine.

The polypeptide suitably comprises the sequence $(X)lY(X)mY(X)nY(X)o$ (SEQ ID No. 26), wherein Y represents an amino acid with a reactive group, X represents a random amino acid, m and n are numbers between 1 and 20 defining the length of intervening polypeptide segments and l and o are numbers between 0 and 20 defining the length of the flanking polypeptide segments.

In some embodiments, the peptide ligand of the invention may comprise a polypeptide with the sequence $AC(X)_6C(X)_6CG$ (SEQ ID NO. 1). In one embodiment, a library member or peptide ligand of the invention may comprise a mesitylene molecular scaffold and a polypeptide with the sequence $AC(X)_6C(X)_6CG$ (SEQ ID NO. 1), wherein the polypeptide is tethered to the exo-cyclic methyl groups of the molecular scaffold via the cysteine residues of the polypeptide forming three thioether bonds therewith, and wherein X stands for an amino acid, (suitably a natural amino acid), A for alanine, C for cysteine and G for glycine. The use of mesitylene scaffolds introduces a degree of flexibility into the structure of the peptide ligand.

(iii) Reactive Groups of the Polypeptide

The molecular scaffold of the invention may be bonded to the polypeptide via functional or reactive groups on the polypeptide. These are typically formed from the side chains of particular amino acids found in the polypeptide polymer. Such reactive groups may be a cysteine side chain, a lysine side chain, or an N-terminal amine group or any other suitable reactive group.

Suitably at least one reactive group is a cysteine group. Groups such as lysine or the N-terminal amines are typically not reactive enough to bond with the molecular scaffold on their own within a convenient time frame. However, once the molecular scaffold has been attracted or bonded to at least one cysteine, then ordinary reaction kinetics mean that the lysine or amine bonds can rapidly and stably form thereafter. For this reason, suitably at least one of the reactive groups is a cysteine group.

If reactive groups on the polypeptide other than cysteine/lysine/amine groups are desired, then a different molecular scaffold may be chosen in order to pair with the particular functional reactive groups of choice on the polypeptide.

Suitably cysteine, lysine or amine groups are used as the functional or reactive groups on the polypeptide of interest.

Suitably at least three covalent bonds are formed between the molecular scaffold and the polypeptide of interest.

In some embodiments, four bonds or even more may be formed between the molecular scaffold and the polypeptide of interest. However, if more than four bonds are used, then typically the product mixtures formed become increasingly complex and may hinder the subsequent uses or applications. For this reason, three bonds or four bonds between the molecular scaffold and the polypeptide of interest are preferred. In any embodiment, molecular symmetry of the molecular scaffold is preferred. Most preferred are molecular scaffolds having three functional or reactive groups. Most preferred are molecular scaffolds having three fold molecular symmetry.

The reactive groups of the genetically encoded polypeptides of the invention are capable of forming covalent bonds to the molecular scaffold/molecular core. Reactive groups are specific groups of atoms within either natural or non-natural amino acids. Preferentially, reactive groups with a distinctive chemical reactivity are used to link the polypeptide the molecular scaffold to form the complex of the invention. The usage of said distinctive reactive groups allows bonding of the molecular scaffold/molecular core exclusively to the designated reactive groups of the polypeptide but not to other chemical groups of either the diversity elements of the polypeptide, the nucleic acid or other components of the complex.

Suitable reactive groups of natural amino acids are the thiol group of cysteine, the amino group of lysine, the carboxyl group of aspartate or glutamate, the guanidinium group of arginine, the phenolic group of tyrosine or the hydroxyl group of serine. Non-natural amino acids can provide a wide range of reactive groups including an azide, a keto-carbonyl, an alkyne, a vinyl, or an aryl halide group. The amino and carboxyl group of the termini of the polypeptide can also serve as reactive groups to form covalent bonds to a molecular scaffold/molecular core.

The encoded polypeptides of the invention suitably contain at least three reactive groups. Said polypeptides can also contain four or more reactive groups. The more reactive groups are used, the more diversity segments can be tethered to the molecular scaffold/molecular core. However, the linkage of excessive numbers of reactive groups to a molecular scaffold/molecular core is not recommended since this can lead to an unmanageable number of product isomers. Suitably three, four or five covalent bonds to a molecular scaffold are used; most suitably three or four covalent bonds; most suitably three covalent bonds.

In a preferred embodiment, encoded polypeptides with three reactive groups are generated. Reaction of said polypeptides with a molecular scaffold/molecular core having a three-fold rotational symmetry generates a single product isomer. The generation of a single product isomer is favourable for several reasons. The nucleic acids of the compound libraries encode only the primary sequences of the polypeptide but not the isomeric state of the molecules that are formed upon reaction of the encoded polypeptide with the molecular core. If only one product isomer can be formed, the assignment of the nucleic acid to the product isomer is clearly defined. If multiple product isomers are formed, the nucleic acid can not give information about the nature of the product isomer that was isolated in a screening or selection process. The formation of a single product isomer is also advantageous if a specific member of a library of the invention is synthesized. In this case, the chemical reaction of the polypeptide with the molecular scaffold yields a single product isomer rather than a mixture of isomers.

In another embodiment of the invention, encoded polypeptides with four reactive groups are generated. Reaction of said polypeptides with a molecular scaffold/molecular core having a tetrahedral symmetry generates two product isomers. Even though the two different product isomers are encoded by one and the same nucleic acid ('genetic code'), the isomeric nature of the isolated isomer can be determined by chemically synthesizing both isomers, separating the two isomers and testing both isomers for binding to a target ligand.

In one embodiment of the invention, at least one of the reactive groups of the polypeptides is orthogonal to the remaining reactive groups. The use of orthogonal reactive groups allows the directing of said orthogonal reactive groups to specific sites of the molecular core. Linking strategies involving orthogonal reactive groups may be used to limit the number of product isomers formed. In other words, by choosing distinct or different reactive groups for one or more of the at least three bonds to those chosen for the remainder of the at least three bonds, a particular order of bonding or directing of specific reactive groups of the polypeptide to specific positions on the molecular scaffold may be usefully achieved.

In another embodiment, the reactive groups of the encoded polypeptide of the invention are reacted with molecular linkers wherein said linkers are capable to react with a molecular scaffold so that the linker will intervene between the molecular scaffold and the polypeptide in the final bonded state.

Suitable amino acids of the members of the genetically encoded combinatorial chemical libraries can be replaced by any natural or non-natural amino acid. Excluded from these exchangeable amino acids are the ones harbouring functional groups for cross-linking the polypeptides to a molecular core. A group of adjacent amino acids that can be varied is defined as a polypeptide segment. The size of a single polypeptide segment suitably ranges from 1 to 20 amino acids. The polypeptide segments have either random sequences, constant sequences or sequences with random and constant amino acids. The amino acids with reactive groups are either located in defined or random positions within the encoded polypeptide of the invention.

In one embodiment, the polypeptide segments that are bounded by two amino acids harbouring reactive groups for bonding with a molecular scaffold/molecular core are short amino acid sequences of 10 or fewer amino acids. Reaction of said encoded polypeptide sequences with a molecular core generates library members with high conformational constraint. Conformational constrained ligands are generally more specific and have higher binding affinities. The conformational constraint can also protect the ligands from proteolytic degradation for example in bodily fluids.

In one embodiment, an encoded polypeptide with three reactive groups has the sequence $(X)_l Y(X)_m Y(X)_n Y(X)_o$ (SEQ ID No. 26), wherein Y represents an amino acid with a reactive group, X represents a random amino acid, m and n are numbers between 1 and 20 defining the length of intervening polypeptide segments and l and o are numbers between 0 and 20 defining the length of the flanking polypeptide segments.

In a preferred embodiment, an encoded polypeptide library of the invention has the sequence $AC(X)_6 C(X)_6 CG$ (SEQ ID NO. 1), wherein A represents alanine, C represents cysteine, X represents a random natural amino acid and G represents glycine.

Alternatives to thiol-mediated conjugations can be used to attach the molecular scaffold to the peptide via covalent interactions. Alternatively these techniques may be used in modification or attachment of further moieties (such as small molecules of interest which are distinct from the molecular scaffold) to the polypeptide after they have been selected or isolated according to the present invention—in this embodiment then clearly the attachment need not be covalent and may embrace non-covalent attachment. These methods may be used instead of (or in combination with) the thiol mediated methods by producing phage that display proteins and peptides bearing unnatural amino acids with the requisite chemical reactive groups, in combination small molecules that bear the complementary reactive group, or by incorporating the unnatural amino acids into a chemically or recombinantly synthesised polypeptide when the molecule is being made after the selection/isolation phase.

The unnatural amino acids incorporated into peptides and proteins on phage may include 1) a ketone reactive group (as found in para or meta acetyl-phenylalanine) that can be specifically reacted with hydrazines, hydroxylamines and their derivatives (Addition of the keto reactive group to the genetic code of *Escherichia coli*. Wang L, Zhang Z, Brock A, Schultz P G. Proc Natl Acad Sci USA. 2003 Jan. 7; 100(1):56-61; Bioorg Med Chem. Lett. 2006 Oct. 15; 16(20):5356-9. Genetic introduction of a diketone-containing amino acid into proteins. Zeng H, Xie J, Schultz P G), 2) azides (as found in p-azido-phenylalanine) that can be reacted with alkynes via copper catalysed "click chemistry" or strain promoted (3+2) cyloadditions to form the corresponding triazoles (Addition of p-azido-L-phenylalanine to the genetic code of *Escherichia coli*. Chin J W, Santoro S W, Martin A B, King D S, Wang L, Schultz P G. J Am Chem. Soc. 2002 Aug. 7; 124(31):9026-7; Adding amino acids with novel reactivity to the genetic code of *Saccharomyces cerevisiae*. Deiters A, Cropp T A, Mukherji M, Chin J W, Anderson J C, Schultz P G. J Am Chem. Soc. 2003 Oct. 1; 125(39):11782-3), or azides that can be reacted with aryl phosphines, via a Staudinger ligation (Selective Staudinger modification of proteins containing p-azidophenylalanine. Tsao M L, Tian F, Schultz P G. Chembiochem. 2005 December; 6(12):2147-9), to form the corresponding amides, 4) Alkynes that can be reacted with azides to form the corresponding triazole (In vivo incorporation of an alkyne into proteins in *Escherichia coli*. Deiters A, Schultz P G. Bioorg Med Chem. Lett. 2005 Mar. 1; 15(5):1521-4), 5) Boronic acids (boronates) than can be specifically reacted with compounds containing more than one appropriately spaced hydroxyl group or undergo palladium mediated coupling with halogenated compounds (Angew Chem Int Ed Engl. 2008; 47(43):8220-3. A genetically encoded boronate-containing amino acid., Brustad E, Bushey M L, Lee J W, Groff D, Liu W, Schultz P G), 6) Metal chelating amino acids, including those bearing bipyridyls, that can specifically co-ordinate a metal ion (Angew Chem Int Ed Engl. 2007; 46(48):9239-42. A genetically encoded bidentate, metal-binding amino acid. Xie J, Liu W, Schultz P G).

Unnatural amino acids may be incorporated into proteins and peptides displayed on phage by transforming *E. coli* with plasmids or combinations of plasmids bearing: 1) the orthogonal aminoacyl-tRNA synthetase and tRNA that direct the incorporation of the unnatural amino acid in response to a codon, 2) The phage DNA or phagemid plasmid altered to contain the selected codon at the site of unnatural amino acid incorporation (Proc Natl Acad Sci USA. 2008 Nov. 18; 105(46):17688-93. Protein evolution with an expanded genetic code. Liu C C, Mack A V, Tsao M L, Mills J H, Lee H S, Choe H, Farzan M, Schultz P G, Smider V V; A phage display system with unnatural amino acids. Tian F, Tsao M L, Schultz P G. J Am Chem. Soc. 2004 Dec. 15; 126(49):15962-3). The orthogonal aminoacyl-tRNA synthetase and tRNA may be derived from the *Methancoccus janaschii* tyrosyl pair or a synthetase (Addition of a photocrosslinking amino acid to the genetic code of *Escherichia coli*. Chin J W, Martin A B, King D S, Wang L, Schultz P G. Proc Natl Acad Sci USA. 2002 Aug. 20; 99(17):11020-4) and tRNA pair that naturally incorporates pyrrolysine (Multistep engineering of pyrrolysyl-tRNA synthetase to genetically encode N(epsilon)-(o-azidobenzyloxycarbonyl) lysine for site-specific protein modification. Yanagisawa T, Ishii R, Fukunaga R, Kobayashi T, Sakamoto K, Yokoyama S. Chem. Biol. 2008 Nov. 24; 15(11):1187-97; Genetically encoding N(epsilon)-acetyllysine in recombinant proteins. Neumann H, Peak-Chew S Y, Chin J W. Nat Chem. Biol. 2008 April; 4(4):232-4. Epub 2008 Feb. 17). The codon for incorporation may be the amber codon (UAG) another stop codon (UGA, or UAA), alternatively it may be a four base codon. The aminoacyl-tRNA synthetase and tRNA may be produced from existing vectors, including the pBK series of vectors, pSUP (Efficient incorporation of unnatural amino acids into proteins in *Escherichia coli*. Ryu Y, Schultz P G. Nat. Methods. 2006 April; 3(4):263-5) vectors and pDULE vectors (Nat. Methods. 2005 May; 2(5):377-84. Photo-cross-linking interacting proteins with a genetically encoded benzophenone. Farrell I S, Toroney R, Hazen J L, Mehl R A, Chin J W). The *E. coli* strain used will express the F' pilus (generally via a tra operon). When amber suppression is used the *E. coli* strain will not itself contain an active amber suppressor tRNA gene. The amino acid will be added to the growth media, preferably at a final concentration of 1 mM or greater. Efficiency of amino acid incorporation may be enhanced by using an expression construct with an orthogonal ribosome binding site and translating the gene with ribo-X (Evolved orthogonal ribosomes enhance the efficiency of synthetic genetic code expansion. Wang K, Neumann H, Peak-Chew S Y, Chin J W. Nat. Biotechnol. 2007 July; 25(7):770-7). This may allow efficient multi-site incorporation of the unnatural amino acid providing multiple sites of attachment to the ligand.

(iv) Combination of Loops to Form Multispecific Molecules

Loops from peptide ligands, or repertoires of peptide ligands, are advantageously combined by sequencing and de novo synthesis of a polypeptide incorporating the combined loops. Alternatively, nucleic acids encoding such polypeptides can be synthesised.

Where repertoires are to be combined, particularly single loop repertoires, the nucleic acids encoding the repertoires are advantageously digested and re-ligated, to form a novel repertoire having different combinations of loops from the constituent repertoires. Phage vectors can include polylinkers and other sites for restriction enzymes which can provide unique points for cutting and relegation the vectors, to create the desired multispecific peptide ligands. Methods for manipulating phage libraries are well known in respect of antibodies, and can be applied in the present case also.

(v) Post Attachment Modification

In some embodiments the polypeptide-molecular scaffold complex may be modified at a time following attachment.

Protease Cleavage

In some embodiments, the polypeptide elements of the invention are proteolytically cleaved once they are tethered to a molecular scaffold/molecular core. The cleavage generates ligands having discrete peptide fragments tethered to a molecular scaffold/molecular core. This approach can facilitate the combination of loops from individual peptide ligands, to form multispecific peptide ligands according to the invention.

For example, one or more amide bonds of the polypeptide may be proteolytically cleaved after tethering the polypeptide to the molecular core. This has the advantage of creating short polypeptides, each joined to the molecular scaffold by at least one covalent bond, but which present different molecular structures which are retained in a complex comprising the nucleic acid encoding the parent polypeptide. The polypeptide cleavage is suitably catalysed by any suitable means known in the art such as controlled hydrolysis or more suitably enzymatic cleavage by a suitable protease. The protease may be any suitable protease but is preferably a protease with a specific polypeptide recognition sequence or motif. This advantageously leads to production of more defined and/or more predictable polypeptide cleavage products. Indeed, in this embodiment, protease recognition sequences may be systematically added or removed from the polypeptide, for example by manipulation of the nucleic acid(s) encoding it. This advantageously provides a greater degree of control and permits greater diversity to be produced in the molecules displayed according to the present invention. Most suitably the polypeptide comprises at least one protease recognition site. Suitably each said cleavage site is comprised within amino acid sequence(s) in between reactive groups on the polypeptide used for covalent bonding to the molecular scaffold. Suitably each said recognition site is comprised within amino acid sequence(s) in between reactive groups on the polypeptide used for covalent bonding to the molecular scaffold.

The peptide loops are suitably cleaved with a protease that recognizes and processes polypeptides at specific amino acid positions such as trypsin (arginine or lysine in P1 position) or thermolysin (aliphatic side chains in P1 position). The enzyme is used at a concentration that allows efficient processing of the peptide loops of the displayed molecule but spares the phage particle. The optimal conditions can vary depending on the length of the polypeptide loops and on the protease used. Trypsin for example is typically used at 200 nM in TBS-Ca buffer (25 mM Tris HCl/137 mM NaCl/1 mM $CaCl_2$, pH 7.4) for 10 min at 10° C. A whole range of proteases that are suitable to modify displayed polypeptides but that spare the phage are described in Kristensen, P. and Winter, G. (Proteolytic selection for protein folding using filamentous bacteriophages; Fold Des. 1998; 3(5):321-8). The enzymatic processing of peptide on phage may be a 'partial proteolysis' since it can not be excluded that a limited number of phage coat proteins are cleaved. Thus in optimisation of the conditions, the best balance between maximised cleavage of the target and maximum sparing of the phage particles is suitably chosen.

Suitably the polypeptide comprises at least one such proteolytic cleavage site. Suitably the polypeptide comprises at least two such proteolytic cleavage sites.

Suitably the polypeptide comprises at least three such proteolytic cleavage sites.

In each such proteolysis embodiment, suitably the said protease site(s) are located within the polypeptide loops subtended by the molecular scaffold. This has the advantage that the molecular scaffold is retained on the complex, as otherwise the polypeptide-molecular scaffold complex may be separated from the nucleic acid encoding the polypeptide, which is undesirable for the majority of applications of the invention.

The use of short loops (short being e.g. 6 amino acid residues or less) may compromise the ability of some proteases to cleave within the loops. In this case it may be desirable to select longer loops which are likely to be more accessible to the protease. Furthermore after cleavage of the loops by endoprotease, it may be desirable to cut back the loops further with other endoproteases, or indeed by exoproteases, such as carboxypeptidases or aminopeptidases.

When the polypeptide comprises more than one such protease site, suitably each of the sites occurs between two covalent bonds made between the polypeptide and the molecular scaffold. Multiple cleavage sites may occur between bonds if necessary.

Protease Resistance

In another embodiment, the polypeptides may be resistant to protease cleavage. In general, tightly folded polypeptide structures are more resistant to proteases, since the protease cannot physically access the polypeptide to cleave it. Therefore, manipulation of the scaffold and scaffold attachment in the peptide ligand can modulate protease sensitivity, by influencing the folding of the polypeptide loop.

As indicated in the preceding section, a protease step can be introduced to cleave accessible sites within loops attached to a chemical scaffold. If a repertoire of peptide conjugates is displayed on phage, this leads to peptides each joined to the chemical scaffold by at least one covalent bond, but retained in a complex comprising the nucleic acid encoding the parent polypeptide. The treatment of the chemically modified phage with protease before selection with antigen is expected to give rise to phage bearing peptide conjugates with cleaved loop(s), and also to phage bearing peptide conjugates with uncleaved loop(s) due to lack of a cleavage site, or otherwise being resistant to cleavage. It is possible to distinguish these species if one binds to antigen and the other does not, by comparing the binding of the selected phage clones to target antigen before and after protease treatment. Thus the species with cleaved loops will be expected to bind after protease treatment, but not before; whereas the protease-resistant species will be expected to bind both before and after treatment. Note that if a conjugate binds with both cleaved and uncleaved loops (as with PK15 after kallikrein cleavage; see Heinis et al, 2009), it may be incorrectly identified as protease resistant. This shows the importance of using a direct method for checking cleavage, for example by synthesizing the peptide conjugates chemically, and checking for evidence of cleavage, for example by mass spectrometry.

If cleaved loop conjugates are preferred to protease resistant conjugates, it will be advantageous to treat the chemically modified phage repertoire with protease before the first round of selection, and to continue to use the same protease, or one with a common cut-site, in subsequent rounds. However protease resistant conjugates may alternatively be desired. Such peptides may be useful for oral administration to survive the gut proteases, or those otherwise subject to proteolytic attack in the blood, tissues or cells. In this case, a first round of selection without protease, followed by a subsequent round of selection with protease, should favour the selection of the resistant species.

The use of protease has further utility during the selection process. For example, some unformed loops (linear segments of sequence) may be present in the libraries because (a) errors in the synthesis of the nucleotides have failed to encode a required cysteine residue, or (b) a required cysteine residue has made a disulphide bond to free cysteine in solution (perhaps due to inadequate reduction or re-oxidation), or has reacted in an irreversible manner (for example is oxidized to cysteic acid, or one of the required cysteines has reacted with a different molecule of the scaffold to the others). As linear segments of sequence are more susceptible to protease attack than loops, then, subject to a cleavage site being present, it may be possible to avoid such binders using protease.

A protease step (in the presence of reducing agent) is also advantageous to eliminate loops that have formed via disulphides between the required cysteines rather than through the chemical scaffold. This may be expected if there is inadequate reduction (or subsequent reoxidation) of the cysteines on the phages. For this reason we used degassed buffers during the chemical cross-linking step; we also kept low levels of the reducing agent (TCEP) during the reaction with TBMB to maintain the reducing environment. Nevertheless, after the first round of selection, we found many sequences that included four cysteine residues (the three required cysteine residues, and a further cysteine residue in the loop), for example PEP21 (CFNSEWSCLQSCSNC) (SEQ ID NO. 2). Such extra cysteines are expected to be present in the peptide repertoires, as the synthetic nucleotide library includes random codons (NNK diversity: where N represents a 25% mix each of adenine, thymine, guanine, and cytosine nucleotides, and K represents a 50% mix each of thymine and guanine nucleotides). Under some conditions, for example if there is inadequate reduction, or incomplete reaction of the required cysteines with the chemical scaffold (perhaps due to competing reactions for the scaffold by amino groups or water), an extra cysteine may be expected, under oxidising conditions, to form disulphide loops with one of the three required cysteines. Alternatively an extra cysteine may react with the scaffold, leaving two of the required cysteines to form disulphide-closed loops.

Whatever the exact mechanism behind their generation, such disulphide-closed loops may compete with the scaffold-closed loops, and predominate. It should be possible to reduce the frequency of the extra cysteines by using synthetic nucleotide libraries built from triplets, rather than monomers, so avoiding cysteine codons in the loops; and/or to undertake the selections in the presence of reducing agent, so as to open the disulphide-closed loops. More conveniently we have found that the treatment of the chemically modified phage repertoires with protease in the presence of reducing agent (such as dithiothreitol or TCEP), so as to open and then cleave the loops, helps to minimise the contribution of such species.

In one embodiment, therefore, the peptide ligands of the invention are substantially protease resistant. Exposing the peptide ligands to cleavage after selection against the target will favour the identification of binding peptide ligands which are resistant to protease cleavage. It cannot be entirely excluded that certain peptide ligands will retain the ability to bind to the target after cleavage; however, the incidence of such ligands will be low. The invention therefore provides a method for selecting a peptide ligand having increased protease resistance, comprising the steps of:

(a) providing a first repertoire of polypeptides;
(b) conjugating said polypeptides to a molecular scaffold which binds to the polypeptides at two or more amino acid residues, to form a repertoire of polypeptide conjugates;
(c) screening said repertoire for binding against a target, and selecting members of the first repertoire which bind to the target;
(d) optionally, treating the selected repertoire with reducing agent
(e) treating the repertoire with a protease; and
(f) further screening said repertoire for binding to the target.

In another embodiment, the peptide ligands of the invention are substantially cleaved by protease. The protease step is included before the screening of repertoire, which will favour the identification of peptide ligands which bind to the target in cleaved form. The invention therefore provides a method for selecting a peptide ligand that is cleaved by protease, comprising the steps of:

(a) providing a first repertoire of polypeptides;
(b) conjugating said polypeptides to a molecular scaffold which binds to the polypeptides at two or more amino acid residues, to form a repertoire of polypeptide conjugates;
(c) optionally treating the repertoire with reducing agent
(d) treating the repertoire with a protease; and
(e) screening said repertoire for binding against a target, and selecting members of the first repertoire which, after treatment with protease, bind to the target.

A screen for protease resistance can simply take the form of limited digestion with a protease to identify those members of the repertoire in which the binding is sensitive to proteases, or requires the action of proteases. Most desirable will be to use a protease that is active under the conditions in which the bicyclic peptide will be used, for example in the presence of serum.

(vi) Attachment of Effector Groups and Functional Groups

Effector and/or functional groups can be attached to the N or C termini of the polypeptide, or to the molecular scaffold, as described above.

Suitable effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further preferred embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of *Drosophila* (Antennapedia), e.g. as described in Chen and Harrison, Biochemical Society Transactions (2007) Volume 35, part 4, p821 "Cell-penetrating peptides in drug development: enabling intracellular targets" and "Intracellular delivery of large molecules and small peptides by cell penetrating peptides" by Gupta et al. in Advanced Drug Discovery Reviews (2004) Volume 57 9637. Examples of short peptides which have been shown to be efficient at translocation through plasma membranes include the 16 amino acid penetratin peptide from *Drosophila* Antennapedia protein (Derossi et al (1994) J. Biol. Chem. Volume 269 p10444 "The third helix of the Antennapedia homeodomain translocates through biological membranes"), the 18 amino acid 'model amphipathic peptide' (Oehlke et al (1998) Biochim Biophys Acts Volume 1414 p127 "Cellular uptake of an alpha-helical amphipathic model peptide with the potential to deliver polar compounds into the cell interior non-endocytically") and arginine rich regions of the HIV TAT protein. Non peptidic approaches include the use of small molecule mimics or SMOCs that can be easily attached to biomolecules (Okuyama et al (2007) Nature Methods Volume 4 p153 'Small-molecule mimics of an a-helix for efficient transport of proteins into cells'. Other chemical strategies to add guanidinium groups to molecules also enhance cell penetration (Elson-Scwab et al (2007) J Biol Chem Volume 282 p13585 "Guanidinylated Neomcyin Delivers Large Bioactive Cargo into cells through a heparin Sulphate Dependent Pathway"). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half life of the peptide ligand in vivo may be used.

RGD peptides, which bind to integrins which are present on many cells, may also be incorporated.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half life in the range 12 to 60 hours. In a further embodiment, it will have at half-life of a day or more. In a further embodiment still, it will be in the range 12 to 26 hours.

Functional groups include drugs, such as cytotoxic agents for cancer therapy. These include Alkylating agents such as Cisplatin and carboplatin, as well as oxaliplatin, mechlorethamine, cyclophosphamide, chlorambucil, ifosfamide; Anti-metabolites including purine analogs azathioprine and mercaptopurine)) or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include Antitumour antibiotics which include the immunosuppressant dactinomycin (which is used in kidney transplantations), doxorubicin, epirubicin, bleomycin and others.

Possible effector groups also include enzymes, for instance such as carboxypeptidase G2 for use in enzyme/prodrug therapy, where the peptide ligand replaces antibodies in ADEPT.

(vii) Synthesis

It should be noted that once the polypeptide of interest is isolated or identified according to the present invention, then its subsequent synthesis may be simplified wherever possible. For example, the sequence of the polypeptide of interest may be determined, and it may be manufactured synthetically by standard techniques followed by reaction with a molecular scaffold in vitro. When this is performed, standard chemistry may be used since there is no longer any need to preserve the functionality or integrity of the genetically encoded carrier particle. This enables the rapid large scale preparation of soluble material for further downstream experiments or validation. In this regard, large scale preparation of the candidates or leads identified by the methods of the present invention could be accomplished using conventional chemistry such as that disclosed in Timmerman et al.

Thus, the invention also relates to manufacture of polypeptides or conjugates selected as set out herein, wherein the manufacture comprises optional further steps as explained below. Most suitably these steps are carried out on the end product polypeptide/conjugate made by chemical synthesis, rather than on the phage.

Optionally amino acid residues in the polypeptide of interest may be substituted when manufacturing a conjugate or complex e.g. after the initial isolation/identification step.

Peptides can also be extended, to incorporate for example another loop and therefore introduce multiple specificities.

To extend the peptide, it may simply be extended chemically at its N-terminus or C-terminus using standard solid phase or solution phase chemistry. Standard protein chemistry may be used to introduce an activatable N- or C-terminus. Alternatively additions may be made by fragment condensation or native chemical ligation e.g. as described in (Dawson P E, Muir T W, Clark-Lewis I, Kent, S B H. 1994. Synthesis of Proteins by Native Chemical Ligation. Science 266:776-779), or by enzymes, for example using subtiligase as described in (Subtiligase: a tool for semisynthesis of proteins Chang T K, Jackson D Y, Burnier J P, Wells J A Proc Natl Acad Sci USA. 1994 Dec. 20; 91(26):12544-8 or in Bioorganic & Medicinal Chemistry Letters Tags for labelling protein N-termini with subtiligase for proteomics Volume 18, Issue 22, 15 Nov. 2008, Pages 6000-6003 Tags for labeling protein N-termini with subtiligase for proteomics; Hikari A. I. Yoshihara, Sami Mahrus and James A. Wells).

Alternatively, the peptides may be extended or modified by further conjugation through disulphide bonds. This has the additional advantage of allowing the first and second peptide to dissociate from each other once within the reducing environment of the cell. In this case, the molecular scaffold (eg. TBMB) could be added during the chemical synthesis of the first peptide so as to react with the three cysteine groups; a further cysteine could then be appended to the N-terminus of the first peptide, so that this cysteine only reacted with a free cysteine of the second peptide.

Similar techniques apply equally to the synthesis/coupling of two bicyclic and bispecific macrocycles, potentially creating a tetraspecific molecule.

Furthermore, addition of other functional groups or effector groups may be accomplished in the same manner, using appropriate chemistry, coupling at the N- or C-termini or via side chains. Suitably the coupling is conducted in such a manner that it does not block the activity of either entity.

(B) Repertoires of Peptide Ligands (i) Construction of Libraries

Libraries intended for selection may be constructed using techniques known in the art, for example as set forth in WO2004/077062, or biological systems, including phage vector systems as described herein. Other vector systems are known in the art, and include other phage (for instance, phage lambda), bacterial plasmid expression vectors, eukaryotic cell-based expression vectors, including yeast vectors, and the like.

Non-biological systems such as those set forth in WO2004/077062 are based on conventional chemical screening approaches. They are simple, but lack the power of biological systems since it is impossible, or at least impracticably onerous, to screen large libraries of peptide ligands. However, they are useful where, for instance, only a small number of peptide ligands needs to be screened. Screening by such individual assays, however, may be time-consuming and the number of unique molecules that can be tested for binding to a specific target generally does not exceed $10^6$ chemical entities.

In contrast, biological screening or selection methods generally allow the sampling of a much larger number of different molecules. Thus biological methods are more suitably used in application of the invention. In biological procedures, molecules are assayed in a single reaction vessel and the ones with favourable properties (i.e. binding) are physically separated from inactive molecules. Selection strategies are available that allow to generate and assay simultaneously more than $10^{13}$ individual compounds. Examples for powerful affinity selection techniques are phage display, ribosome display, mRNA display, yeast display, bacterial display or RNA/DNA aptamer methods. These biological in vitro selection methods have in common that ligand repertoires are encoded by DNA or RNA. They allow the propagation and the identification of selected ligands by sequencing. Phage display technology has for example been used for the isolation of antibodies with very high binding affinities to virtually any target.

When using a biological system, once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected before mutagenesis and additional rounds of selection are performed.

Such approaches are particularly indicated for affinity maturation of peptide ligands as described herein. For example, a first and a second repertoire of peptide ligands which bind to a first and second target may be combined, and the resulting third repertoire subjected to affinity maturation by mutagenesis of the nucleic acid library members which encode the repertoire.

Mutagenesis of nucleic acid sequences encoding structurally optimised polypeptides is carried out by standard molecular methods. Of particular use is the polymerase chain reaction, or PCR, (Mullis and Faloona (1987) Methods Enzymol., 155: 335, herein incorporated by reference). PCR, which uses multiple cycles of DNA replication catalysed by a thermostable, DNA-dependent DNA polymerase to amplify the target sequence of interest, is well known in the art. The construction of various antibody libraries has been discussed in Winter et al. (1994) Ann. Rev. Immunology 12, 433-55, and references cited therein.

PCR is performed using template DNA (at least 1fg; more usefully, 1-1000 ng) and at least 25 pmol of oligonucleotide primers; it may be advantageous to use a larger amount of primer when the primer pool is heavily heterogeneous, as each sequence is represented by only a small fraction of the molecules of the pool, and amounts become limiting in the later amplification cycles. A typical reaction mixture includes: 2 µl of DNA, 25 pmol of oligonucleotide primer, 2.5 µl of 10×PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. 1. Mineral oil is overlaid and the PCR is performed using a programmable thermal cycler. The length and temperature of each step of a PCR cycle, as well as the number of cycles, is adjusted in accordance to the stringency requirements in effect. Annealing temperature and timing are determined both by the efficiency with which a primer is expected to anneal to a template and the degree of mismatch that is to be tolerated; obviously, when nucleic acid molecules are simultaneously amplified and mutagenized, mismatch is required, at least in the first round of synthesis. The ability to optimise the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1-5 minutes, depending on the length of the amplified product). Final extension is generally for 4 minutes at 72 C, and may be followed by an indefinite (0-24 hour) step at 4° C.

Alternatively, given the short chain lengths of the polypeptides according to the invention, the variants are preferably synthesised de novo and inserted into suitable expression vectors. Peptide synthesis can be carried out by standard techniques known in the art, as described above. Automated peptide synthesisers are widely available, such as the Applied Biosystems ABI 433 (Applied Biosystems, Foster City, Calif., USA)

(ii) Genetically Encoded Diversity

The polypeptides of interest are suitably genetically encoded. This offers the advantage of enhanced diversity together with ease of handling. An example of a genetically encoded polypeptide library is a mRNA display library. Another example is a replicable genetic display package (rgdp) library such as a phage display library. Suitably, the polypeptides of interest are genetically encoded as a phage display library.

Thus, suitably the complex of the invention comprises a replicable genetic display package (rgdp) such as a phage particle. In these embodiments, suitably the nucleic acid is comprised by the phage genome. In these embodiments, suitably the polypeptide is comprised by the phage coat.

In some embodiments, the invention may be used to produce a genetically encoded combinatorial library of polypeptides which are generated by translating a number of nucleic acids into corresponding polypeptides and linking molecules of said molecular scaffold to said polypeptides.

The genetically encoded combinatorial library of polypeptides may be generated by phage display, yeast display, ribosome display, bacterial display or mRNA display.

Suitably the genetically encoded combinatorial library of polypeptides is generated by phage display. In phage display embodiments, suitably the polypeptides are displayed on phage according to established techniques such as described below. Most suitably such display is accomplished by fusion of the polypeptide of interest to an engineered gene permitting external display of the polypeptide of interest; suitably said engineered gene comprises an engineered gene 9 (p9 or gene IX), gene 8 (gene VIII), gene 7 (p7 or gene VII), gene 6 (p6 or gene VI) or gene 3 (p3 or gene III) of the phage. These proteins offer the advantage that they contain fewer or no cysteines that can react with molecular scaffolds such as TBMB and produce side products. For p6, it is advantageous to mutate cysteine 84 to serine. The cysteines in p7 and p9 are most likely buried and therefore may not necessarily need to be mutated to remove them. p8 offers the advantage that it does not contain a cysteine residue. Thus, more suitably said engineered gene comprises an engineered gene 8 (gene VIII), gene 6 (gene VI) or gene 3 (gene III) of the phage.

Most suitably such display is accomplished by fusion of the polypeptide of interest to an engineered gene 3 protein lacking cysteine residues in domain 1 and 2. This fusion may be accomplished by any suitable technique known in the art such as by manipulation of the nucleic acid encoding the phage gene III protein to change the codons encoding cysteine to codon(s) encoding other amino acid(s), and by inserting a nucleic acid sequence encoding the polypeptide into the gene III coding sequence in frame so that it is displayed as a gene III fusion protein on the outside of the phage particle.

It is a benefit of the invention that the resulting engineered gene(s) leave the phage infective i.e. capable of infection and propagation. Even when the engineered gene is a gene other than gene 3, (such as gene 6 or gene 8), it may still be desirable to engineer gene 3 to remove one or more of the cysteine residue(s) (such as all of the cysteine residues).

In a preferred embodiment, the genetically encoded polypeptides of the invention are generated by translating a nucleic acid and linking the generated polypeptide to said code. The linkage of phenotype with the genotype allows propagating or decoding the encoded ligand repertoires. Various techniques are available to link the polypeptide to its polynucleotide code. The techniques include phage display, ribosome display, mRNA display, yeast display and bacterial display and others. Encoded polypeptide repertoires comprising up to 10exp13 individual members have been generated with said methods. The number of individual ligands that can be generated according to the invention outperforms clearly the number of individual molecules that are generally assayed in conventional screens.

In a preferred embodiment, phage display technology is used to genetically encode polypeptides of the invention. Phage display is a method in which the gene of a polypeptide is fused to the gene of a phage coat protein. When phage are produced in a bacterial cell, the polypeptide is expressed as a fusion of the coat protein. Upon assembly of a phage particle the polypeptide is displayed on the surface of the phage. By contacting a phage repertoire with an immobilized antigen some phage remain bound to the antigen while others are removed by washing. The phage can be eluted and propagated. The DNA encoding the polypeptide of selected phage can be sequenced. Phage display can be used to encode more than $10^{10}$ individual polypeptides. A favourable aspect of phage display is that the genetic code, a single stranded DNA is packed in a coat. The coat may protect the DNA from reaction with the molecular core.

In another preferred embodiment, the polypeptide library of the invention is displayed on phage as a gene 3 protein fusion. Each phage particle has about 3 to 5 copies of said phage coat protein. As a result of the display of multiple copies of the modified polypeptide, ligands with micromolar affinities (weak binders) can also be isolated in phage selections. Alternatively, phagemids are used to reduce the number of polypeptides per phage to avoid avidity effects and select ligands with higher affinities.

In another preferred embodiment, phage with modified coat proteins are used for encoding the polypeptide libraries of the invention. In particular, phage lacking or having a reduced number of a specific type of amino acid in coat proteins are used. Using said coat proteins can be advantageous when the molecular core is reactive towards said specific type of amino acid. This is explicitly the case when the reactive groups of the displayed polypeptide for cross-linking a molecular core are natural amino acids and the same type of natural amino acid is present at a surface exposed region in the phage coat. Using said phage with modified coat proteins can prevent cross-linking of phage particles through reaction of amino acids of multiple phage with the same molecular core. In addition, using said phage can reduce the cross-linkage of both, amino acid side chains of the reactive groups in the polypeptide and of phage coat protein to the same molecular core.

In yet another preferred embodiment, phage with a gene 3 protein lacking the cysteine residues of the disulfide bridges C7-C36, C46-C53, C188-C201 in domain 1 and 2 are used to display polypeptide libraries of the invention. A phage with mutations in said positions (C7C, C36I, C46I, C53V, C188V, C201A) and 14 additional mutations in the gene 3 protein to compensate for the reduced thermal stability (T13I, N15G, R29W, N39K, G55A, T56I, I60V, T101I, Q129H, N138G, L198P, F199L, S207L, D209Y) was generated by Schmidt F. X. and co-workers (Kather, I. et al., J. Mol. Biol., 2005). Phage without thiol groups in said minor coat protein are suited if one or more of the functional amino acids for cross-linking the polypeptide to a molecular core are cysteine residues. Removal of the cysteine residues in the phage coat protein prevents their interference with said bonding reaction between polypeptide and molecular scaffold.

This exemplary phage for application in the invention is now described in more detail.

The disulfide-free phage of FX Schmid (domains D1-D2) comprises fd phage derived from vector fCKCBS (Krebber, C., 1997, J. Mol. Biol.). The vector fCKCBS is based on a fd phage vector that is derived from the American Type Culture Collection (ATCC: 15669-B2).

The amino acid sequence of the domains 1 and 2 of p3 of the wild-type fd phage is publicly available, for example in the PubMed database. For ease of reference, an exemplary sequence is: AETVESCLAKPHTENSFTNVWKDDKTL-DRYANYEGCLWNATGVVVCTGDETQ-CYGTWVPIGLA IPENEGGGSEGGGSEGGGSEGGGT-KPPEYGDTPIPGYTYINPLDGTYPPGTEQNPA NPNPSLE ESQPLNTFMFQNNRFRNRQGALTVYTGT-VTQGTDPVKTYYQYTPVSSKAMYDAYWNGKFRDC AFHSGFNEDPFVCEYQGQSSDLPQPPVNAPSG (SEQ ID NO. 3)

```
                                                        (SEQ ID NO. 3)
AETVESCLAKPHTENSFTNVWKDDKTLDRYANYEGCLWNATGVVVCTGDE

TQCYGTWVPIGLAIPENEGGGSEGGGSEGGGSEGGGTKPPEYGDTPIPGY

TYINPLDGTYPPGTEQNPANPNPSLEESQPLNTFMFQNNRFRNRQGALTV

YTGTVTQGTDPVKTYYQYTPVSSKAMYDAYWNGKFRDCAFHSGFNEDPFV

CEYQGQSSDLPQPPVNAPSG
```

FX Schmid and co-workers had evolutionarily stabilized the p3 of this phage (Martin, A. and Schmid, F X., 2003, J. Mol. Biol.) by mutating 4 amino acids. In a consecutive work FX Schmid and co-workers had mutated 6 cysteines to eliminate the 3 disulfide-bridges and inserted additional mutations to compensate for the loss of stability (Kather, I. and Schmid F X., 2005, J. Mol. Biol.). In multiple evolutionary cycles they had generated clones 19, 20, 21, and 23 which have all a disulfide-free p3 with varying thermal stabilities.

The mutant 21 ('clone 21') can be made as described, or simply obtained from FX Schmid and co-workers. According to the publication of FX Schmid this clone contains the following mutations in the domains 1 and 2: C7S, T13I, N15G, R29W, C36I, N39K, C46I, C53V, G55A, T101I, Q129H, C188V, F199L, C201A, D209Y. In addition we found the following mutations in the domains 1 and 2 when we sequenced the clone and compared it to wild-type fd phage: P11S and P198L. Without wishing to be bound by theory it is assumed that these mutations were already present in the phage of vector fCKCBS.

The domains D1 and D2 of clone 21 have the following amino acid sequence:

```
                                                        (SEQ ID NO. 4)
AETVESSLAKSHIEGSFTNVWKDDKTLDWYANYEGILWKATGVVVITGDE

TQVYATWVPIGLAIPENEGGGSEGGGSEGGGSEGGGTKPPEYGDTPIPGY

IYINPLDGTYPPGTEQNPANPNPSLEESHPLNTFMFQNNRFRNRQGALTV

YTGTVTQGTDPVKTYYQYTPVSSKAMYDAYWNGKFRDVAFHSGFNEDLLV

AEYQGQSSYLPQPPVNAPSG
```

In one embodiment, screening may be performed by contacting a library of the invention with a target and isolating one or more library member(s) that bind to said target.

In another embodiment, individual members of said library are contacted with a target in a screen and members of said library that bind to said target are identified.

In another embodiment, members of said library are simultaneously contacted with a target and members of said library that bind to said target are selected.

The target(s) may be a peptide, a protein, a polysaccharide, a lipid, a DNA or a RNA.

The target may be a receptor, a receptor ligand, an enzyme, a hormone or a cytokine.

The target ligand may be a prokaryotic protein, a eukaryotic protein, or an archeal protein. More specifically the target ligand may be a mammalian protein or an insect protein or a bacterial protein or a fungal protein or a viral protein.

The target ligand may be an enzyme, such as a protease.

It should be noted that the invention also embraces library member(s) isolated from a screen according to the invention.

Suitably the screening method(s) of the invention further comprise the step of: manufacturing a quantity of the complex of the invention isolated as capable of binding to said targets.

The invention also relates to library members which are, or are capable of being, isolated by a screen according to the present invention, wherein said member is subsequently generated/manufactured without the further use of the nucleic acid which encoded said polypeptide when part of the complex of the invention. For example, the methods of the invention suitable further comprise the additional step of manufacturing a quantity of a polypeptide isolated or identified by a method of the invention by attaching the molecular scaffold to the polypeptide, wherein said polypeptide is recombinantly expressed or chemically synthesized. For example, when the polypeptide is recombinantly synthesised in this embodiment, the nucleic acid originally encoding it as part of a complex of the invention may no longer be directly present but may have been present in an intermediate step eg. PCR amplification or cloning of the original nucleic acid of the complex, leading to production of a template nucleic acid from which the polypeptide may be synthesised in this additional step.

The invention also relates to peptide ligands having more than two loops. For example, tricyclic polypeptides joined to a molecular scaffold can be created by joining the N- and C-termini of a bicyclic polypeptide joined to a molecular scaffold according to the present invention. In this manner, the joined N and C termini create a third loop, making a tricyclic polypeptide. This embodiment is suitably not carried out on phage, but is suitably carried out on a polypeptide—molecular scaffold conjugate of the invention. Joining the N- and C-termini is a matter of routine peptide chemistry. In case any guidance is needed, the C-terminus may be activated and/or the N- and C-termini may be extended for example to add a cysteine to each end and then join them by disulphide bonding. Alternatively the joining may be accomplished by use of a linker region incorporated into the N/C termini. Alternatively the N and C termini may be joined by a conventional peptide bond. Alternatively any other suitable means for joining the N and C termini may be employed, for example N-C-cyclization could be done by standard techniques, for example as disclosed in Linde et al. Peptide Science 90, 671-682 (2008) "Structure-activity relationship and metabolic stability studies of backbone cyclization and N-methylation of melanocortin peptides", or as in Hess et al. J. Med. Chem. 51, 1026-1034 (2008) "backbone cyclic peptidomimetic melanocortin-4 receptor agonist as a novel orally administered drug lead for treating obesity". One advantage of such tricyclic molecules is the avoidance of proteolytic degradation of the free ends, in particular by exoprotease action. Another advantage of a tricyclic polypeptide of this nature is that the third loop may be utilised for generally applicable functions such as BSA binding, cell entry or transportation effects, tagging or any other such use. It will be noted that this third loop will not typically be available for selection (because it is not produced on the phage but only on the polypeptide-molecular scaffold conjugate) and so its use for other such biological functions still advantageously leaves both loops 1 and 2 for selection/creation of specificity. Thus the invention also relates to such tricyclic polypeptides and their manufacture and uses.

The present invention provides further methods for contacting the genetically encoded compound libraries with a target ligand and for identifying ligands binding to said target ligand. The genetically encoded compound libraries are assayed by either screening or selection procedures.

In a screening procedure, individual members of the library are assayed. Multiple copies of an individual member of the library are for example incubated with a target ligand. The target ligand is immobilized before or after contacting the members of the library and unbound members are removed by washing. Bound ligands are for example detected in an enzyme linked immunosorbent assay (ELISA). The amino acid sequences of members of the library that bind to the target ligand are determined by sequencing of the genetic code.

In a selection procedure, multiple members of the encoded compound library are contacted with one or more targets. The targets are immobilized before or after contacting the members of the library and unbound members are removed by washing. The genetic code of bound ligands is sequenced. Selected ligands are alternatively propagated to perform further selection rounds.

In one embodiment of the invention, the compound libraries are encoded by phage display and selections are performed by phage panning.

(iii) Phage Purification

Any suitable means for purification of the phage may be used. Standard techniques may be applied in the present invention. For example, phage may be purified by filtration or by precipitation such as PEG precipitation; phage particles may be produced and purified by polyethylene-glycol (PEG) precipitation as described previously.

In case further guidance is needed, reference is made to Jespers et al (Protein Engineering Design and Selection 2004 17(10):709-713. Selection of optical biosensors from chemisynthetic antibody libraries.) Suitably phage may be purified as taught therein. The text of this publication is specifically incorporated herein by reference for the method of phage purification; in particular reference is made to the materials and methods section starting part way down the right-column at page 709 of Jespers et al.

Moreover, the phage may be purified as published by Marks et al J. Mol. Biol. vol 222 pp 581-597, which is specifically incorporated herein by reference for the particular description of how the phage production/purification is carried out.

In case any further guidance is needed, phage may be reduced and purified as follows. Approximately $5 \times 10^{12}$ phage particles are reacted with 1 mM dithiothreitol (DTT) for 30 min at room temperature, then PEG precipitated. After rinsing with water, the pellet is resuspended in 1 ml of reaction buffer (10 mM phosphate buffer, 1 mM EDTA, pH 7.8). The phage are then optionally reacted with 50 µl of 1.6 mM N-[(2-iodoacetoxy)ethyl]-N-methylamino-7-nitrobenz-2-oxa-1,3-diazole (NBDIA) (Molecular Probes) for 2 h at room temperature, or more suitably reacted with the molecular scaffold as described herein. The reaction is terminated by PEG precipitation of phage particles.

A yet still further way in which the phage may be produced/purified is as taught in Schreier and Cortese (A fast and simple method for sequencing DNA cloned in the single-stranded bacteriophage M13. Journal of molecular biology 129(1):169-72, 1979). This publication deals with the chain termination DNA sequencing procedure of Sanger et al. (1977), which requires single-stranded DNA as template. M13 phage DNA exists as a single strand and therefore every DNA sequence cloned in M13 can be easily obtained in this form. Schreier and Cortese show that M13 single-stranded DNA pure enough to be used as a template for sequence determination can be prepared by simple centrifugation of the phage particle and extraction with phenol. The Schreier and Cortese publication is specifically incorporated herein by reference for the method of purification of the phage. For the avoidance of doubt, the phenol extraction is not performed for making complexes according to the present invention since that is for the purpose of nucleic acid purification. Thus the phenol step of Schreier and Cortese is suitably omitted. The Schreier and Cortese method is followed only to the point of purified phage particles.

Thus there are myriad techniques well known in the art for purification of phage. In the context of the present invention such purification is used for the removal of reducing agent used to reduce the reactive groups in the polypeptide of interest for bonding to the molecular scaffold, particularly when such bonding is via cysteine residues.

Optionally, especially advantageous techniques for phage purification may be adopted as discussed in the reaction chemistry section below. It should be expressly noted that these techniques are not regarded as essential for the invention, but may represent especially helpful methods or even the best mode of making the phage particles of the invention. However, provided attention is paid to avoiding reoxidation of the reduced functional/reactive groups on the phage at the stage of removal of the reducing agent before attachment of the molecular scaffold then in principle any technique may be used to accomplish this. The filtration techniques described are effective but also more complicated than standard techniques so the operator will choose the technique best suited to their particular working of the invention.

(iv) Reaction Chemistry

Prior art technologies for modification of polypeptides have involved harsh chemistry and independent polypeptide modification reactions. By contrast, the present invention makes use of chemical conditions for the modification of polypeptides which advantageously retain the function and integrity of the genetically encoded element of the product. Specifically, when the genetically encoded element is a polypeptide displayed on the surface of a phage encoding it, the chemistry advantageously does not compromise the biological integrity of the phage. It is disclosed herein that there is a narrow window of conditions for which these chemical reactions can be enhanced or facilitated. In particular, as will be explained in more detail below, the solvents and temperatures used are important to an efficient reaction. Furthermore, the concentration of the reagents used are also instrumental in promoting the correct bonding, whilst ameliorating or eliminating cross linking or damaging of the polypeptide moieties which are being modified.

In particular, it is disclosed that the reduction of the cysteines in the polypeptide is required for the most efficient reaction. Clearly, the reducing agent used to chemically reduce those cysteines must be removed in order to perform the desired attachment. One known technique is to use dithiothreitol (DTT) or triscarboxyethylphosphine (TCEP) for reduction of the cysteines, and for the removal of the reducing agent to precipitate the particles such as the phage particles in a precipitation reaction. Such precipitation reactions typically involve 20% polyethylene glycol (PEG) together with 2.5 molar NaCl which leads to precipitation of the phage particles. However it is important to avoid re-oxidation. As will be disclosed in more detail below, the solutions are found in a range of strategies including the use of degassed buffer, the use of chelators in the reaction mixture, and the use of filtration in order to extract the particles, or the use of low concentrations of TCEP in the presence of TBMB.

Reaction conditions e.g. for attachment of the molecular scaffold to the polypeptide should be chosen carefully. Choice of conditions may vary depending upon the application to which the invention is being put. Particular care is required when the polypeptide is comprised by a phage particle. Guidance is provided throughout the specification and examples section.

Reaction conditions as reaction temperature, molecular scaffold concentration, solvent and/or pH should be chosen to allow efficient reaction of the reactive groups of the polypeptide with the molecular scaffold, but leave the nucleic acid encoding the polypeptide in a condition that allows to decode (e.g. to sequence) and/or propagate the isolated molecules (e.g. by PCR or by phage propagation or any other suitable technique). Moreover, the reaction conditions should leave the phage coat protein in a condition that allows it to propagate the phage.

Thiol groups of a phage encoded polypeptide may be reduced with reducing agent prior to molecular scaffold attachment. In such embodiments, in particular in phage display embodiments, or in particular when the reducing agent is TCEP, the excess of reducing agent is suitably removed by filtration, e.g. filtration of the phage.

In the present invention, reaction conditions are applied that on the one hand allow to efficiently link the encoded polypeptide to a molecular scaffold and on the other hand leave the appended nucleic acid (and phage coat proteins) in a condition that allows its propagation or decoding. Said reaction conditions are for example the reaction temperature, molecular scaffold concentration, solvent composition or pH.

In one embodiment of the present invention, thiol groups of cysteine residues are used as reactive groups to link polypeptides to a molecular core. For some chemical reactions, the thiol groups of the polypeptides need to be reduced. Thiol groups in phage displayed polypeptides are efficiently reduced by addition of a reducing agent as for example tris(carboxyethyl)phosphine (TCEP). Since an excess of reducing agent can interfere with the attachment reaction it is largely removed by filtration of the phage, or by PEG precipitation, although low concentrations (10 micromolar or less) may be desirable to maintain reducing conditions during the attachment reaction.

Re-oxidation of the thiol groups can be prevented by including TCEP in the reaction of the peptide with the molecular scaffold.

Re-oxidation of the thiol groups is suitably prevented by degassing of the reaction buffer.

Re-oxidation of the thiol groups is also suitably prevented by complex formation of metal ions by chelation, for example chelation with ethylenediaminetetraacetic acid (EDTA).

Most suitably re-oxidation of the thiol groups is prevented or inhibited by including TCEP in the reaction of the molecular scaffold, by chelation and by use of degassed buffers.

In one embodiment of the present invention, attachment of the polypeptide to the molecular scaffold is accomplished by reacting the reactive groups of the polypeptide such as thiol groups of a phage encoded polypeptide with the molecular scaffold for one hour.

Suitably they are reacted at 30° C.

Suitably they are reacted with molecular scaffold (such as tris(bromomethyl)benzene) at a concentration of 10 µM to 40 µM.

Suitably reaction is in aqueous buffer.

Suitably reaction is at pH 8.

Suitably reaction buffer contains acetonitrile. Suitably reaction buffer contains 20% acetonitrile.

Most suitably the reaction features two or more of the above conditions. Suitably the reaction features three or more of the above conditions. Suitably the reaction features four or more of the above conditions. Suitably the reaction features five or more of the above conditions. Suitably the reaction features six or more of the above conditions. Suitably the reaction features each of the above conditions.

These reaction conditions are optimized to quantitatively react thiol groups of a polypeptide with the reactive groups of tris(bromomethyl)benzene. Under the same reaction conditions, about 20% of the phage particles remain infective to bring the genetic code into bacterial cells for propagation and decoding.

In one embodiment the molecular scaffold, such as TBMB, may be attached to the polypeptide, such as a phage encoded polypeptide, by reaction (incubation) of thiol groups of the polypeptide for one hour at 30° C. with 10 µM TBMB (i.e. tris(bromomethyl)benzene) in the presence of 10 µM TCEP in aqueous buffer pH 8 containing 20% acetonitrile. In another embodiment, the reaction can be carried out using 40 µM TBMB in the presence of 30 µM TCEP in the same buffer.

The inventors also disclose the effect of concentration of the molecular scaffold in the reaction on phage infectivity. In particular the invention suitably minimises the concentration of molecular scaffold used in the reaction. In other words, the lower the concentration of molecular scaffold used at the time of reaction with the polypeptide of the phage, the better, provided always that sufficient molecular scaffold becomes joined to the phage polypeptide. The advantage of minimising the molecular scaffold present in this way is superior preservation of phage infectivity following coupling of the molecular scaffold. For example, when the molecular scaffold is TBMB, concentrations of molecular scaffold greater than 100 µM can compromise infectivity. Thus suitably when the molecular scaffold is TBMB then suitably the concentration of TBMB present at the time of bonding to the polypeptide is less than 100 µM.

(C) Use of Dual-Specific Ligands According to the Invention

Multispecific peptide ligands selected according to the method of the present invention may be employed in in vivo therapeutic and prophylactic applications, in vitro and in vivo diagnostic applications, in vitro assay and reagent applications, and the like.

As alluded to above, the molecules selected according to the invention are of use in diagnostic, prophylactic and therapeutic procedures. In general, the use of a dual specific peptide ligand can replace that of a dual specific antibody. Dual specific antibodies selected according to the invention are of use diagnostically in Western analysis and in situ protein detection by standard immunohistochemical procedures; for use in these applications, the antibodies of a selected repertoire may be labelled in accordance with techniques known to the art. In addition, such antibody polypeptides may be used preparatively in affinity chromatography procedures, when complexed to a chromatographic support, such as a resin. All such techniques are well known to one of skill in the art. Peptide ligands according to the present invention possess binding capabilities similar to those of antibodies, and may replace antibodies sin such assays.

Diagnostic uses of the dual specific ligands according to the invention include homogenous assays for analytes which exploit the ability of dual specific peptide ligands to bind two targets in competition, such that two targets cannot bind simultaneously (a closed conformation), or alternatively their ability to bind two targets simultaneously (an open conformation).

A true homogenous immunoassay format has been avidly sought by manufacturers of diagnostics and research assay systems used in drug discovery and development. The main diagnostics markets include human testing in hospitals, doctor's offices and clinics, commercial reference laboratories, blood banks, and the home, non-human diagnostics (for example food testing, water testing, environmental testing, bio-defence, and veterinary testing), and finally research (including drug development; basic research and academic research).

At present all these markets utilise immunoassay systems that are built around chemiluminescent, ELISA, fluorescence or in rare cases radio-immunoassay technologies. Each of these assay formats requires a separation step (separating bound from un-bound reagents). In some cases, several separation steps are required. Adding these additional steps adds reagents and automation, takes time, and affects the ultimate outcome of the assays. In human diagnostics, the separation step may be automated, which masks the problem, but does not remove it. The robotics, additional reagents, additional incubation times, and the like add considerable cost and complexity. In drug development, such as high throughput screening, where literally millions of samples are tested at once, with very low levels of test molecule, adding additional separation steps can eliminate the ability to perform a screen. However, avoiding the separation creates too much noise in the read out. Thus, there is a need for a true homogenous format that provides sensitivities at the range obtainable from present assay formats. Advantageously, an assay possesses fully quantitative read-outs with high sensitivity and a large dynamic range. Sensitivity is an important requirement, as is reducing the amount of sample required. Both of these features are features that a homogenous system offers. This is very important in point of care testing, and in drug development where samples are precious. Heterogenous systems, as currently available in the art, require large quantities of sample and expensive reagents.

Applications for homogenous assays include cancer testing, where the biggest assay is that for Prostate Specific Antigen, used in screening men for prostate cancer. Other applications include fertility testing, which provides a series of tests for women attempting to conceive including beta-hcg for pregnancy. Tests for infectious diseases, including hepatitis, HIV, rubella, and other viruses and microorganisms and sexually transmitted diseases. Tests are used by blood banks, especially tests for HIV, hepatitis A, B, C, non A non B. Therapeutic drug monitoring tests include monitoring levels of prescribed drugs in patients for efficacy and to avoid toxicity, for example digoxin for arrhythmia, and phenobarbital levels in psychotic cases; theophylline for asthma.

Diagnostic tests are moreover useful in abused drug testing, such as testing for cocaine, marijuana and the like. Metabolic tests are used for measuring thyroid function, anaemia and other physiological disorders and functions.

The homogenous binding assay format is moreover useful in the manufacture of standard clinical chemistry assays. The inclusion of immunoassays and chemistry assays on the same instrument is highly advantageous in diagnostic testing. Suitable chemical assays include tests for glucose, cholesterol, potassium, and the like.

A further major application for homogenous binding assays is drug discovery and development: High throughput screening includes testing combinatorial chemistry libraries versus targets in ultra high volume. Signal is detected, and positive groups then split into smaller groups, and eventually tested in cells and then animals. Homogenous assays may be used in all these types of test. In drug development, especially animal studies and clinical trials heavy use of immunoassays is made. Homogenous assays greatly accelerate and simplify these procedures. Other Applications include food and beverage testing: testing meat and other foods for *E. coli, salmonella*, etc; water testing, including testing at water plants for all types of contaminants including *E. coli*; and veterinary testing.

In a broad embodiment, the invention provides a binding assay comprising a detectable agent which is bound to a dual specific peptide ligand according to the invention, and whose detectable properties are altered by the binding of an analyte to said dual specific peptide ligand.

Such an assay may be configured in several different ways, each exploiting the above properties of dual specific peptide ligands.

Where the dual specific ligand is in a closed conformation, the assay relies on the direct or indirect displacement of an agent by the analyte, resulting in a change in the detectable properties of the agent. For example, where the agent is an enzyme which is capable of catalysing a reaction which has a detectable end-point, said enzyme can be bound by the peptide ligand such as to obstruct its active site, thereby inactivating the enzyme. The analyte, which is also bound by the dual specific ligand, displaces the enzyme, rendering it active through freeing of the active site. The enzyme is then able to react with a substrate, to give rise to a detectable event. In an alternative embodiment, the peptide ligand may bind the enzyme outside of the active site, influencing the conformation of the enzyme and thus altering its activity. For example, the structure of the active site may be constrained by the binding of the ligand, or the binding of cofactors necessary for activity may be prevented.

The physical implementation of the assay may take any form known in the art. For example, the dual specific peptide ligand/enzyme complex may be provided on a test strip; the substrate may be provided in a different region of the test strip, and a solvent containing the analyte allowed to migrate through the ligand/enzyme complex, displacing the enzyme, and carrying it to the substrate region to produce a signal. Alternatively, the ligand/enzyme complex may be provided on a test stick or other solid phase, and dipped into an analyte/substrate solution, releasing enzyme into the solution in response to the presence of analyte.

Since each molecule of analyte potentially releases one enzyme molecule, the assay is quantitative, with the strength of the signal generated in a given time being dependent on the concentration of analyte in the solution.

Further configurations using the analyte in a closed conformation are possible. For example, the dual specific ligand may be configured to bind an enzyme in an allosteric site, thereby activating the enzyme. In such an embodiment, the enzyme is active in the absence of analyte. Addition of the analyte displaces the enzyme and removes allosteric activation, thus inactivating the enzyme.

In the context of the above embodiments which employ enzyme activity as a measure of the analyte concentration, activation or inactivation of the enzyme refers to an increase or decrease in the activity of the enzyme, measured as the ability of the enzyme to catalyse a signal-generating reaction. For example, the enzyme may catalyse the conversion of an undetectable substrate to a detectable form thereof. For example, horseradish peroxidase is widely used in the art together with chromogenic or chemiluminescent substrates, which are available commercially. The level of increase or decrease of the activity of the enzyme may between 10% and 100%, such as 20%, 30%, 40%, 50%, 60%, 70%, 80% or 90%; in the case of an increase in activity, the increase may be more than 100%, i.e. 200%, 300%, 500% or more, or may not be measurable as a percentage if the baseline activity of the inhibited enzyme is undetectable.

In a further configuration, the dual specific ligand may bind the substrate of an enzyme/substrate pair, rather than the enzyme. The substrate is therefore unavailable to the enzyme until released from the dual specific ligand through binding of the analyte.

The implementations for this configuration are as for the configurations which bind enzyme.

Moreover, the assay may be configured to bind a fluorescent molecule, such as a fluorescein or another fluorophore, in a conformation such that the fluorescence is quenched on binding to the ligand. In this case, binding of the analyte to the ligand will displace the fluorescent molecule, thus producing a signal. Alternatives to fluorescent molecules which are useful in the present invention include luminescent agents, such as luciferin/luciferase, and chromogenic agents, including agents commonly used in immunoassays such as HRP.

The assay may moreover be configured using a dual specific ligand in the "open" conformation. In this conformation, the dual specific ligand is capable of binding two targets simultaneously. For example, in a first embodiment, the assay may be configured such that the dual specific ligand binds an enzyme and a substrate, where the enzyme has a low affinity for the substrate; and either the enzyme or the substrate is the analyte.

When both substrate and enzyme are brought together by the dual specific ligand the interaction between the two is potentiated, leading to an enhanced signal.

Alternatively, the dual specific ligand may bind a fluorescent molecule, as above, which is quenched by the binding of the analyte. In this embodiment, therefore, fluorescence is detectable in the absence of analyte, but is quenched in the presence thereof.

The basic implementation of such an assay is as provided above for closed conformation assays.

Therapeutic and prophylactic uses of dual-specific ligands prepared according to the invention involve the administration of ligands selected according to the invention to a recipient mammal, such as a human. Dual-specificity can allow peptide ligands to bind to multimeric antigen with great avidity. Dual-specific peptide ligands can allow the crosslinking of two antigens, for example in recruiting cytotoxic T-cells to mediate the killing of tumour cell lines.

Dual-specificity also allows the generation of peptide ligands that can antagonise the biological activity of two or more targets which is advantageous in some instances in the treatment of medical conditions. Dual-specificity also allows the generation of peptide ligand that can act as agonists at two or more targets which is advantageous in some instances in the treatment of medical conditions.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The peptide ligands of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available.

Methods for the testing of systemic lupus erythematosus (SLE) in susceptible mice are known in the art (Knight et al. (1978) J. Exp. Med., 147: 1653; Reinersten et al. (1978) New Eng. J: Med., 299: 515). Myasthenia Gravis (MG) is tested in SJL/J female mice by inducing the disease with soluble AchR protein from another species (Lindstrom et al. (1988) Adv. Inzn7unol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-213; McFarlin et al. (1973) Science, 179: 478: and Satoh et al. (1987) J; Immunol., 138: 179).

Generally, the present peptide ligands will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringers dextrose, dextrose and sodium chloride and lactated Ringers. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringers dextrose. Preservatives and other additives, such as antimicrobials, antioxidants, chelating agents and inert gases, may also be present (Mack (1982) Remington's Pharmaceutical Sciences, 16th Edition).

The peptide ligands of the present invention may be used as separately administered compositions or in conjunction with other agents. These can include antibodies, antibody fragments and various immunotherapeutic drugs, such as cylcosporine, methotrexate, adriamycin or cisplatinum, and immunotoxins. Pharmaceutical compositions can include- "cocktails" of various cytotoxic or other agents in conjunction with the selected antibodies, receptors or binding proteins thereof of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counter-indications and other parameters to be taken into account by the clinician.

The peptide ligands of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that use levels may have to be adjusted upward to compensate.

The compositions containing the present peptide ligands or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide ligand per kilogram of body weight, with doses of 0.05 to 2.0 mg/kg/dose being more commonly used. For prophylactic applications, compositions containing the present peptide ligands or cocktails thereof may also be administered in similar or slightly lower dosages.

A composition containing a peptide ligand according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the selected peptide ligands whereby the undesired cells are killed or otherwise removed from the blood for return to the mammal in accordance with standard techniques.

EXAMPLES

Example 1

Protease Resistant Bicyclic Peptides Against MDM2

MDM2 is an enzyme (an E3 ubiquitin ligase) that recognises the trans-activation domain of p53, the tumour suppressor, leading to ubiquitinylation and degradation of p53 by the proteosome. A nutlin inhibitor of the p53-MDM2 interaction can lead to in vivo activation of the p53 pathway, and it has been suggested that such agents may have potential as anti-cancer agents. Here we describe the selection of two bicyclic peptides (PEP10 and PEP48) against MDM2, a target "antigen". The affinity of each synthetic peptide was sub-micromolar, and in the range 250-750 nM. At least one of the peptides was shown by competition ELISA to bind to the same site as a linear peptide previously shown to block the p53-MDM2 interaction.

Protocols generally followed those described earlier in Heinis et al., 2009, Nature Chemical Biology 5, 502-507, unless otherwise indicated. In the work of Heinis et al., both targets, kallikrein and cathepsin G, were proteases, and the kallikrein inhibitor is fairly resistant to proteolysis by kallikrein, although it includes a kallikrein cleavage site. MDM2 is not a protease, and therefore it was not clear whether the selected peptides would also be resistant to protease. For this, and other reasons (for detail see below), we included one or more protease (chymotrypsin) steps after reaction of the phage peptide repertoires with the TBMB (under oxidising or reducing conditions) and before selection of the repertoire against MDM2. The two selected phage peptides PEP10 and PEP 48 appear resistant to proteolysis, as shown by phage ELISA.

Phage Production and Purification

The phage peptide library with diversity of at least $4\times10^9$ clones was prepared and TBMB conjugated as described earlier with a few modifications.

1. The cx6 library of phage as described earlier (which had been prepared from TG1 cells) was used to infect the non-suppressor strain HB2151 (Carter, Bedouelle & Winter. 1985. Nucleic Acids Res. 13:4431-43), and the infected cells plated. The bacteria were scraped from the plates in about 8 ml 2×TY medium, 30 ug/ml chloramphenicol, 10% glycerol (v/v).
2. About 0.8 ml of the stock was added to 800 ml 2×TY medium with 30 ug/ml chloramphenicol to obtain an OD of about 0.1 at 600 nm. The culture was incubated at 30 C, and shaken in a 2 liter flask at 200 rpm for 16 hrs.
3. The cell culture was centrifuged at 4,000 rpm (Heraeus Megafuge 2R) for 30 min at 4 C. The supernatant was transferred to 200 ml cold 20% PEG, 2.5 M NaCL. The mixture was left on ice for 1 hr.
4. The precipitated supernatant/phage mixture was spun down for 30 min at 4 C and the supernatant was discarded.
5. The phage was resuspended in 35 ml PBS, 5 mM EDTA followed by spinning for 15 min at 4000 rpm (Heraeus Megafuge 2R) to remove cellular debris. The supernatant was transferred into a new 50 ml Falcon tube.

Modification of Phage with TBMB 1. 5 ml of 8 mM TCEP (in $H_2O$) was added to the phage to obtain a final concentration 1 mM TCEP. The tube was inverted several time to mix and incubated for 1 hr at 42 C water bath.
2. The TCEP was removed by a second PEG precipitation. 10 ml of 20% PEG, 2.5 M NaCL (degassed solution) was added, mixed, and incubated on ice for 45 min and spun for 30 min at 4000 rpm, 4 C.
3. The supernatant was carefully removed and pellet resuspended in 12 ml PBS, 5 mM EDTA, 10 uM TCEP (degassed buffer)
4. 3 ml of 50 uM TBMB in acetonitrile was added to the 12 ml of reduced phage to obtain a final TBMB concentration of 10 uM. The tube was inverted several times and left at 30 C for 1 hr in a water bath. The phage were cooled on ice and precipitated with ⅕ volume of 20% PEG, 2.5 M NaCL for 30 min. The phage were collected by spinning at 4000 rpm (Hereaus Megafuge 2R) for 20 min. Supernatant was removed and the phage resuspended in 4 ml of PBS. Phage was transferred into the 2 ml Eppendorf tubes and spun at 13000 rpm (Eppendorf benchtop centrifuge) for 10 min. Supernatant was transferred into a new Eppendorf tube and phage infectivity was measured.

Phage Selection: General Protocol

First Round of Selection

1. Purified and chemically conjugated phage as above was selected against biotinylated MDM2 (bio-MDM2) peptide (res 2-125) immobilized on the surface of the streptavidin-coated Dynabeads (Dynal Biotech). 80 ul of beads were first washed and blocked with 2% (w/v) Marvell milk powder in PBS (PBSM) for 40 min followed by incubation with 100 nM bio-MDM2 for 20 min in a total volume of 1 ml.
2. Chemically modified phage ($10^{10}$-$10^{11}$TU) was incubated with PBSM for 40 min.
3. Blocked Ag-coated beads from step 1 were washed from the excess of the Ag with 0.1% Tween in PBS (PBST) and incubated with the blocked phage for 30 min in a total volume of 1 ml.
4. Unbound phage were washed with 10× with PBST followed by 2× with PBS. After each third washing step the phage coated beads were transferred into a new Eppendorf tube.
5. Phage were eluted by incubating with 500 ul of 50 mM glycine pH 2.2 for 10 min on a rotating wheel. Eluted phage were neutralized with 250 ul of 1M Tris, pH7.5.
6. 375 ul of phage was incubated with 10 ml of HB2151 cells for 90 min at 37 C without shaking.
7. The infected cells were then shaken for 30 min at 37 C and then plated on a chloramphenicol plate (20×20 cm).
8. The colonies were scraped off the plate in 2×TY, chloramphenicol, 10% glycerol as described above, and stored as a glycerol stock at −80 C. A fraction of the cells was used to prepare phage for the second round of selection.

Second Round of Selection

The second round of selection was similar to the first one except for a few modifications.

1. Neutravidin-coated magnetic beads were used instead of streptavidin ones.
2. The amount of antigen used in the selection was 20 nM.
3. Chemically modified phage ($10^{10}$–$5\times10^{10}$TU) was first treated with 50 ug/ml of chymotrypsin for 2 min followed by blocking with PBSM for 40 min.
4. Unbound phage was washed with 15× with PBST followed by 2× with PBS, otherwise as above.

Phage Selection: Variant Protocol

Clone 48 was selected using the general protocol as above, whereas clone 10 was developed as a result of a modified protocol being introduced. The modifications are the following:

1. In the first round chemically modified phage were pre-treated with 50 ug/ml of chymotrypsin for 2 min followed by blocking with PBSM for 40 min.
2. In the second round chemically modified phage were first reduced with 5 mM DTT for 20 min followed by incubation with 50 ug/ml of chymotrypsin for 2 min and blocking with PBSM for 40 min.

Peptide Synthesis

The encoded peptides from phage clone 48 and phage clone 10 were synthesized with free N- and C-termini. PEP10: H-Ser-Cys-Glu-Leu-Trp-Asn-Pro-Lys-Cys-Arg-Leu-Ser-Pro-Phe-Glu-Cys-Lys-Gly-OH (SEQ ID NO. 5); PEP48: H-Ser-Cys-Val-Arg-Phe-Gly-Trp-Thr-Cys-Asp-Asn-Ser-Trp-His-Gly-Cys-Lys-Gly-OH (SEQ ID NO. 6).

The syntheses was performed by Fmoc-peptide synthesis on a CEM Liberty microwave peptide synthesizer on 0.1 mmol Fmoc-Gly-PEG PS resin using a 5-fold excess of Fmoc-amino-acids activated with PyBop in DMF and DIPEA in NMP (1 equivalent and 2 equivalents respectively. Side-chain protecting groups were as follows: Arg(Pbf); Asn(Trt); Asp(OtBu); Cys(Trt); Glu(OtBu); Lys(Boc); Ser (tBu); Thr(tBu); Trp(Boc). Fmoc-deprotection was carried out using 20% v/v Piperidine/DMF containing 0.1M HOBt. The H-peptidyl-resins were washed with DMF, then propan-2-ol and dried in vacuo. Cleavage of side-chain protecting groups and from the support was effected using 94:2.5:2.5:1 v/v/v/v TFA/EDT/H$_2$O/iPr$_3$SiH for 2 hours. The peptide/TFA mixture was filtered to remove the support and the peptide/TFA mixture was diluted with water and washed with Et$_2$0 (5-times) and the aqueous layer lyophilized.

Reverse-phase hplc were performed on a Phenomenex Jupiter 5μ C18 300 Å250×4.6 mm column. Buffer A: 0.1% TFA/H20; Buffer B: CH3CN containing 10% Buffer A. The column was eluted isocratically with 10% Buffer B for 2 minutes, then with a linear gradient of 10-90% over 25 minutes. Detection was at 215/230 nm; flow rate of 1.5 ml/min.

The peptides were lyophilized and checked by mass spectrometry. PEP10 MALDI-TOF mass (M+H): 2099.9 Da (Theory: 2098.4 Da.) PEP48 MALDI-TOF Mass (M+H): 2043.8 Da (Theory: 2042.8 Da.). The peptides were conjugated with TBMB as described in Example 2.

Binding Assays

Phage ELISA Assay 0.6 μg/mL of biotinylated MDM2 peptide (res 2-125) was immobilized on a streptavidin-coated plate (Roche). Plate was blocked with PBSM (but 4% in milk powder) and linear or TBMB-conjugated phage (10$^7$ TU/well in PBSM in the presence or absence of 5 mM DTT) was incubated on the plate for 50 min at room temperature. Similarly, phage was first reduced in 5 mM DTT for 20 min, treated with chymotrypsin (50 ug/ml in PBS) for 2 min, mixed with PBSM (final concentration) and incubated on the plate for 50 min at room temperature. Phage was detected using an anti-M13-HRP monoclonal antibody (1:5000, Amersham).

The results (FIG. 1) showed qualitatively that both phage clones 10 and clone 48 bind to MDM2 as the cyclic conjugate but not as the unconjugated peptide (whether or not pre-treated with DTT). Furthermore the binding of the conjugated peptide resists proteolysis. Note that DTT can reduce the disulphide bonds of chymotrypsin leading to its inactivation as a protease. To ensure that the chymotrypsin was active under the conditions of the assay, we incubated control phage bearing a linear peptide that binds MDM2 after pre-treatment as above with DTT. Under the conditions of our experiment, the binding activity of the control phage was lost on proteolysis. In other experiments we have used up to 0.2 mM-5 mM TCEP in the presence of chymotrypsin (0.1 mg/ml-1 mg/ml) for 2 minutes at room temperature in PBS. These conditions also allowed us to distinguish between the linear and cyclic peptides on phage.

Fluorescence Anisotropy Measurements

Titration experiments were run on a Horiba Jobin Yvon fluorimeter equipped with the Hamilton Microlab titrator controlled by laboratory software. The $\lambda_{ex}$ and $\lambda_{em}$ used were 295 nm and 350 nm, respectively. The slit widths for excitation and emission were 5 nm and 15 nm and the integration time 10 s was used for each measurement. The intrinsic fluorescence of tryptophan in peptides 10, 48 was used to measure their binding affinity for MDM2 (res 2-125). The experiments were performed at 23 C.° in PBS, 5 mM DTT. Usually 250 ul of MDM2 (150 uM) was titrated into 1.2 ml of peptide (1 uM). Titration data were analyzed with a standard 1:1 binding model by using the quadratic solution to the equilibrium Kd=[A][B]/[AB]. Kd is the dissociation rate, and [A] and [B] refer to the concentration of a titrant (MDM2) and fluorescent peptides 10 and 48, respectively. The fitting equation contained an extra term to account for linear drift.

Figure 2:
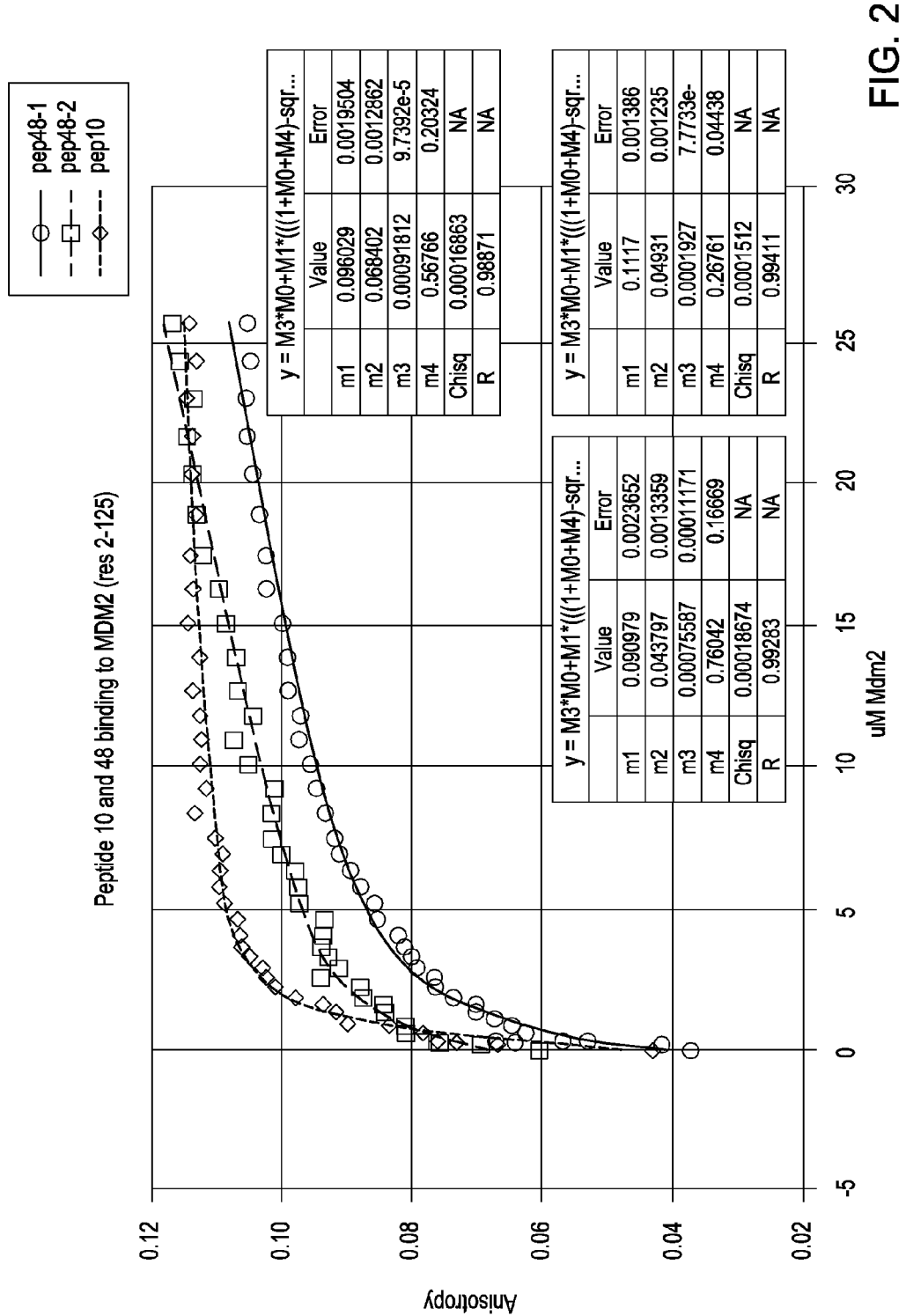
FIG. 2 shows a fluorescence anisotropy plot for peptides PEP10 and PEP48, indicating the affinity for MDM2. See Example 1.

The results (FIG. 2 and below) indicate that the affinity of each peptide is sub-micromolar, and in the range 250-750 nM. The measurements for PEP48 were repeated.
PEP10+MDM2, measured λex=295 nm, Kd=267 nM;
PEP48+MDM2, measured λex=280 nm, Kd=760 nM;
PEP48+MDM2, measured λex=295 nm, Kd=567 nM Competition Assays The binding of PEP48 phage to MDM2 was competed by a peptide pMI (TSFAEYWNLLSP (SEQ ID NO. 7)) that binds to MDM2 at the p53 site with a Kd=3.3 nM (Pazgier et. al., 2009 PNAS, 106, 4665-4670). 0.6 μg/ml of biotinylated MDM2 peptide (res 2-125) was immobilized on a streptavidin-coated plate (Roche). Plate was blocked with PBSM. TBMB-conjugated phage (10$^7$ TU/well in 1% PBSM) was premixed with a range of concentrations of pDI (from 6.94 nM to 1 uM) and incubated on the plate for 75 min at room temperature. Phage was detected using an anti-M13-HRP monoclonal antibody (1:5000, Amersham). The binding of PEP48 phage to MDM2 was inhibited by addition of the pMI peptide, with an estimated 1050=125 nM.

Example 2

Cyclic Peptides Binding to Two or More Targets

The work by Heinis et al., (2009), demonstrates the isolation of a bicyclic peptide (PK15) against kallikrein (PK15). PK15 was made by a two stage process. A first bicyclic repertoire was created with diversity in both loops. After iterative selection with kallikrein, a set of consensus sequences emerged in the first loop, of which PK2 was representative. A second repertoire was then created, keeping the PK2 sequence in the first loop, and diversifying the second loop. After iterative selection with kallikrein, a set of consensus sequences emerged in the second loop. The two-stage process led to an improvement in binding affinity.

The emergence of consensus sequences in the first loop of PK2 suggests that this loop makes a significant contribution to binding. It does not exclude the possibility that the second loop also make a significant contribution to binding in PK2. Indeed the emergence of a second loop consensus sequence in PK15 suggests that the second loop does make a significant contribution to binding in PK15.

Nevertheless we wondered whether it might be possible to build a bicyclic peptide with binding specificities to two targets by combining individual loops from bicyclic peptides of different specificity. Although we expected to see a significant loss in binding affinity for each target, we considered that further mutagenesis should lead to variants with improved binding affinities.

Accordingly, we first synthesized a number of variants of the first loop of PK15 on the TBMB core in manner described earlier by Heinis et al. (2009), or by a method described below in which we attempted to mimic the reaction conditions used for conjugation of TBMB with the phage. For the tricyclic a further chemical step was taken to join the N- and C-terminus of a bicyclic peptide. The bicyclic peptides were purified by HPLC, checked by mass spectrometry, and dried by lyophilisation. The table summarises the IC50 for inhibition of kallikrein activity for each variant peptide.

The first loop of PK15 is underlined in each of the variants, and was combined with the first loop of the CG4 peptide (double underlined) directed against cathepsin G (Heinis et al, 1990), or the first loop of PEP48 (dashed underline) directed against MDM2 (see WO 2009/098450).

Further discussion of other strategies for making bispecific phage is described in Example 4.

Synthesis of TBMB-Peptide Conjugates

Initial reactions were performed to mimic the conditions used during phage selection. Typically, 5 mg of the purified peptide was dissolved in 1 ml water and 0.8 ml 50 mM $NH_3HCO_3$ added, followed by 40 µl of TCEP. TBMB (3 equivalents based on weight of peptide) dissolved in MeCN was added to the reaction. The reaction was left for 1.5 hrs then monitored by HPLC. On completion the reaction was purified by HPLC. Typically 0.5 to 1.5 mg of final product was obtained. This method gives rise to many by-products, the major product being the desired mass +250 amu. This corresponds to addition of TCEP to the desired product, and that the yield of this product increases with reaction time. In addition other higher mass products corresponding to addition of a second TBMB were observed by MALDI-TOF mass spec, but were not isolated.

| Peptide name | Peptide sequence | IC50 |
|---|---|---|
| PK15L1-PK15L2 bicyclic | (H)-AC<u>SDRFRN</u>CPADEALCG-(OH)<br>SEQ ID NO. 8 | 13 nM |
| X-CG4L1-PK15L1-Y bicyclic | (H)-ALC<u>IFDLGF</u>C<u>SDRFRN</u>CPADE-(OH)<br>SEQ ID NO. 9 | 15 µM |
| CG4L1-PK15L1-PK15L2 tricyclic | (H)-ALC<u>IFDLGF</u>C<u>SDRFRN</u>CPADE-(OH)<br>SEQ ID NO. 9 | 15 µM |
| PK15L1-CG4L1 bicyclic | (H)-AC<u>SDRFRN</u>C<u>IFDLGF</u>CG-(OH)<br>SEQ ID NO. 10 | 200 nM |
| PK15L1-PEP48L1 bicyclic | (H)-AC<u>SDRFRN</u>CVRFGWTCG-(OH)<br>SEQ ID NO. 11 | 11 µM |
| FmocPEP48L1-PK15L1 bicyclic | Fmoc-W-GGG-CVRFGWTC<u>SDRFRN</u>CG-($NH^2$)<br>SEQ ID NO. 12 | 17 µM |

The results show that the first loop of PK15 is able to inhibit kallikrein activity when combined with loops from bicyclic (or a tricyclic) peptides directed against a second target. However the inhibitory activity is much less than when combined with its cognate loop, and varies according to the sequences and/or order of the non-cognate loops.

Figure 3:
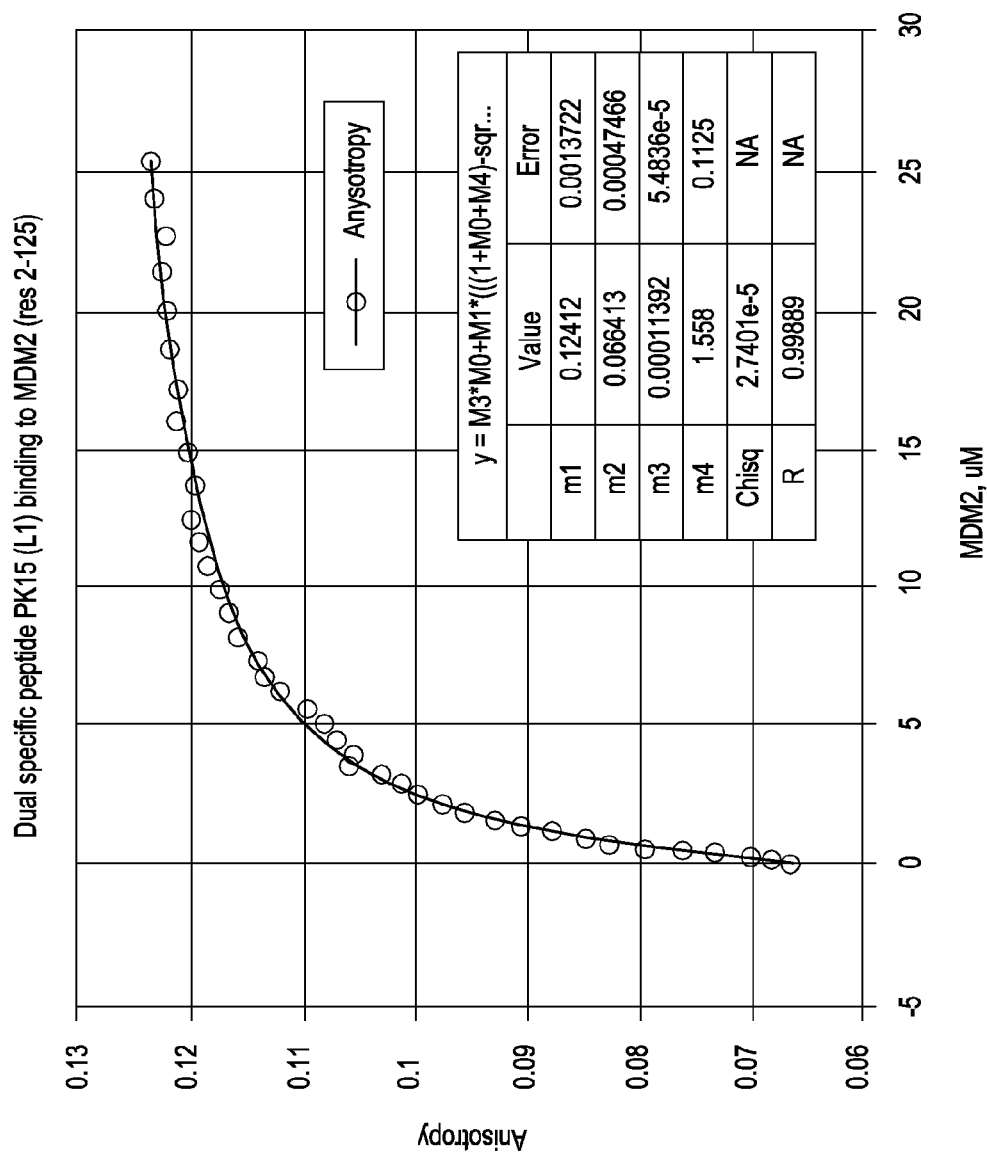
FIG. 3 shows a fluorescence anisotropy plot for a dual specific peptide comprising loops from PEP48 and PK15 (Example 2).

We also obtained results for the binding of the first loop of PEP48 in combination with PK15 (FIG. 3). Thus the PK15L1-PEP48L1 bicyclic peptide has a binding affinity (Kd=1.55 uM) for MDM2 only two or three fold lower than that for the entire PEP48L1-PEP48L2 bicyclic peptide (Example 1, Kd=500-800 nM). Furthermore, as shown later in Example 3, the FmocPEP48L1-PK15L1 peptide is estimated to have a binding affinity of <1 uM. This demonstrates that it is possible to combine loops from two bicyclic peptides of different target specificity, and thereby to create a bicyclic peptide with the two target specificities.

It is possible to improve the binding affinities of these bicyclic peptides, for example by (a) synthesizing a mutated DNA cassette encoding the peptides with "spiked" oligonucleotides, (b) displaying said mutant peptide repertoire on phage, and (c) subjecting said phage repertoire to rounds of selection under increasingly stringent conditions (for example using lower concentrations of antigen, or more extensive washes of the phage bound to target. Furthermore by selecting the repertoire against each of the targets in turn (with or without intervening rounds of bacterial growth, depending on phage yields), it should be possible to ensure that the selection pressure is maintained on both targets.

Based on the formation of TCEP adducts a preferred method was developed. Following cleavage of the peptide from the resin, it was either purified directly by HPLC or pre-treated with TCEP for 15 mins prior to HPLC purification. The product from the HPLC reaction, in the HPLC elution buffer (typically 6 ml) is neutralised with 50 mM $NH_3HCO_3$ (4 ml) and TBMB added in MeCN as above. The addition of 10% THF results in a clear solution and therefore accelerates the reaction. Reactions are monitored by mass spec, but typically are complete in 1-2 hrs. There are minimal by-products from this reaction (though the presence of product +16 is observed by mass spec). The reaction requires concentration to remove organic solvents prior to HPLC purification otherwise the product tends to elute with the solvent front. Yields of product from this method are typically 0.5 to 1.5 mg from 3 mg peptide, but this has not been optimised.

Synthesis of Tricyclic Peptide

The tricyclic peptide CG4L1-PK15L1-PK15-L2 was synthesised as follows: approximately 1 mg of the bicyclic X-CG4L1-PK15L1-Y (where X and Y represent portions of PK15L2) was dissolved in 2 ml of 20 mM $NH_3HCO_3$ and treated with EDC (0.8 mg in 100 µl water, 10 equivalents) and heated in microwave synthesiser at 50 W starting at 0° C. up to 37° C. Reaction progress was monitored at 15 mins and 30 mins when the cyclised product was the major product but a second loss of water was also observed. The reaction was purified by HPLC (semi-prep) to give the tricyclic conjugate as a single peak, yield 0.5 mg.

Kallikrein Assays

Enzymes were purchased from Sigma Aldrich and substrates from Bachem A G. The assay buffer is composed of 10 mM Tris pH 7.4, 150 mM NaCl, 10 mM $MgCl_2$, 1 mM $CaCl_2$, 0.1% BSA, 0.01% Triton X100 and 5% DMSO. Enzymes are incubated with inhibitors for 30 minutes at RT prior to addition of substrate. All experiments were recorded at 30° C. for 90 minutes.

Assays were performed on a BMG Pherastar plate reader at wavelengths of exc/em 350/450 nm. Kallikrein was bought as a solution of 1080 μg/mL and diluted to a working concentration of 0.3 nM in assay buffer. Substrate Z-Phe-Arg-amc was solubilised at the stock concentration of 10 mM in DMSO and diluted to a working concentration of 300 μM with assay buffer. Inhibitors were solubilised in assay buffer to a stock concentration of 60 μM. 50 μL of each reagent is introduced in wells for a final volume of 150 μL per well. Final concentration of kallikrein in assay is 0.1 nM and substrate is 100 μM.

Final concentrations of inhibitors were: 0.5 nM, 1 nM, 2 nM, 5 nM, 8 nM, 10 nM, 20 nM, 50 nM, 80 nM, 100 nM, 200 nM, 500 nM, 800 nM, 1 μM, 2 μM, 5 μM, 8 μM, 10 μM and 20 μM. The initial rate of the reaction is obtained by plotting fluorescence=f (time) data and by fitting a linear trendline for each concentration of inhibitor. The inhibition curves are obtained by plotting initial rate=f ([I]) and $IC_{50}$ values can be evaluated.

Example 3

Addition of a Serum Albumin Binding Function to a Bicyclic Peptide to Provide Three Functions within the Same Peptide The ligands of the invention can include conjugates to one or more functional groups. The functional group may be linked directly to the peptide, or to the scaffold. The functional group may comprise a natural peptide, or chemical group or both. Here we describe a functional group that may be linked to a ligand of the invention so as to confer binding to serum albumin, and thereby extend the serum half-life of the ligand.

The X-ray crystallographic structure of serum albumin has been solved in complex with warfarin (Petitpas et. (2001) J. Biol. Chem. 276, 22804-22809). The warfarin sits in a hydrophobic pocket deep in the structure. We wondered whether other chemical entities of similar structure might confer binding to a peptide. We noted that the fluorenyloxy-carbonyl group (Fmoc), that is used to protect amino groups during peptide synthesis might be suitable; likewise methoxy-coumarin (Mca), that is used to fluorescently label peptides.

Accordingly we have produced lysine and simple peptide conjugates with Fmoc and/or Mca, and tested these in binding to serum albumin. The experiments below show that Fmoc binds to serum albumin but Mca does not bind; furthermore Fmoc-Trp or Fmoc-Phe leads to an increase in binding affinity. We expect that other conjugates with the fluorene ring will also bind to serum albumin; for example, fluorene acetic acid, which is expected to be more stable to hydrolysis.

We also show the use of the Fmoc-Trp with a model bicyclic peptide. Thus an N-terminal Fmoc-Trp and glycine spacer was appended to the bicyclic peptide (PEP48L1-PK15L1). This bicyclic peptide comprises loops from bicyclic peptides of two different specificities. The first loop was the first loop (L1) from PEP48, a bicyclic peptide that binds to MDM2, as described in Examples 1. The second loop was the first loop (L1) from PK15, the bicyclic peptide that inhibits kallikrein, as described earlier (Heinis et al., 2009). The fluorescence titration shows that the bicyclic peptide is able to bind to serum albumin with an affinity of about 60 nM, and well within the range suitable for half-life extension in serum (Nguyen et al. (2006) PEDS19, 291-297).

The binding affinity of this bicyclic peptide was also measured for MDM2. The preliminary data showed that the peptide was able to bind to MDM2 with an affinity <1 uM. A further preliminary experiment (described in Example 2), revealed that the IC50 for inhibition of kallikrein by this peptide is about 17 micromolar. Thus the bicyclic peptide has three functions; binding to serum albumin conferred by the Fmoc peptide, binding to MDM2 via the first peptide loop, and binding to kallikrein by the second peptide loop.

The binding functions in this example may each have some utility in a therapeutic drug, but we do not mean to imply that the combination of these three functions together in the same drug would be particularly advantageous. However for a drug to be delivered to a target within the bloodstream (for example for inhibition of kallikrein), or within a cell (for example to block the p53-MDM2 interaction) it is likely to be advantageous to have an extended half-life in the serum.

Binding of Fmoc-Aminoacids to Bovine Serum Albumin

For determining the affinity constant ($K_d$) of a fluorophore to target protein, we chose fluorescence anisotropy titrations. Here, increasing amounts of bovine serum albumin (BSA) are titrated into fluorescent peptide, and if binding occurs, a typical saturation curve (recorded as a function of change in anisotropy (r)) of peptide increasingly complexed by BSA is observed. Using the quadratic solution to the binding equilibrium $K_d=A*B/[AB]$, the $K_d$ can be determined (Teufel et al, (2007) PNAS 104, 7009-7014).

Fmoc-Lys-Mca

Figure 4:
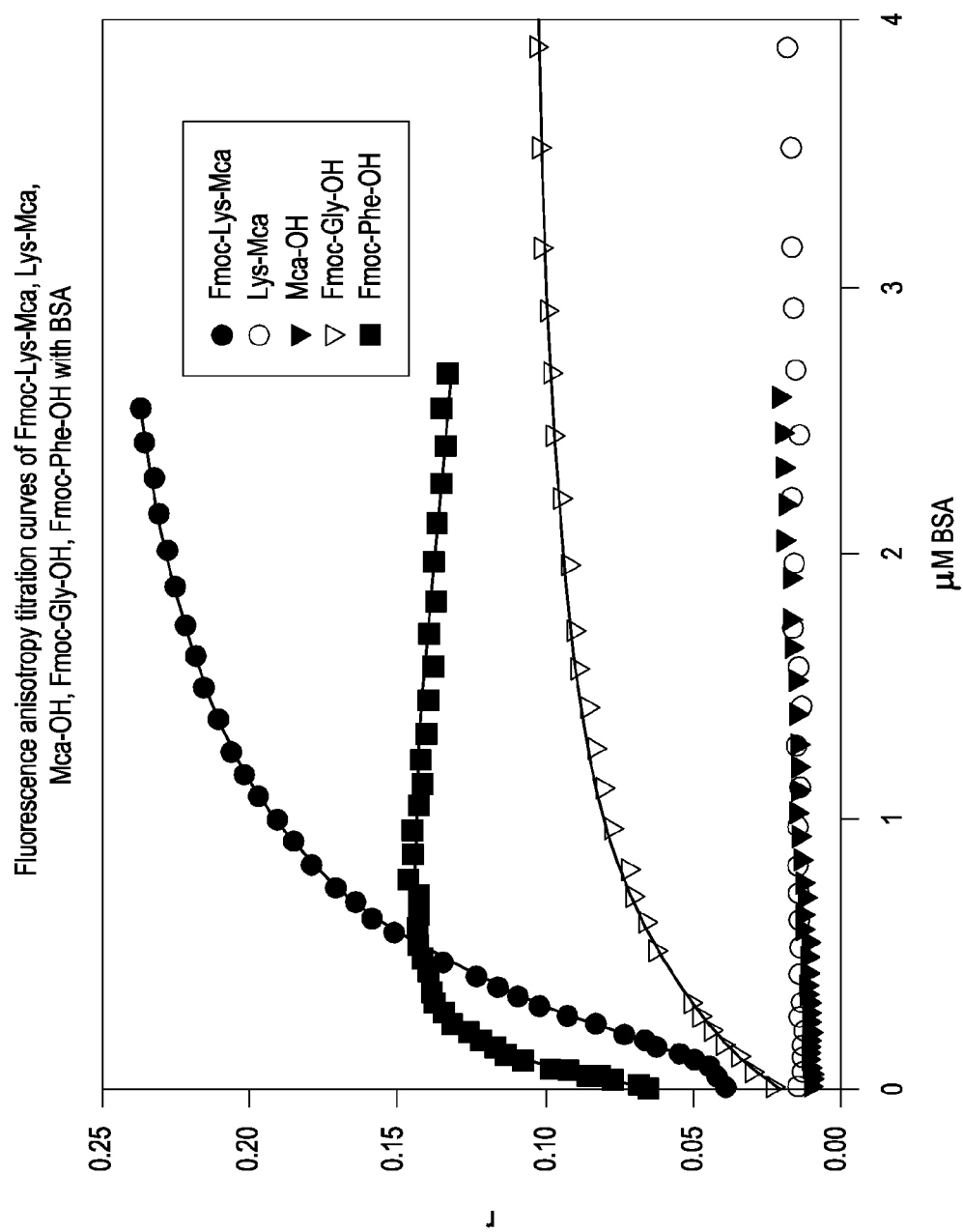
FIG. 4 shows a fluorescence anisotropy plot for the binding of Fmoc derivatives with BSA.

Using an extinction coefficient of 12900/M/cm at $A_{324}$, the concentration of the fluorophore methoxy-coumarin (or Mca, which is coupled to the —NH2 of Lys) on Fmoc-Lys-Mca (obtained from Nova Biochem) could be estimated. The $A_{280}$ is 0.667 AU/mg/mL for BSA. Using a Horiba Jobin Yvon Fluorimeter (Longjumeau Cedex, France), 500 nM of Fmoc-Lys-Mca in 1.2 ml of PBS (25 mM potassium phosphate, 125 mM NaCl, pH 7.4) was titrated with 40 increasing aliquots of a total of 250 μl of 15 μM BSA (in PBS), and the change in r was recorded as a function of increasing concentrations of BSA. Excitation was specific for coumarin (328 nm), and emission at 393 nm. Integration time was usually set to at least 10 sec, and excitation/emission slit widths were adjusted depending on the concentration and quantum yield of fluorophore: here it was 2 nm for excitation, and 10 nm for emission. After fitting the data, the experiment showed that Fmoc-Lys-Mca binds BSA tightly at a $K_d$ of 340+/−40 nM (FIG. 4).

Lys-Mca

To determine whether Mca or Fmoc are responsible for binding BSA, the Fmoc group was removed by 20% piperidine in DMF. Fmoc-Lys-Mca treated in this manner was added to 10 times the volume in ether, and Lys-Mca was precipitated. The precipitate was lyophilised, redissolved and purified on an analytical C18 reverse column using acetonitrile/$H_2O$/0.1% TFA as solvents. Pure Lys-Mca was evident by the absence of the characteristic absorbance peak of Fmoc at $A_{299}$, and absence of the mass of Fmoc-Lys-Mca on the mass spectrum (using a MALDI TOF, Voyager, Applied Biosystems). Using the same fluorimeter settings as above, no binding (i.e. change in anisotropy) could be observed for Lys-Mca, suggesting the Fmoc moiety is responsible for the binding event (FIG. 4).

Mca-OH

Mca-OH (Nova Biochem) was tested to verify the finding above. As Lys-Mca, Mca-OH did not bind BSA, as evidenced by a lack of anisotropy change during the titration with BSA (FIG. 4).

Fmoc-Gly-OH

To determine whether a neighbouring group (here, Gly) on Fmoc affects binding to BSA, a similar experiment was run with Fmoc-Gly-OH (Nova Biochem). The intrinsic fluorescing properties of Fmoc were used for the anisotropy experiments. Fmoc exhibits two distinct absorption peaks at 288 and 299 nm. The extinction coefficients of Fmoc-Gly-OH, as determined by weighing a defined amount in a defined quantity of DMF, diluting this 1000-fold in PBS and recording the absorption of it at both 288 and 299 nm, are 4800 and 5300/M/cm at $A_{288}$ and $A_{299}$, respectively. Fmoc-Gly-OH had its maximum fluorescence at 315 nm, so the fluorescence anisotropy titration experiment was run at 288 excitation and 315 emission wavelengths, at slit widths of 5 and 7 nm, respectively. The concentration of Fmoc-Gly-OH in the cuvette was 0.5 µM as before (in 1.2 ml), and a total of 250 µl of 62.7 µM BSA was titrated into it. The $K_d$ was 420+/−40 nM, which is almost the same as with Fmoc-Lys-Mca.

Fmoc-Phe-OH

To determine whether a neighbouring hydrophobic bulky group has an enhancing or adverse effect on BSA binding, Fmoc-Phe-OH was tested as above. The extinction coefficient determined here was 4240/M/cm at $A_{288}$. Because binding was tighter, the concentration of fluorophore (Fmoc-Phe-OH) had to be reduced to 100 nM for more accurate determination of $K_d$, which was titrated with 250 I of 15.7 µM BSA. The $K_d$ was ~100 nM, so significantly tighter than with Fmoc-Gly-OH, indicating that a neighbouring hydrophobic group (the phenyl ring) has a positive effect on the binding of Fmoc to BSA (FIG. 4).

Binding of Fmoc-Phe-OH to Human Serum Albumin (HSA)

Figure 5:
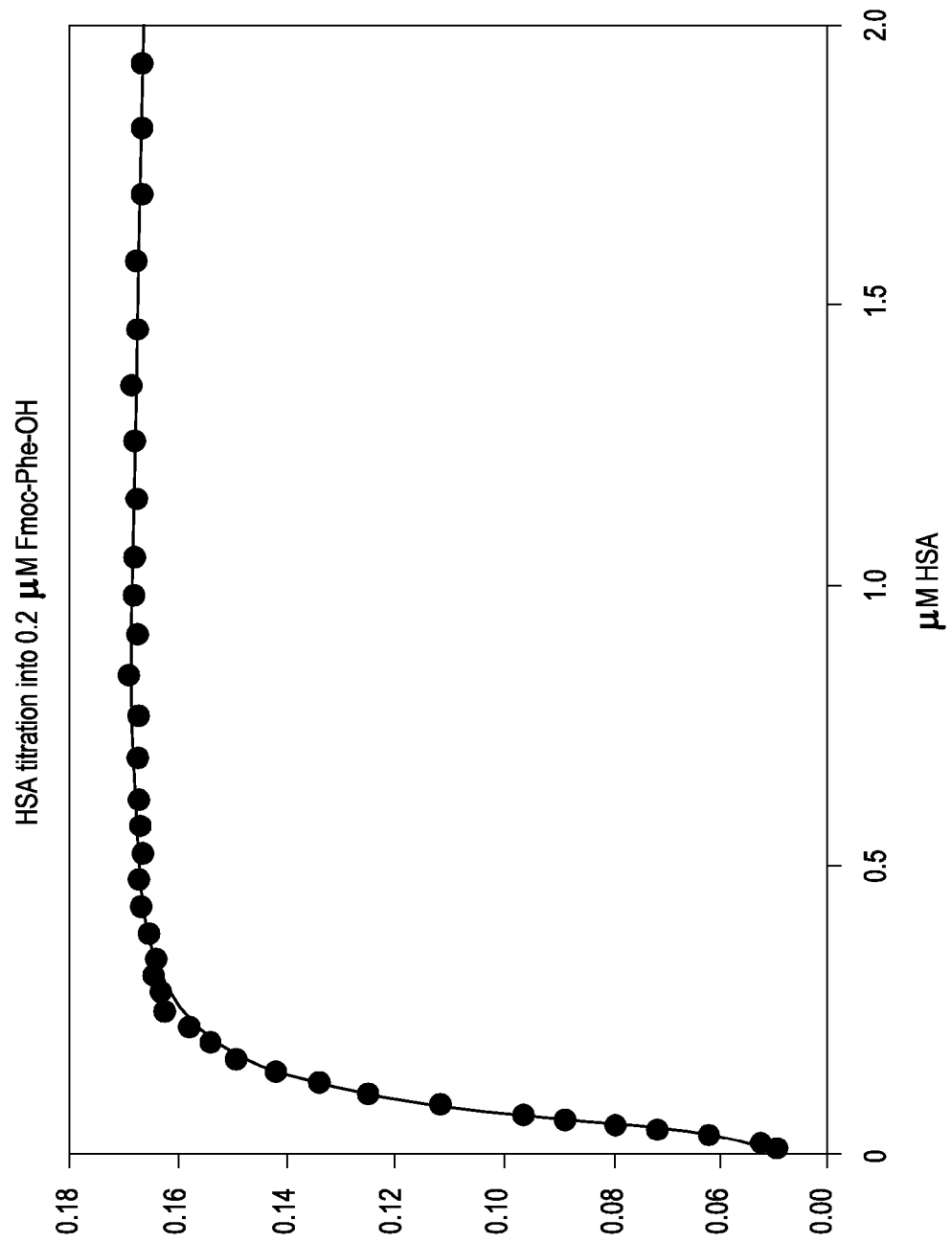
FIG. 5 shows a fluorescence anisotropy plot for the binding of Fmoc-Phe-OH with HSA.

As Fmoc-Phe-OH binds bovine serum albumin with high affinity, we tested whether the same can be observed for the human homologue, HSA. 250 µl HSA at 12.6 µM (using an extinction coefficient of 36600/M/cm, Moreno et al) was titrated into 200 nM of Fmoc-Phe-OH. The affinity was significantly higher ($K_d$~10 nM) than with BSA ($K_d$~100 nM), and binding is slightly cooperative (hence the Hill equation was used for data fitting) (FIG. 5). The $K_d$ cannot be determined accurately, however, as the fluorophore concentration is significantly above $K_d$; more accurate $K_d$ determination will require a fluorophore with a better quantum yield either by chemically modifying Fmoc or by adding a better fluorophore C-terminal to the phenylalanine (while it should not interfere with HSA binding).

Binding of Fmoc-Pentapeptides to Bovine Serum Albumin

Synthesis and Purification of Fmoc-5-Mer Derivatives:

Peptides Fmoc-GGSGD-NH2 (SEQ ID NO. 13), Fmoc-FGGGD-NH2 (SEQ ID NO. 14), Fmoc-FGSGD-NH2 (SEQ ID NO. 15) and Fmoc-WGSGD-NH2 (SEQ ID NO. 16) were synthesised with a CEM Microwave peptide synthesiser (NC, USA) at a 0.1 mmole scale, using standard protocols supplied by the manufacturer. The solid phase resin employed was PAL-PEG-PS from Applied Biosystems. Removal of protecting groups and cleavage off the resin post synthesis was achieved with shaking the resin with 95% trifluoroacetic acid (TFA), 2.5% triisopropylsilane, and 2.5% H₂O for 3 hours. All peptides were capped with an N-terminal Fmoc, and a C-terminal amide (NH2). After cleavage, peptides were lyophilised, and solubilised in 5 mL of DMF. 100 µl of this was loaded onto an analytical C18 column using a Waters HPLC, using methanol and water (both in the presence of 0.1% TFA) as solvents. Fmoc peptides eluted at >80% of methanol, and were free of impurities.

Fmoc-GGSGD-NH2 (SEQ ID NO. 13)

Figure 6:
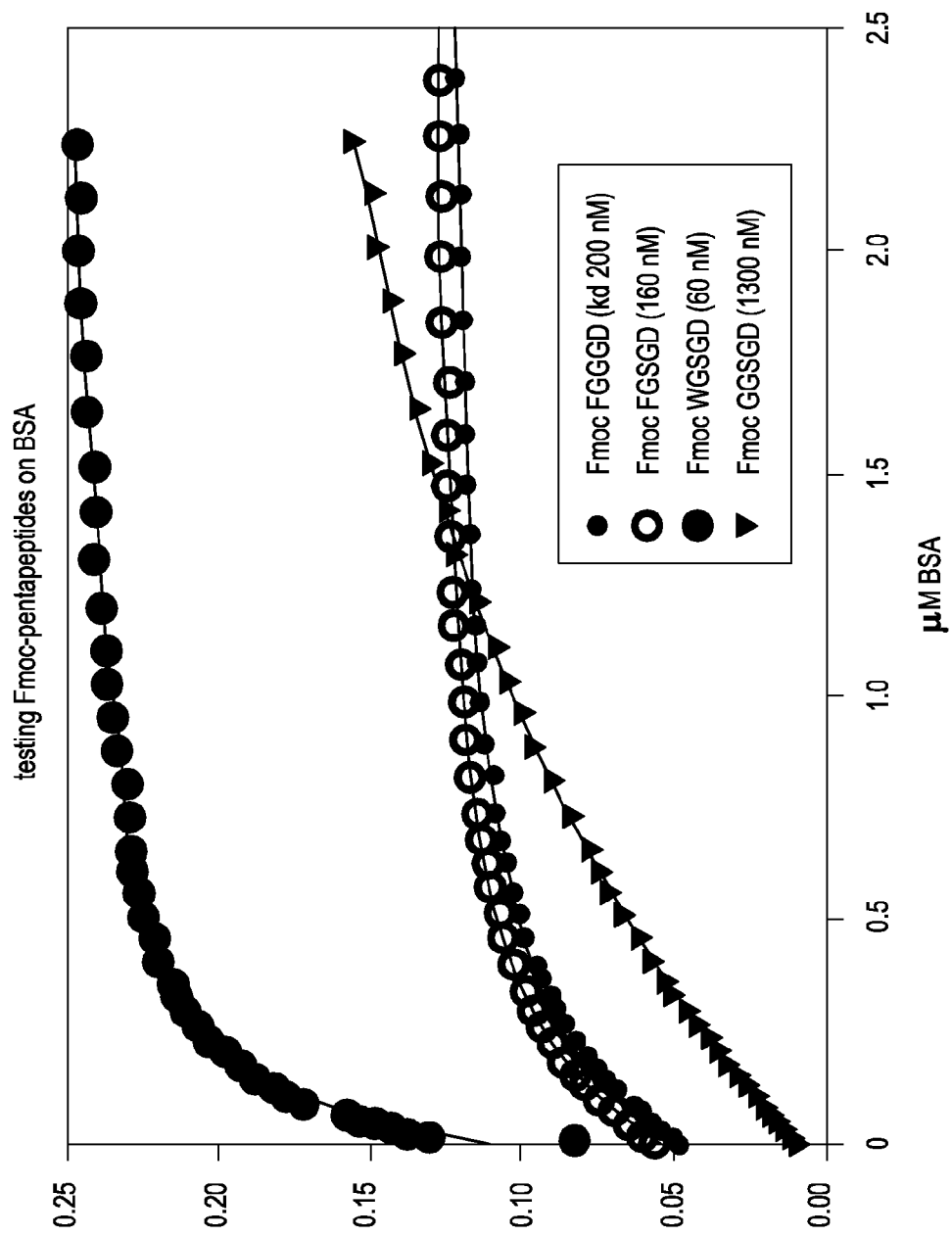
FIG. 6 shows a fluorescence anisotrophy plot for pentapeptide Fmoc derivatives with BSA; FGGD (SEQ ID No. 14), FGSGD (SEQ ID No. 15), WGSGD (SEQ ID No. 16), GGSGD (SEQ ID No. 13).

Peptide concentrations were estimated by the extinction coefficient of 5300/M/cm at $A_{299}$ for Fmoc (see above). The peptide concentration in the cuvette was 200 nM. This was titrated with 250 µl BSA at 13.1 µM, using 299 and 315 nm for excitation and emission wavelengths, respectively. The affinity of this peptide for BSA was 1300+/−380 nM, which is weaker than the respective Fmoc-Gly-OH. This indicates that the additional amino acids GSGD have a negative effect on binding BSA (FIG. 6).

Fmoc-FGSGD-NH2 (SEQ ID NO. 15)

We determined whether the enhancing effect of the phenylalanine adjacent to Fmoc on binding BSA is also observable in the penta-peptide Fmoc-FGSGD-NH2 (SEQ ID NO. 15). At concentrations and settings as for Fmoc-GGSGD-NH2 (SEQ ID NO. 13), the $K_d$ was 160+/−20 nM, so 8-fold tighter than the glycine variant. This confirms that Phe (adjacent to Fmoc) enhances binding also in the context of a longer peptide sequence (FIG. 6).

Fmoc-FGGGD-NH2 (SEQ ID NO. 14)

This peptide, with a central glycine rather than a serine (see Fmoc-GGSGD-NH2 (SEQ ID NO. 13 for comparison) was made to see whether the lack of the extra serine side chain had a significant effect on BSA binding. The titration experiment revealed a slightly lower affinity ($K_d$=200+/−40 nM), indicating that different side chains on amino acid 3 (counting from the Fmoc group) may have effects on binding BSA (FIG. 6).

Fmoc-WGSGD-NH2 (SEQ ID NO. 16)

This experiment was run to see whether a Trp (rather than Phe or Gly)C-terminal to the Fmoc had a further enhancing effect of Fmoc binding to BSA. Here, 0.4 µM of peptide was used, with 13.1 µM of 250 µL BSA (as above). Excitation was at 299 nm (to minimise Trp absorption), and emission at 320 nm. Slit widths were at 5 and 12 nm, respectively. The affinity (Kd ~60+/−8 nM) was 3-fold tighter than with Fmoc-FGSGD-NH2 (SEQ ID NO. 15), indicating that the larger hydrophobic group is beneficial to binding BSA. Thus, from all the sequences investigated, Fmoc-Trp-GSGD (SEQ ID NO 16) is optimal for binding BSA (FIG. 6).

Binding of FMOC Bicyclic Peptide to Serum Albumin and Two Other Targets.

Peptide Synthesis and Purification

Figure 7A:
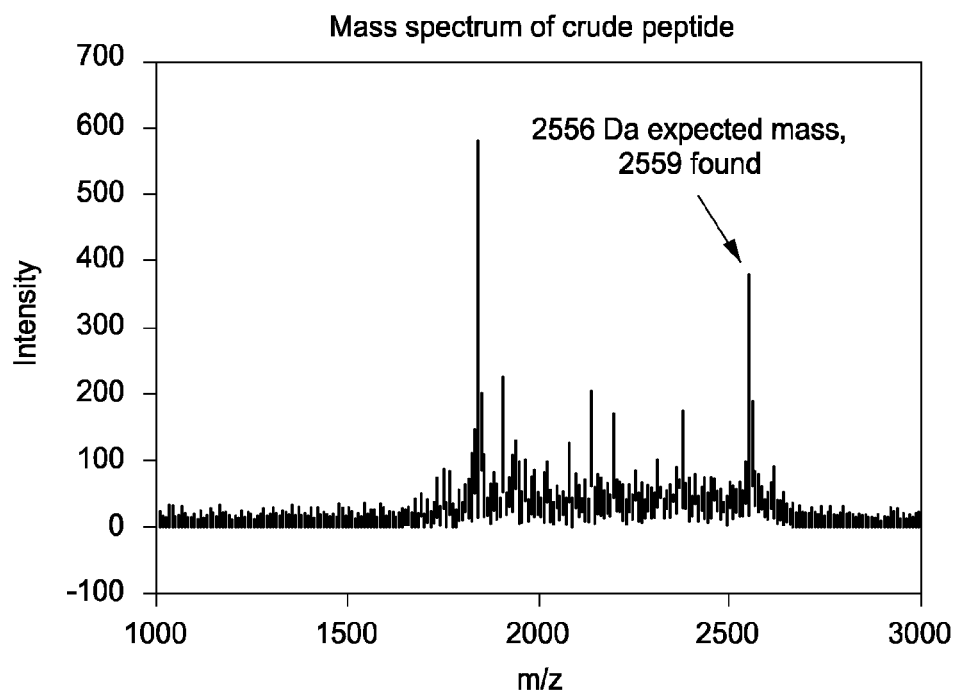
FIGS. 7A and 7B show mass spectrum and HPLC analysis of a synthesised peptide, Fmoc-WGGGACVRFGWTC-SDRFRNCG-NH$_2$ (SEQ ID No. 12)
Figure 7B:
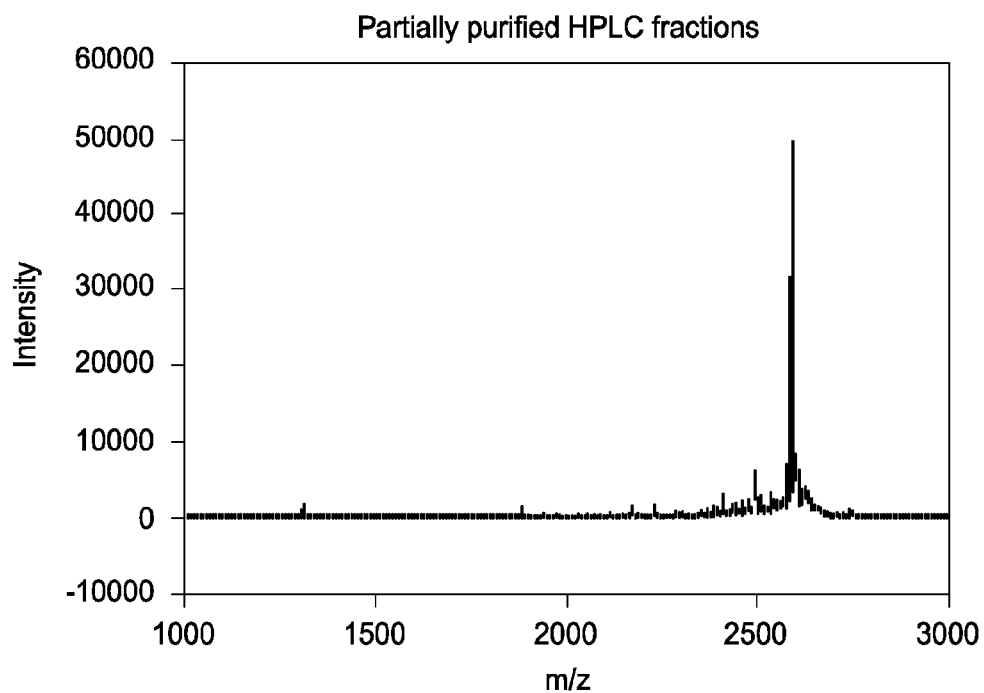
Figure 7C:
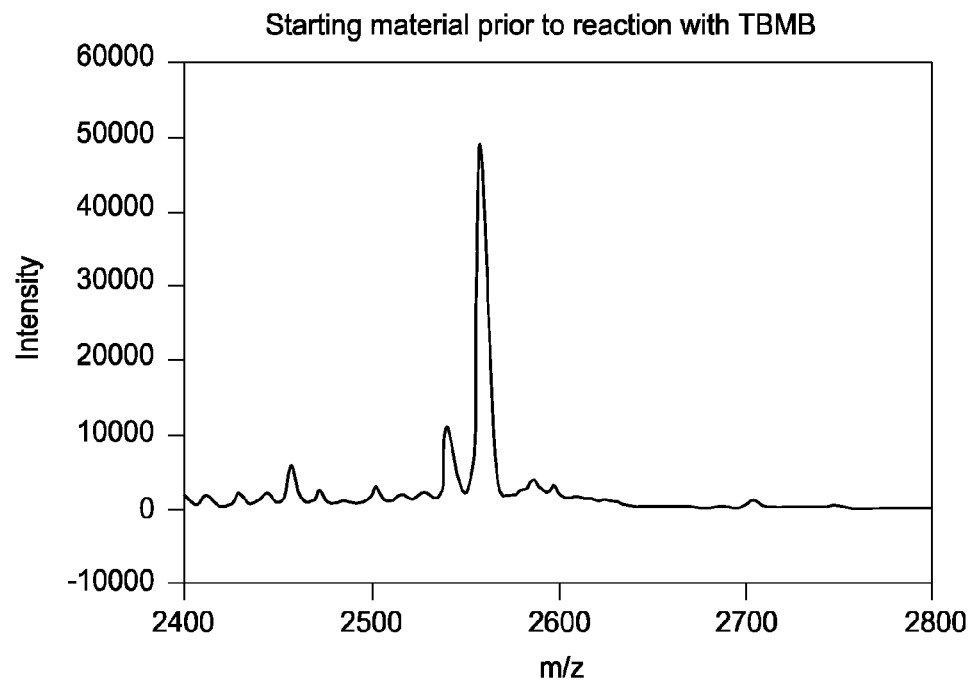
FIGS. 7C and 7D show mass spectra for the polypeptide before and after conjugation to TBMB.

The peptide was synthesised as before using a CEM microwave synthesiser. The sequence was Fmoc-WGGGACVRFGWTCSDRFRNCG-NH2 (SEQ ID NO. 17). All Cys and Arg were coupled for 30 min at room temperature, and the last 5 residues (WGGGA (SEQ ID NO. 18)) were capped after the coupling step. After lyophilisation, the peptide was dissolved in 80/20 DMF/H₂O and centrifuged. 5 mL of the supernatant was loaded onto a C18 preparative column on the same Waters system. Solvents were acetonitrile/H₂O/0.1% TFA, and elution of >90% pure peptide occurred at ~50% acetonitrile. The yield was 36 ml of ~300 µM peptide (FIG. 7A, B).

Derivatisation with TBMB

Figure 7D:
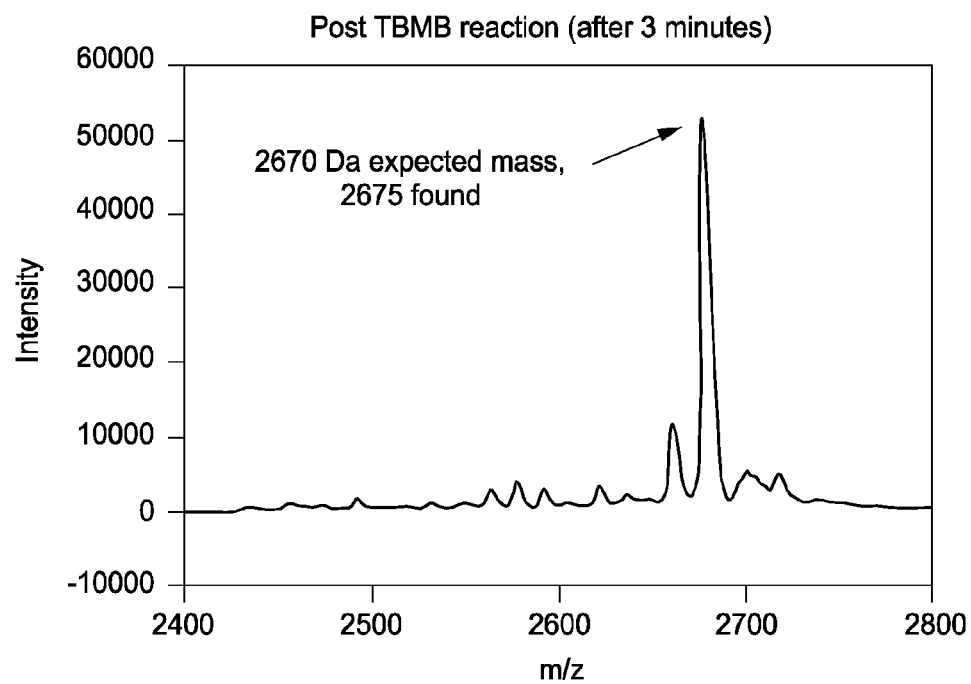
Figure 7E:
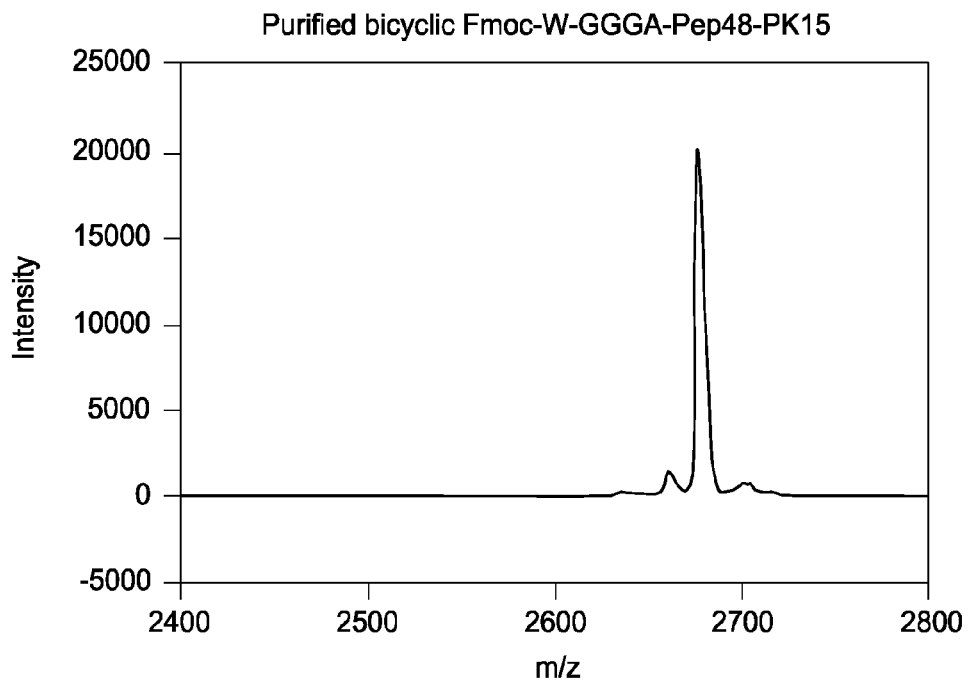
FIG. 7E shows the HPLC analysis for the conjugate (WGGGA (SEQ ID No. 19)). See Example 3.

The peptide contained in the HPLC fractions obtained above was directly reacted with TBMB. First, the concentration was estimated at $A_{299}$ using Fmoc as the chromophore (300 µM). To 10 ml of this, 0.4 ml of 1M ammonium bicarbonate in $H_2O$ was added to obtain a final concentration of 40 mM—which is sufficient to neutralise the TFA present in the solution, and sufficiently in excess (32 mM) to act as a scavenger for nascent HBr that forms as a result of the reaction between TBMB and peptide. To this, 40 µl of 100 mM TBMB in acetonitrile was added to give a final concentration of 400 µM of TBMB. The reaction was followed by mass spectrometry, and was complete after 3 minutes, with no starting material remaining, and no major side products occurring (FIG. 7D). The TBMB-coupled peptide was then purified by HPLC as above, where the reaction mixture was directly loaded onto a C18 preparative column (FIG. 7 E). Yield: 13 ml of 92 µM of bicyclic Fmoc-WGGGA (SEQ ID NO 18)-PEP48L1-PK15-L1.

Activity of bicyclic Fmoc-WGGGA (SEQ ID NO. 18)-PEP48L1-PK15L1 to BSA

Figure 8:
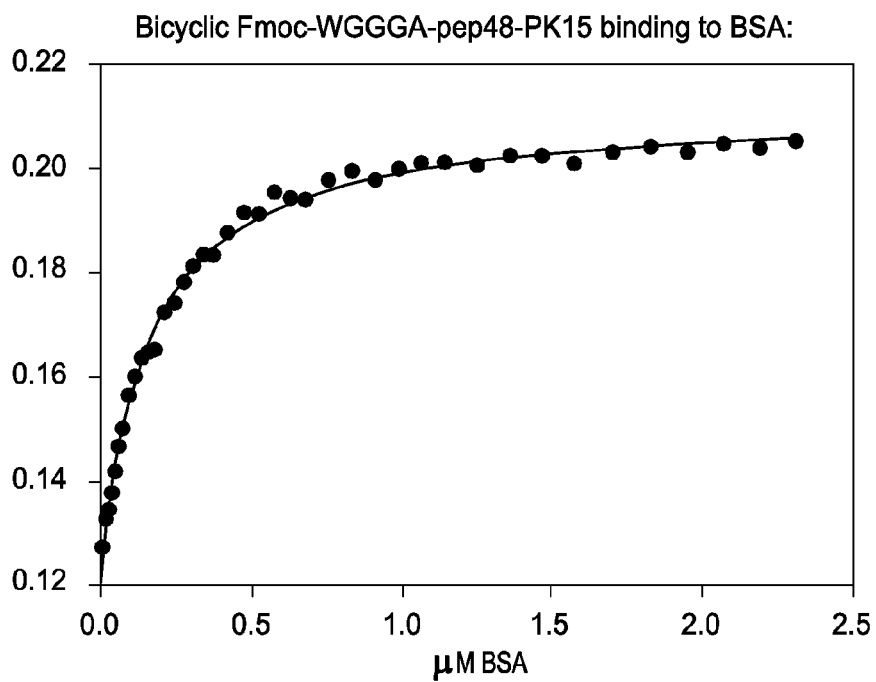
FIG. 8 shows the binding of the conjugated peptide to BSA via the Fmoc group (WGGA (SEQ ID No. 19)).

As the bicyclic peptide was not well soluble in water, it was first solubilised in DMF and then diluted into PBS. For the experiment, a total of 250 µL of 13.5 µM BSA was titrated in increasing aliquots into 1.2 mL of 500 nM peptide. Peptide concentrations were estimated by the absorbance at 299 nm, using the extinction coefficient of 4700/M/cm. Excitation was at 299 nm, and emission was set to 320 nm, at slit widths of 5 and 12 nm, respectively. The data could be fit to one of the standard ligand binding equations $(r=F^*[c]/(K_d+[c])+offset$, where r is the observed value in anisotropy, F a scaling factor, [c] the concentration of titrant (here, BSA)), and the dissociation constant $K_d$ was 62+/−14 nM. Thus the Fmoc-Trp-GGG moiety is fully functional in binding BSA when linked to the bicyclic peptide PEP48L1-PK15-L1 (FIG. 8).

Activity of Bicyclic Fmoc-WGGGA (SEQ ID NO. 18)-PEP48L1-PK15L1 to Mdm2

Figure 9:
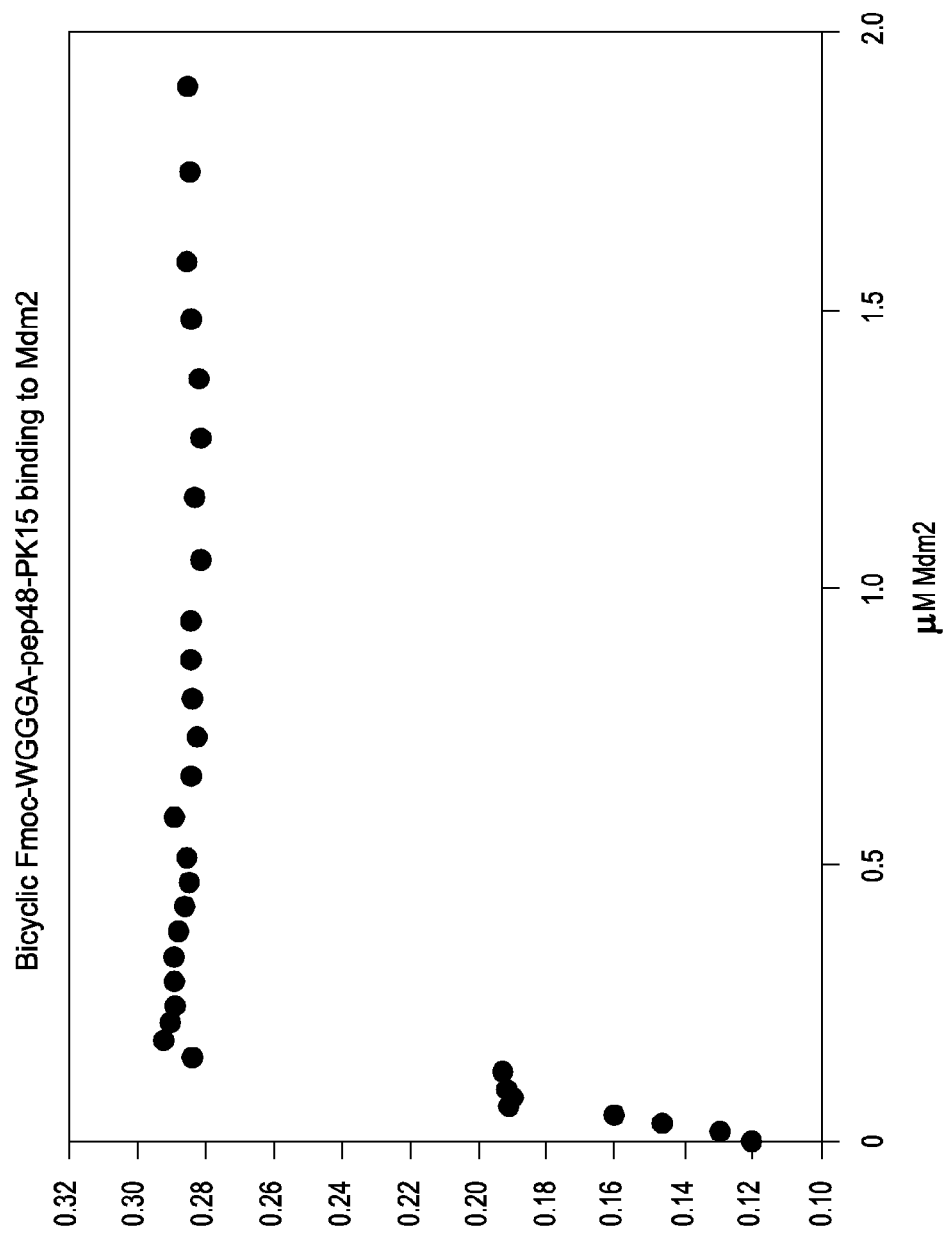
FIG. 9 shows the binding of the conjugated bispecific peptide to MDM2 (WGGA (SEQ ID No. 19)).

Mdm2 binds the complete PEP48 peptide with good affinity. We now determined whether Mdm2 binding is still functional within the Fmoc-Trp-linker-bicyclic derivative. 250 µL of 18.8 µM Mdm2 (expressed and purified as described in Teufel et al, PNAS 2007) was titrated into 1.2 ml of 500 nM peptide. A strong binding event occurred ($K_d$<1 µM), however, the data could not be fitted as the $K_d$ was too far below the concentration of peptide employed in the experiment (FIG. 9). Lower concentrations of peptide could not be used due to technical limitations. Accurate determination of dissociation constants of this peptide to Mdm2 will require a better fluorophore than Fmoc (see above), or different methodologies such as isothermal titration calorimetry (ITC).

Example 4

Creation of Bispecific Bicyclic Peptides by Shuffling of Repertoires

In Example 2 it is shown that the combination of loops from individual bicyclic peptides directed against two different targets can lead to bicyclic peptides with dual specificity. However there is an unpredictable loss of binding affinity. A general alternative is to combine repertoires of loops rather than individual loops, and there are multiple ways in which this can be done.

A first approach is to make a repertoire of bicyclic peptides (with diversity in both loops) using a scaffold such as trisbromomethylbenzene able to form three covalent bonds with three cysteines of the peptide. The repertoire can then be selected against target A for at least one round, or until sequencing of the selected clones reveals evidence of consensus sequences in the first (or second) loop. The first (or second) loop repertoire can then be combined with a similar naïve second (or first) loop repertoire as appropriate at a common cysteine, and the combined repertoire of two loops on a trivalent scaffold selected against target B for at least one round. By alternating subsequent selections of the combined repertoire between the two targets, it is possible to derive bicyclic peptides with dual specificity.

A second approach is to make a repertoire of bicyclic peptides as above, then select it against target A, and a similar repertoire separately against target B, in each case for at least one round. The first (or second) loop repertoires of target A would then be combined with the second (or first) loop repertoires of target B as appropriate at a common cysteine, to give a combined repertoire of two loops on a trivalent scaffold. By alternating selections of the combined repertoire with the two targets, it is possible to derive bicyclic peptides with dual specificity.

A third approach is to make a repertoire of monocyclic peptides (with diversity in the loop) using a scaffold such as bisbromomethylbenzene able to form two covalent bonds with two cysteines of the peptide, then to select it against target A, and a similar library separately against target B, in each case for at least one round. The loop repertoires of target A can then be combined with the loop repertoires of target B at a cysteine, and then conjugated to a trivalent scaffold such as trisbromomethylbenzene. By alternating selections of the combined two loop repertoire between the two targets, it is also possible to derive bicyclic peptides with dual specificity. A variation of this strategy is to make the monocyclic peptide repertoires by allowing pairing between the cysteines at the base of the loops (in this case the phage can simply be harvested from culture and the disulphide allowed to form naturally by air oxidation).

In all three possibilities, it is likely that the binding affinities of the bicyclic peptides will not be optimal for each target. These can be improved by synthesizing the DNA encoding the peptides with spiked oligonucleotides, and thereby making a repertoire of mutant bicyclic peptides on phage after reaction with a trivalent scaffold. The repertoire can be selected with both targets as above except under more stringent conditions (for example, long wash times, or lower concentrations of target).

The ability to make peptide repertoires with loops that can be plugged in and out requires design of suitable vectors. These can either have built in restriction sites, or conserved stretches of nucleotides adjacent to the loops suitable for PCR amplification by synthetic DNA primers. For the purposes of illustration we describe below the use of restriction sites, but the essential modular features will be similar for the PCR strategy.

FIRST LIBRARY—SINGLE LOOP (for target A). A first peptide library comprising a single loop can be designed according to the general formula Nterm-C-$X_1$-C-$R_1$-Fusion-$R_2$ for an expression cassette within a vector. Within the cassette, Nterm denotes the N-terminal flanking sequence of a single loop library, C denotes a cysteine residue, $X_1$ denotes a first sequence of randomised amino acid residues, $R_1$ denotes one or more amino acids C-terminal to the second cysteine residue and encoded by a DNA sequence forming a first restriction site, Fusion denotes at least part of a polypeptide fused to the peptide and finally $R_2$ denotes amino acids encoded by DNA forming a second restriction site. The second cysteine residue may form together with $R_1$ the first restriction site.

FIRST LIBRARY—TWO LOOPS (for target A). A first peptide library comprising two loops can be designed according to the general formula Nterm-C-$X_1$-C-$R_1$-$X_2$-C-Fusion-$R_2$ for an expression cassette within a vector. Notations within the cassette are as above, while $X_2$ denotes a second sequence of randomized amino acids.

SECOND LIBRARY—SINGLE LOOP (for target B). A second peptide library comprising a single loop can be designed according to the general formula Nterm-C-$R_1$-$Y_1$-C-Fusion-$R_2$ for an expression cassette within a vector. Notations within the cassette are as above, while $Y_1$ denotes a third sequence of randomized amino acid residues.

SECOND LIBRARY—TWO LOOPS (for target B). A second peptide library comprising two loops can be designed according to the general formula Nterm-C-$R_1$-$Y_1$-C-$R_3$-$Y_2$-C-Fusion-$R_2$, wherein $Y_2$ denotes a fourth sequence of randomized residues (other notations as above).

Note that in these designs, the first and second single loop libraries can readily be derived from the corresponding two loop libraries. For example, with the two loop libraries, after target selection the second loop can be removed by digestion with restriction enzymes specific for sites $R_1$ and $R_2$ (for cassette Nterm-C-$X_1$-C-$R_1$-$X_2$-C-Fusion-$R_2$) or after digestion with restriction enzymes specific for sites $R_3$ and $R_2$ (for cassette Nterm-C-$R_1$-$Y_1$-C-$R_3$-$Y_2$-C-Fusion-$R_2$). Digestion is followed by insertion through ligation of the DNA for the partial cassette $R_1$-Fusion-$R_2$ or $R_3$-fusion-$R_1$ (which can be prepared by PCR with suitable primers) yielding single loop libraries of the design Nterm-C-$X_1$-C-$R_1$-Fusion-$R_2$ or Nterm-C-$R_1$-$Y_1$-C-$R_3$-Fusion-$R_2$.

The libraries can also be readily recombined by suitable cutting and pasting at the three restriction sites. Vector DNA for the pool of selected, target-specific (phage-) clones from the first library is prepared from bacteria expressing the pool of phages. DNA comprising at least the expression cassette of the second library is also prepared, for example by PCR amplification of the DNA from a pool of selected phages. Vector DNA from the first library and DNA comprising at least the expression cassette of the second library are digested with restriction enzymes specific for DNA encoding $R_1$, and $R_2$ followed by ligation and transformation into bacteria for expression. This yields a combinatorial library comprising the $X_1$-loop of a first (target A-selected) library followed by the $Y_1$-loop of a second (target B-selected) library. Clones in the resulting library will harbour the resulting expression cassettes Nterm-C-$X_1$-C-$R_1$-$Y_2$-C-Fusion-$R_2$ or Nterm-C-$X_1$-C-$R_1$-$Y_2$-C-$R_3$-Fusion-$R_2$ (notations as above).

Example 5

Protease Resistance of Bicyclic Peptides

The bicyclic peptides PK15 and CG4 of Heinis et al., 2009, were selected against the proteases kallikrein and cathepsin G respectively, and it would not be surprising if the bicyclic peptides are resistant to digestion by these proteases, particularly the constrained nature of the scaffold should help protect against proteolytic attack.

We compared PK15 linear (cysteines treated with iodoacetamide) with PK15 conjugated to the TBMB scaffold, with kallikrein and with other proteases, see Table below (the scale ranges from +++ (substantially intact) to − (completely cleaved). As expected the PK15 conjugate with TBMB was more resistant than the linear to attack by kallikrein. The factor was about 100 fold, as shown by comparing different concentrations of enzyme.

For the other proteases, the factor ranged between 10 and 100 fold, depending on the protease. We also compared the resistance of the bicyclic CG4L1-PK15L1 (Example 2) to proteolysis. In this case the factor ranged between 1 and more than 100 fold, depending on the protease. Thus the conjugate has an increased resistance to proteases other than to the protease (kallikrein) that it was exposed to during the selection process.

The variation of resistance according to the protease suggests that it is desirable to include a proteolysis step in the selection or the screening process, as already described in Example 1. Most desirable will be to use a protease that is active under the conditions in which the bicyclic peptide will be used, for example in the presence of serum. For interest we checked the resistance of PK15 to serum. This showed that the linear PK15 is digested by the proteases in serum at 37° C. within about 2 hours. However the PK15 conjugate resists proteolysis for at least 48 hours; later times have yet to be tested.

TABLE

Peptide conjugate digestion with various proteases.

|  | PK15 linear | PK15-TBMB | CG4L1-PK15L1 linear | CG4L1-PK15L1 TBMB |
|---|---|---|---|---|
| Cathepsin G |  |  |  |  |
| 1 | − | ++ | − | ++ |
| 0.1 | − | +++ | − | +++ |
| 0.01 | +/ | +++ | − | +++ |
| Chymotrypsin |  |  |  |  |
| 10 | − | ++ | − | − |
| 1 | − | +++ | − | + |
| 0.1 | + | +++ | − | ++ |
| 0.01 | +++ | +++ | ++ | +++ |
| Kalikrein |  |  |  |  |
| 1 | − | +++ | − | ++ |
| 0.1 | + | +++ | − | +++ |
| 0.01 | +++ | +++ | − | +++ |
| Pronase |  |  |  |  |
| 10 | − | + | + | ++ |
| 1 | +/− | ++ | ++ | +++ |
| 0.1 | ++ | +++ | ++ | +++ |
| 0.01 | +++ | +++ | +++ | +++ |
| Proteinase K |  |  |  |  |
| 10 | − | ++ | − | +/− |
| 1 | +/− | +++ | + | + |
| 0.1 | + | +++ | + | + |
| 0.01 | ++ | +++ | ++ | ++ |
| Subtilisin |  |  |  |  |
| 9 | − | − | − | − |
| 0.9 | − | + | − | +/− |
| 0.09 | ++ | ++ | − | + |
| 0.009 | +++ | +++ | − | +++ |
| Trypsin |  |  |  |  |
| 10 | − | − | − | − |
| 1 | − | + | − | + |
| 0.1 | +/− | ++ | − | ++ |
| 0.01 | + | +++ | +/− | +++ |

Numbers correspond to number of μg enzyme per reaction

Methods

Linear peptides (PK15 and CG4L1-PK15L1) were first treated with iodoacetamide prior to digestion studies. The peptides (ca 3-4 mg) were purified by HPLC (semi-prep Proteo column as described in general methods), and the HPLC fraction (ca 3 ml) was neutralised with an equal volume of 50 mM ammonium bicarbonate. Iodoacetamide (3 mg, ca 9 equivalents) in acetonitrile (1 ml) was added and the reaction left at room temperature until mass spectroscopy showed completion of reaction (typically 2-3 hrs). The reaction mixture was concentrated (rotary evaporator) and re-purified by HPLC as above.

Peptides (linear and conjugates) were dissolved in water at a concentration of 1 mg/ml, giving an effective concentration of ~0.5 mM stock solutions. 2 µl of peptide conjugates (~30 µM in reactions depending on actual molecular weight) where dissolved in reaction buffer (see below) in a total reaction volume of 30 µl, followed by the protease, and samples were incubated at 37° C. for 1 hr. 10 µl aliquots were quenched into 20 µl of 10% dichloroacetic acid in MeCN/H$_2$O (1:1) and stored at −20° C. for 30 minutes, centrifuged at 4° C. (13000 rpm) for 5 minutes and then spotted onto MALDI-TOF mass spectrometer plate for analysis.

All reactions at 37° C. Cathepsin G and kalikrein reactions were carried out in 10 mM Tris pH 7.4, 150 mM NaCl, 10 mM MgCl$_2$, 1 mM CaCl$_2$, 0.1% BSA, 0.01% Triton X100, 5% DMSO. Chymotrypsin reactions were carried out in 100 mM Tris pH 7.4, 10 mM CaCl$_2$. Pronase and proteinase K reactions were carried out in 100 mM Tris pH 7.4, 0.5% SDS. Subtilisin reactions were carried out in 50 mM KH$_2$PO$_4$ pH 7.5. Trypsin reactions were carried out in 67 mM sodium phosphate pH 7.6. Reaction conditions with serum involve dissolving the peptide in 1×PBS (total volume 24 µl) and 6 µl of human serum added to the reaction.

Example 6

Bicyclic Peptide-Fc Fragment Conjugates

A bicyclic peptide was chemically conjugated to the Fc fragment of an antibody to prolong its circulatory half-life. Fc domains of antibodies bind to the neonatal Fc receptor (FcRn) mediating IgG recycling, therefore retaining the protein and conjugates thereof for a long time (typically several days) in the circulation. Binding to FcRn also mediates transcytosis across endothelial and epithelial barriers, permitting aerosol delivery of IgG and Fc and conjugates thereof.
Preparation of Maleimide-Functionalyzed Bicyclic Peptide PK15

The bicyclic peptide PK15 ($NH_2$-ACSDRFRNCPADEALCG-$NH_2$ (SEQ ID NO. 19) conjugated to TBMB) was modified at the N-terminus with the amine- and sulfhydryl-reactive linker (N-e-maleimidocaproyloxy)succinimide ester) (EMCS). 50 mL of the linker (2 mM) dissolved in DMSO was added to 950 mL of PK15 (50 mM) in 50 mM Tris pH 8, 100 mM NaCl, mixed and incubated at 25° C. for one hour. The reaction product was purified chromatographically.

Preparation of Fc Fragment

Fcgamma1 fragment was prepared either from human normal IgG1 by digesting the protein with papain and selective reduction of interchain disulfide bridges (Stevenson, G. T. et al., Journal of Immunology, 1997) or by recombinant expression of Fc fragment in mammalian cells. In the latter case, a selenocysteine was incorporated to obtain a handle to which the bicyclic peptide could selectively be attached in a chemical reaction (Hofer, T., et al., PNAS, 2008).

For the enzymatic preparation of Fc fragment, 20 mg/ml IgG were incubated with papain (0.5 mg/ml) at 37° C. and pH 6.7 for 20 minutes in the presence of 0.5 mM 2-mercaptoethanol. Under these conditions, most IgG was cleaved and no reduction of interchain disulfide bonds was detected. The Fc fragment was separated from Fab and undigested IgG. The two interchain bonds of the fragment (at the hinge) were reduced by exposure to 1,4-dithiothreitol (DTT; 2 mM) at pH 8 and 25° C. for 15 minutes. The DTT was removed and the buffer exchanged to 0.1 M acetate buffer, pH 5. One of the reduced cysteines was reacted with N-ethylmaleimide (NEM) by addition of 0.75 equivalents of NEM and incubation at 37° C. for 2 hours. One of the disulfide bridges was then reconstituted and the remaining cysteine residue was reacted with the maleimide activated bicyclic peptide PK15 and purified by affinity chromatography using immobilized human plasma kallikrein and gel filtration.

For the recombinant expression of Fc fragment with a C-terminal selenocysteine residue, a gene encoding human IgG-derived Fc fragment, a TGA codon, a hexahistidine tag and a 3'UTR of the gene of human selenoprotein thioredoxin reductase 1 was inserted into a mammalian expression vector. The protein was expressed in HEK 293 cells in suspension with serum-free medium containing a selenocysteine source ($Na_2SeO_3$; 1 mM) and purified by nickel affinity chromatography. Incubation of purified Fc-selenocysteine protein with the maleimide-functionalized bicyclic peptide PK15 at 25° C. for 1 hour in 100 mM sodium phosphate buffer, pH 5.2 in the presence of 0.1 mM DTT led to site-selective linkage of the peptide to the Fc fragment. The Fc fragment-cyclic peptide conjugate was sequentially purified by affinity chromatography using immobilized human plasma kallikrein and by gel filtration.

Example 7

Bicyclic Peptide Conjugates that Penetrate Cells

A number of fluorescein or methoxy-coumarin-modified versions of Pep48 derivatives were prepared, containing various cell penetrating peptide (CPP) sequences or control sequences on their C-termini. The fluorophores were always coupled to the N-terminus. The sequences were as follows:

| Peptide name | Pep48 Sequence | CPP |
|---|---|---|
| Pep48-R3 | SCVRFGWTCDNSWHGCKG | RRR (SEQ ID NO. 20) |
| Pep48-D3 | SCVRFGWTCDNSWHGCKG | DDD (control) (SEQ ID NO. 21) |
| Pep48T-1 | SGCVRFGWTCPTVMCGG | RRRRR (SEQ ID NO. 22) |
| Pep48T-2 | SGCVRFGWTCPTVMCGG | $R_DR_DR_DR_DR_D$ (SEQ ID NO. 22) |
| Pep48T-3 | SGCVRFGWTCPTVMCGG | RRRRRGL (SEQ ID NO. 23) |
| Pep48T-4 | SGCVRFGWTCPTVMCGG | YGRKKRRQRRR (SEQ ID NO. 24) |
| Pep48T-5 | SGCVRFGWTCPTVMCGG | RQIKIWFQNRRMKWKK (SEQ ID NO. 25) |

CPP sequences usually contain several consecutive arginines (see Pep48-R3, Pep48T-1 and -3), and these polyarginines may be stabilised further by employing arginines in their D-form (Pep48T-2) (Schmidt et al, FEBS Letters 2009, PMID: 19925791). Pep48T-4 and Pep48T-5 contain the CPP sequences HIV-tat and Penetratin, respectively. Both CPPs have been well established in facilitating cellular uptake of target molecules (Wadia et al, Nat. Med. 2004 10(3):310-5, and Dom et al, Nucleic Acids Res. 2003, 31(2):556-61).

Pep48 sequences correspond to the sequence that is capable (as a TBMB conjugate) of binding to Mdm2 at a Kd of ~1.2 µM, as described in Example 1. Pep48T sequences correspond to more tightly binding affinity-matured Pep48 derivatives selected subsequently with an estimated Kd of 100 nM. The sequence of the first loop is identical in each case.

Two cell lines, HeLa and HCT116, were used for these experiments. HeLa is a Human Negroid cervix epitheloid carcinoma and HCT116 is a Human colon carcinoma. Both cell types are widely available; for instance, HeLa cells are available from the UK HPA under catalogue number 93021013. HCT116 cells are available from the UK HPA under catalogue number 91091005.

Cells were seeded in Lab-Tek chambered borosilicate coverglass (Nunc). After culturing for 48 hrs (cells reached 40-60% confluency), media was removed and a fresh media supplemented with 10 µM of peptides was added to the cells. Cells were cultivated for a further 3.5 hrs or 24 hrs. At the end of the incubation time cells were washed 3×DMEM and finally resuspended in DMEM complete media supplemented with 10 mM HEPES buffer. Live cell imaging was performed on a laser scanning microscope (LSM 710, Zeiss), differential interference contrast (DIC) and fluorescent images were taken.

Incubation of the fluorescein Pep48-R3 and Pep48-D3 TBMB conjugate peptides with HCT116 cells revealed fluorescent staining within the cell by the "R3" peptide but not with the "D3" peptide. This shows that the bicyclic peptide can penetrate cells, and is consistent with the literature cited above that several arginine residues may facilitate this.

Subsequent experiments on HeLa cells with the other fluorescein peptide conjugates with TBMB (Pep48T1-5), indicated that they all penetrated cells. Generally the staining was punctuate, suggesting that the peptide may have accumulated in endosomes.

The coumarin peptide conjugates with TBMB also appeared to enter the cells selectively (as shown with the corresponding "R3" and "D3" conjugates, but the fluorescence emission signal was weaker making the interpretation of the images more difficult.

Methods

Pep48T-1 to Pep48T-5 were synthesised as above at a 0.25 mmole scale, as described in Example 3, and the last 10 residues were capped after each coupling step. The resin of each of the 5 cell-penetrating peptides was then split into equal parts, deprotected with 20% piperidine in DMF and reacted with 5,6 carboxyfluorescein succinimide (5,6-FAM) (Biotium) or Fmoc-Lys-methoxycoumarin (Lys-Mca) (Novabiochem). For the former, 300 mg 5,6-FAM was dissolved in 5.1 mL DMF, and 1.02 mL Activator Base (from a stock of 34.5 mL diisopropylethylamine and 65.5 mL N-methylpyrrolidone) was added. 1.22 mL of this mixture was reacted with the deprotected DMF-washed peptide resin, and shaken at RT for 16 hrs. The resin was then drained and washed with DMF, DCM, and cleaved with TFA/triisopropylsilane/$H_2O$ as before. Lys-Mca was coupled to the N-terminus on the peptide synthesiser for 1 hour at RT, using standard coupling protocols. Fluoresceinated Pep48-R3 and Pep48-D3 were prepared as above, except at a 0.1 mmole scale.

These peptides were then conjugated to TBMB as described in Example 3, as follows. 1) Dissolution of cleaved, lyophilised peptide in 6 M guanidinium hydrochloride+DTT (0.2 g/5 mL), 2) HPLC using a $H_2O$/acetonitrile/ 0.1% heptafluorobutyric acid gradient, 3) MALDI-TOF to identify correct fractions, 4) coupling to TBMB in the presence of 40 mM ammonium bicarbonate, 5) Lyophilisation, 6) Dissolution in 6 M guanidinium hydrochloride, 6) HPLC as in 2), 7) MS as in 3), 8) final lyophilisation. The concentration of fluoresceinated peptides was estimated by using the extinction coefficient of 66,000 $M^{-1}$ $cm^{-1}$ at 492 nm for fluorescein. Similarly, coumarin-labelled peptide concentrations were determined using E=12,000 $M^{-1}$ $cm^{-1}$ at 324 nm.

The cells were cultured in Dulbecco's Modified Eagle's Medium (DMEM, GIBCO) and supplemented with 10% (v/v) of heat-inactivated fetal bovine serum, 2 mM L-glutamine, 10 U/ml penicillin, and 100 ug/ml streptomycin (DMEM complete media) at 37° C. in a 5% $CO_2$ atmosphere.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A multispecific peptide ligand comprising:
(a) a nucleic acid encoding the multispecific polypeptide;
(b) the multispecific peptide displayed on a phage display system, wherein the multispecific polypeptide comprises the sequence (X)lC(X)mC(X)nC(X)o (SEQ ID No. 26), wherein C represents the amino acid cysteine, X represents a random amino acid, m and n are numbers between 1 and 20 defining the length of intervening polypeptide segments and l and o are numbers between 0 and 20 defining the length of the flanking polypeptide segments;
(c) the multispecific peptide ligand encoded by the nucleic acid is linked to the nucleic acid by the phage; and
(d) the multispecific peptide ligand is attached to tris-(bromomethyl)benzene (TBMB) by three discrete covalent bonds between said TBMB and said multispecific peptide ligand via said C amino acid residues, and form at least one loop which comprises a sequence of two or more amino acids subtended between two of said C amino acid residues, wherein the multispecific peptide ligand is capable of binding to two or more targets, thus forming the multispecific peptide ligand.

* * * * *